US007235584B2

(12) United States Patent
Garzon et al.

(10) Patent No.: US 7,235,584 B2
(45) Date of Patent: *Jun. 26, 2007

(54) NON-PSYCHOTROPIC CANNABINOIDS

(75) Inventors: Aaron Garzon, Rehovot (IL); George Fink, Tel Aviv (IL)

(73) Assignee: Pharmos Corporation, Iselin, NJ (US)

( * ) Notice: Subject to any disclaimer, the term of this patent is extended or adjusted under 35 U.S.C. 154(b) by 254 days.

This patent is subject to a terminal disclaimer.

(21) Appl. No.: 10/602,745

(22) Filed: Jun. 25, 2003

(65) Prior Publication Data

US 2005/0032881 A1   Feb. 10, 2005

Related U.S. Application Data

(63) Continuation-in-part of application No. 10/304,074, filed on Nov. 26, 2002, now Pat. No. 6,610,737, which is a continuation of application No. PCT/IL01/00571, filed on Jun. 22, 2001.

(60) Provisional application No. 60/222,467, filed on Jul. 28, 2000.

(30) Foreign Application Priority Data

Jun. 22, 2000 (IL) ........................... 136946

(51) Int. Cl.
*A61K 31/35* (2006.01)
(52) U.S. Cl. ............... 514/454; 514/316; 514/397; 514/406; 514/320; 546/187; 546/196; 548/311.4; 548/364.4; 549/390
(58) Field of Classification Search ............... 546/196, 546/187; 548/311.4, 364.4; 514/406, 397, 514/316, 320, 454; 549/390
See application file for complete search history.

(56) References Cited

U.S. PATENT DOCUMENTS

| | | | |
|---|---|---|---|
| 5,521,215 A | 5/1996 | Mechoulam et al. | 514/454 |
| 5,538,993 A | 7/1996 | Mechoulam et al. | 514/454 |
| 5,635,530 A | 6/1997 | Mechoulam et al. | 514/454 |
| 5,872,148 A | 2/1999 | Makriyannis et al. | 514/454 |
| 5,932,610 A | 8/1999 | Shohami et al. | 514/454 |
| 6,096,740 A | 8/2000 | Mechoulam et al. | 514/236.8 |
| 6,162,829 A | 12/2000 | Burstein | 514/570 |
| 6,166,066 A | 12/2000 | Makriyannis et al. | 514/453 |
| 6,284,788 B1 | 9/2001 | Mittendorf et al. | 514/445 |

OTHER PUBLICATIONS

Barth, F., "Cannabinoid Receptor Agonists And Antagonists", Exp. Opin. Ther. Patents, vol. 8: pp. 301-313, (1998).
McIntosh, T.K., "Novel Pharmacologic Therapies In The Treatment Of Experimental Traumatic Brain Injury: A Review", Journal of. Neurotrauma, vol. 10:, pp. 215-244 (1993).

Rogawski, M.A., "Therapeutic Potential Of Excitatory Amino Acid Antagonists: Channel Blockers And 2,3-Benzodiazepines", Trends in Pharmacology. Science., vol. 14: pp. 325-331, (1993).
Danbolt, N.C., "Glutamate Uptake", Progress in Neurobiology, vol. 65: 1 pp. 1-105 (2001.).
Mechoulam, R., et al., "Endocannabinoids", Eur. Journal of. Pharmacology,, vol. 359: pp. 1-18 (1998).
Williams, C.S. et al., "Prostaglandin Endoperoxide Synthase: Why Two Isoforms?", American. Physiological.Society,, vol. 270: pp. G393-400 (1996).
Golden, B.D.et al., "Selective Cyclooxygenase-2 Inhibitors", Rheumatic Diseases Clinics of North America., vol. 25: pp. 359-378 (1999).
Smalley, W.E. et al., "Colorectal Cancer And Nonsteroidal Anti-Inflammatory Drugs", Adv. Pharmacology., vol. 39: pp. 1-20 (1997).
Lipsky, P.E., "Specific COX-2 Inhibitors In Arthritis, Oncology, And Beyond: Where Is The Science Headed?", J. Rheumatology., vol. 26: Suppl 56: pp. 25-30 (1999).
Ross, R., "Atherosclerosis, An Inflammatory Disease", New England Journal of. Medicine., vol. 340, No. 2: pp. 115-126 (1999).
Mechoulam, R., et al., "Synthesis Of The Individual, Pharmacologically Distinct, Enantiomers Of A Tetrahydrocannabinol Derivative", Tetrahedron Asymmetry, vol. 1: No. 5, pp. 315-318, (1990).
Mechoulam, R. et al., "Enantiomeric Cannabinoids: Stereospecificity Of Psychotropic Activity", Experientia, vol. 44: pp. 762-764 (1988).
Eshhar, N. et al., "Kainyl-Bovine Serum Albumin: A Novel Ligand Of The Kainate Sub-Type Of Glutamate Receptor With A Very High Binding Affinity", Brain Res., vol. 476: pp. 57-70 (1989).
Belayev, L. et al., "HU-211, A Novel Noncompetitive N-Methyl-D-Aspartate Antagonist, Improves Neurological Deficit And Reduces Infarct Volume After Reversible Focal Cerebral Ischemia In The Rat", Stroke, vol. 26: pp. 2313-2320 (1995).
Nonaka S. et al., "Neuroprotective Effects Of Chronic Lithium On Focal Cerebral Ischemia In Rats", NeuroReport, vol. 9: pp. 2081-2084 (1998).
Montoya, C.P. et al., "The "Staircase Test": A Measure Of Independent Forelimb Reaching And Grasping Abilities In Rats", Journal. Neuroscience, Methods., vol. 36: pp. 219-228 (1991).

(Continued)

*Primary Examiner*—Amelia A. Owens
(74) *Attorney, Agent, or Firm*—Winston & Strawn LLP

(57) ABSTRACT

Novel non-psychotropic cannabinoids are disclosed and pharmaceutical compositions comprising these novel compounds are described for preventing neurotoxicity, neuroinflammation, immune or inflammatory disorders comprising as active ingredient the stereospecific (+) enantiomer, having (3S,4S) configuration of $\Delta^6$ tetrahydrocannabinol type compounds. The compositions are particularly effective in alleviating and even preventing neurotoxicity due to acute injuries to the central nervous system, including mechanical trauma, compromised or reduced blood supply as may occur in cardiac arrest or stroke, or poisonings. They are also effective in the treatment of certain inflammatory disorders and chronic degenerative diseases characterized by neuronal loss and chronic pain including neuropathic pain.

20 Claims, 15 Drawing Sheets

OTHER PUBLICATIONS

Sharkey, J. et al., "Tacrolimus (FK506) Ameliorates Skilled Motor Deficits Produced By Middle Cerebral Artery Occlusion In Rats", Stroke, vol. 27, No. 12,: pp. 2282-2286 (1996).

Liberatore, G.T. et al., "Inducible Nitric Oxide Synthase Stimulates Dopaminergic Neurodegeneration In The MPTP Model Of Parkinson Disease", Nature Medicine, vol. 5, No. 12: pp. 1403-1490.

Duvdevani, R. et al., "Graded Crush Of The Rat Optic Nerve As A Brain Injury Model: Combining Electrophysiological And Behavioral Outcome", Restorative. Neurology and Neuroscience., vol. 2: pp. 31-38 (1990).

Skene, J.H.P. et al.,., "Characteristics Of Growth-Associated Polypeptides In Regenerating Toad Retinal Ganglion Cell Axons", J. Neuroscience, vol. 1, No. 4: pp. 419-426 (1981).

Leor, J.et al., "An Experimental Model Examining The Role Of Magnesium In The Therapy Of Acute Myocardial Infarction", American. Journal. Cardiology., vol. 75: pp. 1292-1293 (1995).

Dexanabinol → Compound I

Example of new analogs

PGE2 Inhibition by Dexanabinol Analogs
Dose Response

CONTRALATERAL PERFORMANCE IN THE STAIRCASE TEST

Effect of Dexanabinol Analogs on Infarct size in the Transient Middle Cerebral Artery Occlusion (MCAo) Assay Reduction of Necrotic Area in Dexanabinol Derivative-treated Rats Prior to Myocardial Insult

C

D

NON-PSYCHOTROPIC CANNABINOIDS

CROSS-REFERENCE TO RELATED APPLICATIONS

This application is a continuation-in-part of U.S. patent application Ser. No. 10/304,074 filed Nov. 26, 2002, now U.S. Pat. No. 6,610,737 which is a continuation of International Application PCT/IL01/00571 filed Jun. 22, 2001, which, in turn, claims priority to U.S. provisional application No. 60/222,467 filed Jul. 28, 2000.

FIELD OF THE INVENTION

The present invention relates to a family of novel non-psychotropic cannabinoids, and to pharmaceutical compositions containing them, which are useful for preventing or alleviating neurotoxicity and inflammation. Said pharmaceutical compositions comprise as their active ingredient the stereospecific (+) enantiomers, having (3S, 4S) configuration, of $\Delta^6$-tetrahydrocannabinol (THC) type compounds of general formula (I), as defined hereinbelow.

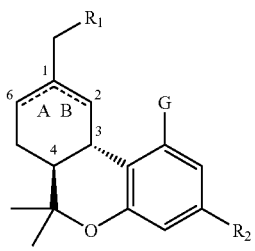

BACKGROUND OF THE INVENTION

The identification of tetrahydrocannabinol (THC) as the active principle of marijuana (*Cannabis sativa*) prompted medicinal chemists to develop numerous cannabinoid analogs (reviewed by Barth, in *Exp. Opin. Ther. Patents* 8:301–313, 1998). These novel compounds were designed to exhibit the beneficial properties of THC without the accompanying psychotropic effects, which limit its therapeutic utility. Potential therapeutic applications have classically included known attributes of marijuana itself such as antiemesis, analgesia, antiglaucoma and appetite stimulation. More recently recognized roles for non-psychotropic cannabinoids are as neuroprotective and anti-inflammatory agents.

Neuroprotective Activity

Chronic degenerative changes, as well as delayed or secondary neuronal damage following direct injury to the central nervous system (CNS), may result from pathologic changes in the brain's endogenous neurochemical systems. Although the precise mechanisms mediating secondary damage are poorly understood, post-traumatic neurochemical changes may include overactivation of neurotransmitter release or re-uptake, changes in presynaptic or postsynaptic receptor binding, or the pathologic release or synthesis of endogenous factors. The identification and characterization of these factors and of the timing of the neurochemical cascade after CNS injury provides a window of opportunity for treatment with pharmacologic agents that modify synthesis, release, receptor binding, or physiologic activity with subsequent attenuation of neuronal damage and improvement in outcome. A number of studies have suggested that modification of post-injury events through pharmacologic intervention can promote functional recovery in both a variety of animal models and clinical CNS injury. Pharmacologic manipulation of endogenous systems by such diverse pharmacologic agents as anticholinergics, excitatory amino acid antagonists, including specifically NMDA receptor antagonists, endogenous opioid antagonists, catecholamines, serotonin antagonists, modulators of arachidonic acid, antioxidants and free radical scavengers, steroid and lipid peroxidation inhibitors, platelet activating factor antagonists, anion exchange inhibitors, magnesium, gangliosides, and calcium channel antagonists have all been suggested to potentially improve functional outcome after brain injury (Mcintosh, *J. Neurotrauma* 10:215–243, 1993).

The pathogenesis of a diverse group of neurological disorders has been linked to excessive activation of excitatory amino acid receptors. These disorders include epilepsy, focal and global ischemia, CNS trauma, and various forms of neurodegeneration including Huntington's chorea, Parkinson's disease and Alzheimer's disease. There has been extensive effort invested in the development of excitatory amino acid receptor antagonists as therapeutic agents (Rogawski, *Trends in Pharmacol. Sci.* 14:325–331,1993 and Danbolt, *Progress in Neurobiology* 65:1–105, 2001).

Since no proven effective therapy for neuronal injury, or degeneration, is yet known, and, for example, stroke alone is one of the leading causes of death in many countries, the importance of finding such therapeutic NMDA antagonists is self-evident. It will be important to determine whether certain NMDA receptor antagonists are more effective—or have fewer side effects—than others in specific disease states.

Some of the compounds of general Formula (I) are disclosed in U.S. Pat. Nos. 4,179,517 and 4,876,276. As disclosed in said U.S. patents, these essentially pure synthetic (+)-(3S,4S)-THC derivatives and analogues are devoid of any undesired cannabimimetic psychotropic side effects. These known compounds have been described as having analgesic, antiemetic and antiglaucoma activity.

A particular compound of interest of Formula I, namely 1,1 dimethyl heptyl-(3S,4S)-7-hydroxy-$\Delta^6$-tetrahydrocannabinol, is disclosed in U.S. Pat. No. 4,876,276, and denoted therein as HU-211, and subsequently assigned the trivial chemical name dexanabinol. HU-211 was unexpectedly discovered to possess neuroprotective attributes, which may be ascribed to its activity as a non-competitive antagonist at the NMDA receptor, as disclosed in U.S. Pat. Nos. 5,284,867 and 5,521,215. Certain ester derivatives of dexanabinol are also active in neuroprotection, as disclosed in U.S. Pat. No. 6,096,740 as are the carboxylic acid derivatives of HU-211 as disclosed in U.S. Pat. Nos. 5,538,993 and 5,635,530.

Anti-Inflammatory Activity

Besides NMDA receptor blocking activity, dexanabinol and its ester derivatives were further shown to possess anti-oxidative and anti-inflammatory properties, which may contribute to their efficacy in preventing or alleviating ischemic damage to tissues.

In addition, derivatives of HU-211 were surprisingly shown to possess immunomodulatory potential due to their ability to inhibit Tumor Necrosis Factor alpha as disclosed in U.S. Pat. No. 5,932,610.

Certain natural non-psychotropic cannabinoids, including the derivative cannabidiol, have been found to have antioxidant properties unrelated to NMDA receptor antagonism as disclosed in WO 99/53917.

Endogenous ligands of the cannabinoid receptors (Mechoulam, et al., Endocannabinoids, *Eur. J. Pharmacol.* 359:1–18,1998) have been identified as being arachidonyl derivatives including 2-arachidonyl glycerol, and arachidonyl-ethanolamide (anandamide). Thus, these endocannabinoids are chemically related to certain metabolites in the arachidonic acid pathway.

A family of compounds known to exhibit inflammatory properties is the prostaglandins (PG). Prostaglandins are arachidonic acid metabolites, produced by the action of cyclooxygenase (COX) also known as PGH synthase. The first step in the production of prostaglandins from arachidonic acid (AA) is the bis-oxygenation of arachidonic acid to prostaglandin $PGG_2$. This is followed by reduction to $PGH_2$ in a peroxidase reaction. COX catalyzes both of these reactions. Two isoforms of COX have been identified, COX-1 and COX-2. Although both perform the same catalytic activity they differ in tissue distribution, regulation and expression (Williams and DuBois *Am J Physiol.* 270: G393–400, 1996).

COX-1 is constitutively expressed and appears to be involved in the physiological production of PGs. Although COX-2 has a normal pattern of expression in some body tissues it is primarily an inducible form that is expressed upon prolonged exposure to chemical mediators including cytokines and endotoxin (reviewed in Golden and Abramson, Selective Cyclooxygenase-2 inhibitors, *Osteoarthritis* 25:359–378,1999) Pain and inflammation in certain pathological processes are mediated by the COX-2 dependent production of $PGE_2$. There is considerable interest in developing anti-inflammatory therapeutic strategies that block the activity of COX-2 and the biosynthesis of $PGE_2$ resulting from activation of the Arachidonic acid/prostaglandin (AA/PG) biosynthetic pathway.

Attenuation of COX-2 activity is correlated with a reduction in pain, inflammation and fever. For example, the NSAIDs (non-steroidal anti-inflammatory drugs) act by blocking the COX enzymes. A reduction of 40–50% in the colon cancer rate among cardiovascular patients in the US who are given prophylactic doses of aspirin (a common NSAID) was also shown to be related to a decrease in COX-2 expression (Smalley and DuBois, *Adv Pharmacol* 39:1–20, 1997).

Therapeutic strategies that target this pathway are sought to prevent and treat a variety of diseases and symptoms such as neuronal degeneration in diseases as Alzheimer's disease or Parkinson's disease, neuronal trauma associated with seizures, brain or CNS damage, inflammation associated with rheumatoid arthritis; bone resorption and colonic polyposis and colorectal cancer (reviewed in Lipsky, *J Rheumatol* 26: Suppl 56:25–30, 1999). U.S. Pat. No. 5,840,746 teaches the method of treating neurodegenerative disease by administering non-steroidal COX-2 inhibitors that specifically bind to COX-2. Inflammation has also been implicated as part of the pathogenesis in myocardial infarction, atheroma, unstable angina and other cardiac disorders (Ross, *New England J Med* 340:115–126, 1999).

There is an unmet need for and it would be advantageous to have novel non-psychotropic cannabinoid compounds that exert their effects via a plurality of mechanisms. Ideally, in addition to having said analgesic, antiemetic and antiglaucoma activities, they would also be effective against the diseases and conditions mentioned above. The mechanisms invoked in these pleitropic effects include their action as excitatory amino acid receptor blockers, for example NMDA-receptor or glutamate-blockers or interaction with the glycine receptor, or as inhibitors of either the oxidative, cytokine, nitric oxide or AA/PG pathways, including the cyclooxygenase and lipoxygenase and are effective in the alleviation and treatment of many of the abnormal states involving said neurotransmitter or pathway mediated toxicity. The present invention now provides such compounds.

SUMMARY OF THE INVENTION

The present invention relates to pharmacologically acceptable non-psychotropic cannabinoids. These compounds act as agents that can afford neuroprotection by exhibiting anti-inflammatory activity, and/or antioxidative activity, and/or the capacity to block the AA/PG or lipoxygenase pathway, or the nitric oxide or cytokine pathways and/or to block excitatory amino acid mediated toxicity by interaction at specific receptors, such as glutamate receptors. In addition, the present provides agents that can afford neuroprotection by combined anti-inflammatory, antioxidative and/or glutamate-receptor blocking mechanisms of action. Thus, the present invention provides pharmaceutical compositions comprising as an active ingredient one of the non-psychotropic cannabinoids disclosed herein. These compositions are useful for the treatment or prevention of ischemia in the CNS as well as in other tissues such as kidney, lung, liver, heart and joints. The compositions will be neuroprotective and will be useful for the prevention or treatment of neurodegenerative disease as well as for glaucoma, pain, inflammation, and emesis.

The present invention discloses novel compounds that are effective in the alleviation and treatment of many of the abnormal states involving inflammation and toxicity. It will be noted that the compounds of the present invention may operate via diverse mechanisms to provide the neuroprotective and/or anti-inflammatory properties.

Certain embodiments of the present invention are particularly effective in alleviating and even preventing neurotoxicity due to excitatory amino acids, also referred to as glutamate neurotoxicity. Glutamate neurotoxicity may occur during acute injuries to the central nervous system (CNS), such as injuries due to prolonged seizures, compromised or reduced blood supply, deprivation of glucose supply and mechanical trauma. The present compositions are also effective in alleviating other damages to the CNS like damage resulting from poison-induced convulsions, including but not limited to those considered to be associated with amino acid receptors other than that of glutamate, for example glycine. Unexpectedly, neuroprotection is also a feature of some of the novel compounds that do not have a high affinity for the NMDA receptor.

Certain embodiments of the present invention are particularly effective in preventing, alleviating or treating tolerance, dependence or abuse of drugs such as opioids, cocaine, psychostimulants or alcohol.

The compositions of the present invention may also be effective in the treatment of certain chronic degenerative diseases that are characterized by gradual selective neuronal loss. In this connection, the compositions of the present invention are contemplated as therapeutically effective in the treatment of Alzheimer's disease, Parkinson's disease, Huntington's disease and amyotrophic lateral sclerosis. Surprisingly, it has been shown experimentally that more preferred embodiments of this group of compounds can even promote nerve regeneration.

The present compositions are of special value in global hypoxic ischemic insults, in hypoxia, alone or in combination with blood flow reduction, such as cardiac, unstable myocardial, renal and hepatic ischemias, as well as in cases of cardiac arrest and in cases of abrupt occlusion of cerebral arteries (stroke).

The present compositions are also particularly useful as analgesics, a generally known attribute of this class of compounds. The present compositions are also of special value in inflammatory or immune diseases of 1) the nervous system, exemplified by multiple sclerosis and other autoimmune diseases, arthritis such as rheumatoid arthritis and other types of local or general inflammation, encephalitis and HIV-induced neurodegeneration; 2) the cardiovascular system, exemplified by myocardial infarction, coronary heart disease, restenosis of coronary vessels and myocarditis; and 3) the pulmonary system, exemplified by asthma or chronic obstructive pulmonary disease (COPD).

The invention also provides compositions that can inhibit the AA/PG signaling pathways that regulate or are regulated by COX-2, an example being the prevention or treatment of the occurrence or growth of gastrointestinal tumors such as colorectal cancer and colonic polyps.

The therapeutic agents of the present invention comprise novel derivatives of non-psychotropic cannabinoids.

A first embodiment of the present invention provides novel compounds according to formula (I):

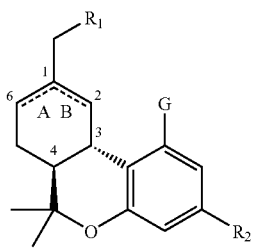

having the (3S,4S) configuration and being essentially free of the (3R,4R) enantiomer, wherein A—B indicates an optional 1(2) or 6(1) double bond, $R_1$ is A) $R_3$ where $R_3$ is selected from the group consisting of
  a) a linear or branched, saturated or unsaturated, carbon side chain comprising 1–8 carbon atoms interrupted by 1–3 heteroatoms; or
  b) a saturated or unsaturated cyclic moiety or an aromatic or heterocyclic moiety having from 5–20 atoms comprising one or two-ringed structures, wherein each ring comprises 3–8 carbons interrupted by 0–4 heteroatoms, said heteroatoms each independently selected from the group consisting of N, O, and S; wherein each ring optionally is further substituted with one or more groups selected from
    i) $C_{1-6}$ alkyl,
    ii) $C_{1-6}$ alkoxy,
    iii) $C_{1-6}$ alkylthio,
    iv) halo,
    v) carboxyl,
    vi) —$CO_2$—$C_{1-4}$ alkyl,
    vii) keto,
    viii) nitro,
    ix) a saturated or unsaturated cyclic moiety, or an aromatic or a heterocyclic moiety comprising one or two ringed structures, wherein each ring comprises 3–8 carbons interrupted by 0–4 heteroatoms, said heteroatoms each independently selected from the group consisting of N, O, and S; wherein each ring optionally is further substituted with one or more groups selected from i)-viii) as defined above;

B) an amine or an amide substituted with at least one substituent as defined in $R_3$ above;

C) a thiol, a sulfide, a sulfoxide, a sulfone, a thioester or a thioamide optionally substituted with one substituent as defined in $R_3$ above; or D) an ether —$OR_3$ wherein $R_3$ is as defined above;

G is (a) halogen, (b) $C_1$–$C_6$ alkyl, or (c) —OR wherein R is (a') —R", wherein R" is hydrogen or $C_1$–$C_6$ alkyl optionally containing a terminal —OR''' or —OC(O)R''' moiety wherein R''' is hydrogen or $C_1$–$C_6$ alkyl, or (b') —C(O)R''' wherein R''' is as previously defined, and $R_2$ is (a) $C_1$–$C_{12}$ alkyl, (b) —OR'''', in which R'''' is a straight chain or branched $C_2$–$C_9$ alkyl which may be substituted at the terminal carbon atom by a phenyl group, or (c) —$(CH_2)_n OR'''$ wherein n is an integer of 1 to 7 and R''' is hydrogen or $C_1$–$C_6$ alkyl;

with the proviso that $R_1$ is other than a heterocyclic moiety having a labile hydrogen atom so that said moiety acts as a carboxylic acid analogue.

For purposes of this specification $C_{1-6}$ alkyl, $C_{1-6}$ alkoxy and $C_{1-6}$ alkylthio are intended to include saturated and unsaturated linear, branched and cyclic structures.

Currently more preferred compounds are those wherein G is hydroxy or lower acyloxy and wherein $R_2$ is dimethylheptyl.

The present invention further relates to pharmaceutical compositions for the purposes set out above, comprising as an active ingredient a compound of the general formula (I):

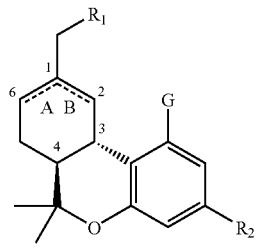

having the (3S,4S) configuration and being essentially free of the (3R,4R) enantiomer, wherein A—B indicates an optional 1(2) or 6(1) double bond, $R_1$ is A) $R_3$ where $R_3$ is selected from the group consisting of
  a) a linear or branched, saturated or unsaturated, carbon side chain comprising 1–8 carbon atoms interrupted by 1–3 heteroatoms; or
  b) a saturated or unsaturated cyclic moiety or an aromatic or heterocyclic moiety having from 5–20 atoms comprising one or two-ringed structures, wherein each ring comprises 3–8 carbons interrupted by 0–4 heteroatoms, said heteroatoms each independently selected from the group consisting of N, O, and S; wherein each ring optionally is further substituted with one or more groups selected from
    i) $C_{1-6}$ alkyl,
    ii) $C_{1-6}$ alkoxy,
    iii) $C_{1-6}$ alkylthio,
    iv) halo,
    v) carboxyl, vi) —$CO_2$—$C_{1-4}$ alkyl,
vii) keto,
viii) nitro,
ix) a saturated or unsaturated cyclic moiety, or an aromatic or a heterocyclic moiety comprising one or two ringed structures, wherein each ring comprises 3–8 carbons interrupted by 0–4 heteroatoms, said heteroatoms each independently selected from the group consisting of N, O, and S; wherein each ring optionally is further substituted with one or more groups selected from i)-viii) as defined above;

B) an amine or an amide substituted with at least one substituent as defined in $R_3$ above;

C) a thiol, a sulfide, a sulfoxide, a sulfone, a thioester or a thioamide optionally substituted with one substituent as defined in $R_3$ above; or D) an ether —$OR_3$ wherein $R_3$ is as defined above;

G is (a) halogen, (b) $C_1$–$C_6$ alkyl, or (c) —OR wherein R is (a') —R", wherein R" is hydrogen or $C_1$–$C_6$ alkyl optionally containing a terminal —OR'" or —OC(O)R'" moiety wherein R'" is hydrogen or $C_1$–$C_6$ alkyl, or (b') —C(O)R'" wherein R'" is as previously defined, and $R_2$ is (a) $C_1$–$C_{12}$ alkyl, (b) —OR"", in which R"" is a straight chain or branched $C_2$–$C_9$ alkyl which may be substituted at the terminal carbon atom by a phenyl group, or (c) —$(CH_2)_n$OR'" wherein n is an integer of 1 to 7 and R'" is hydrogen or $C_1$–$C_6$ alkyl;

with the proviso that $R_1$ is other than a heterocyclic moiety having a labile hydrogen atom so that said moiety acts as a carboxylic acid analogue.

For purposes of this specification $C_{1-6}$ alkyl, $C_{1-6}$ alkoxy and $C_{1-6}$ alkylthio are intended to include saturated and unsaturated linear, branched and cyclic structures.

Currently more preferred compounds are those wherein G is hydroxy or lower acyloxy and wherein $R_2$ is dimethylheptyl.

According to currently preferred embodiments of the present invention $R_1$ is a heterocyclic moiety selected from the group consisting of an imidazolyl, an imidazolinyl, a morpholino, a piperidyl, a piperazinyl, a pyrazolyl, a pyrrolyl, a pyrrolidinyl, a triazolyl, and a tetrazolyl.

According to further currently preferred embodiments of the present invention $R_1$ is a heterocyclic moiety selected from the group consisting of an imidazolyl, an imidazolinyl, a morpholino, a piperidyl, a piperazinyl, a pyrazolyl, a pyrrolyl, a pyrrolidinyl, a triazolyl, and a tetrazolyl, optionally further substituted wherein the substituent is selected from the group consisting of $C_{1-6}$ alkyl, $C_{1-6}$ alkyloxy, $C_{1-6}$ alkylthio, keto, carboxy, nitro, saturated or unsaturated cyclic moieties or aromatic or heterocyclic moieties wherein each ring comprises 3–8 carbons interrupted by 0–4 heteroatoms, said heteroatoms each independently selected from the group consisting of N, O, and S, wherein each ring optionally is further substituted with one or more groups selected from the group consisting of $C_{1-6}$ alkyl, $C_{1-6}$ alkyloxy, $C_{1-6}$ alkylthio, keto, carboxy, or nitro.

According to more preferred embodiments of the present invention $R_1$ is selected from the group consisting of imidazole, pyrazole, oxazole, isoxazole, tetrahydropyridine, pyrazoline, oxazoline, pyrrolidine, imidazoline, 2-thio-imidazole, 2-methylthio-imidazoline, 4-methyl-2-imidazoline, 4,4-dimethyl-2-imidazoline, methyl sulfide, methylsulfoxide, acetamido, benzamide, cyano, 1,2,4-triazole, 1,3,4-triazole, 1,2,3,4-tetrazole, 1,2,3,5-tetrazole, thiophene, phenyl, morpholine, thiomorpholine, thiazolidine, glycerol, piperazine, and tetrahydropyran.

According to additional more preferred embodiments of the present invention $R_1$ is selected from the group consisting of mono or di-substituted amines wherein the substituent is selected from the group consisting of an $C_{1-6}$ alkyl, $C_{1-6}$ alkyloxy, $C_{1-6}$ alkylthio, imidazolyl, an imidazolinyl, a morpholino, a piperidyl, a piperazinyl, a pyrazolyl, a pyrrolyl, a pyrrolidinyl, a triazolyl, and a tetrazolyl, optionally further substituted wherein the substituent is selected from the group consisting of $C_{1-6}$ alkyl, $C_{1-6}$ alkyloxy, $C_{1-6}$ alkylthio, keto, carboxy, or nitro, wherein $C_{1-6}$ alkyl, $C_{1-6}$ alkoxy and $C_{1-6}$ alkylthio are intended to include saturated and unsaturated linear, branched and cyclic structures.

The invention further relates to methods of treatment comprising administering to a patient in need thereof, of a therapeutically effective amount of a composition comprising a compound according to the present invention.

It has been discovered that certain novel compounds of formula (I) are dexanabinol derivatives wherein $R_1$ is a heterocyclic moiety. These compounds are preferred active agents of the presently claimed compositions for exhibiting efficient anti-inflammatory properties, including inhibition of prostaglandin synthesis, as well as inhibition of tumor necrosis factor production, and inhibition of nitric oxide production, in addition to providing NMDA receptor blocking and anti-oxidative activity.

It has also been discovered, unexpectedly, that certain novel compounds of formula (I) are dexanabinol derivatives wherein $R_1$ is a substituted amine as defined above. These compounds are preferred active agents of the presently claimed compositions for exhibiting efficient anti-inflammatory properties, including inhibition of prostaglandin synthesis, as well as inhibition of tumor necrosis factor production, and inhibition of nitric oxide production, while being inactive or relatively inactive as NMDA receptor blockers.

DETAILED DESCRIPTION OF THE PREFERRED EMBODIMENTS

Figure 1:
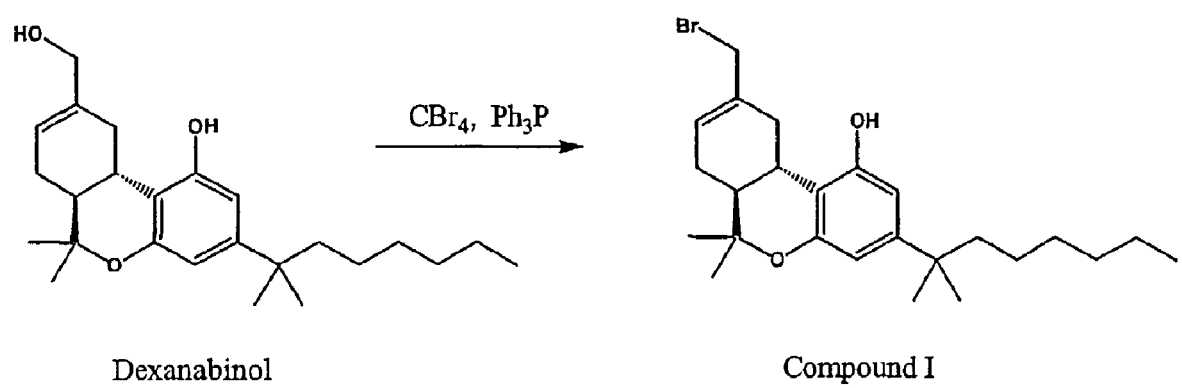
FIG. 1 depicts the synthetic scheme used to synthesize certain preferred compounds designated PRS-211, using dexanabinol as the starting material.
Figure 1:
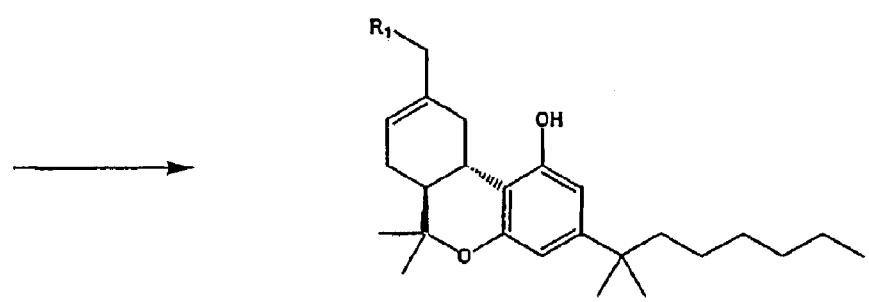

The present invention provides novel compounds belonging to the class of non-psychotropic cannabinoids, as well as pharmaceutical compositions comprising these compounds, and methods of using such compounds. Compounds of this class are effective agents for the treatment and prevention of emesis, glaucoma and pain and have been shown to possess neuroprotective and anti-inflammatory properties. It is explicit that the present invention excludes known compounds disclosed in U.S. Pat. Nos. 4,876,276, 5,538,993, 5,635,530 and 6,096,740.

The compositions of the present invention are effective to reduce or even prevent neurological damage, including but not limited to excitatory amino acid neurotoxicity, due to acute injury or poisoning of the CNS, such as injuries due to prolonged seizures, compromised or reduced blood supply, deprivation of glucose supply and mechanical trauma, and poisonings by, for example, strychnine, picrotoxin or organophosphorous compounds.

The compositions of the present invention may also be effective in treating certain chronic degenerative diseases that are characterized by gradual selective neuronal loss. In this connection, the compositions of the present invention are contemplated as therapeutically effective in the treatment of Huntington's chorea, amyotrophic lateral sclerosis, Parkinson's disease and Alzheimer's disease, via mechanisms of neuroprotection and/or nerve regeneration.

As stated above, the present compositions are of special value in seizures, global hypoxic ischemic insults, in hypoxia, alone or in combination with blood flow reduction (ischemia such as cardiac, unstable myocardial, pulmonary, renal and hepatic ischemias) as well as in cases of cardiac arrest and in cases of abrupt occlusion of cerebral arteries (stroke).

The compositions of the present invention are neuroprotective and may exert their neuroprotective actions through multiple mechanisms including, but not limited to anti-inflammatory and/or antioxidative mechanisms, and some of them are particularly effective in alleviating and even preventing glutamate neurotoxicity due to acute injuries to the central nervous system (CNS), such as injuries due to prolonged seizures, compromised or reduced blood supply, deprivation of glucose supply and mechanical trauma. The present compositions are also effective in alleviating other damages to the CNS like poison-induced convulsions, considered to be associated with amino acid receptors other than that of glutamate, for example glycine.

The compositions of the present invention are also effective in the treatment or prevention of pain, including chronic pain and neuropathic pain.

By virtue of their anti-inflammatory properties it will be recognized that the compositions according to the present invention will be useful in a wide variety of additional indications having an inflammatory or autoimmune mechanism involved in their etiology or pathogenesis exemplified by multiple sclerosis, arthritis such as rheumatoid arthritis and other types of local/general inflammation, encephalitis and HIV-induced neurodegeneration.

Another feature of the present invention is its ability to prevent or treat the occurrence or growth of gastrointestinal tumors such as colorectal cancer and colonic polyposis.

A set of the pharmaceutical compositions of the present invention exhibit inhibitory activity on NOS and cytokines as well as the AA/PG signaling pathways that regulate or are regulated by COX-2. The therapeutic agents of the present invention comprise novel derivatives of non-psychotropic cannabinoids.

Cannabis is known for its analgesic properties. It shares this activity with other plants and preparations of papaver somniferum have also been used to relieve pain long before the main opioid constituent morphine was isolated. Similarly to cannabinoids, the opioids exert their effect through interaction with specific G-protein coupled receptors bearing seven transmembrane domains. Reports indicate that cannabinoids and opioids system interact and may by yet unclear mechanisms potentiate one another.

The beneficial therapeutic effects of opioids such as analgesia, are being clinically hindered by their undesirable side effects including depression of respiration, inhibition of intestinal motility, nausea and vomiting and effects on mood. The most notorious drawback to opioid utilization for therapeutical purposes is the development of tolerance and physical dependence. Tolerance represents a need to increase the opioid dose to achieve the same effect or it represents a diminished effect for the same dose of opioid over time. Opioid analogs were prepared to specifically isolate the desirable clinical effect with varying degrees of success. Another solution to the problem of tolerance and dependence was reported and it relates to the use of the opioid in combination with compounds such as NMDA antagonists, nitric oxide inhibitors and cyclooxygenase inhibitors.

In addition to preventing tolerance and dependence to opioids, NMDA antagonists were reported to interfere with the development, maintenance and expression of pathophysiological processes common to all drugs of abuse including cocaine, psychostimulants, and addiction to alcohol (Bisaga A. et al., Drug and Alcohol Dependence 59: 1–15, 2000). Moreover, NMDA antagonists potentiate the analgesic activity of various substances including but not limited to opioids, non-opioid analgesics, anticonvulsants, NK1 antagonists, local anesthetics, substance P antagonists, cyclooxygenase inhibitors, and nicotinic acetylcholine agonists.

By virtue of their ability to act as NMDA antagonists, nitric oxide inhibitors or cyclooxygenase inhibitors, it will be recognized that the compositions according to the present invention will be useful in a wide variety of additional pathologies wherein such compound have therapeutic benefice including but not limited to reduction or reversal of tolerance or dependence to drugs such as opioids and potentiation of therapeutic activity of other analgesics.

The present invention relates to pharmaceutical compositions for the purposes set out above, in which the active ingredient is a compound of the general formula (I):

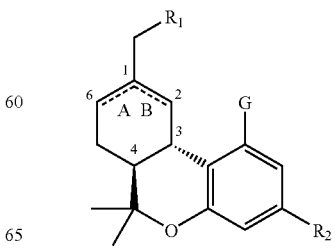

having the (3S,4S) configuration and being essentially free of the (3R,4R) enantiomer, wherein A—B indicates an optional 1(2) or 6(1) double bond, $R_1$ is
A) $R_3$ where $R_3$ is selected from the group consisting of
   a) a linear or branched, saturated or unsaturated, carbon side chain comprising 1–8 carbon atoms interrupted by 1–3 heteroatoms; or
   b) a saturated or unsaturated cyclic moiety or an aromatic or heterocyclic moiety having from 5–20 atoms comprising one or two-ringed structures, wherein each ring comprises 3–8 carbons interrupted by 0–4 heteroatoms, said heteroatoms each independently selected from the group consisting of N, O, and S; wherein each ring optionally is further substituted with one or more groups selected from
      i) $C_{1-6}$ alkyl,
      ii) $C_{1-6}$ alkoxy,
      iii) $C_{1-6}$ alkylthio,
      iv) halo,
      v) carboxyl,
      vi) —$CO_2$—$C_{1-4}$ alkyl,
      vii) keto,
      viii) nitro,
      ix) a saturated or unsaturated cyclic moiety, or an aromatic or a heterocyclic moiety comprising one or two ringed structure, wherein each ring comprises 3–8 carbons interrupted by 0–4 heteroatoms, said heteroatoms each independently selected from the group consisting of N, O, and S; wherein each ring optionally is further substituted with one or more groups selected from i)-viii) as defined above;
B) an amine —$N(R_3)_2$ or an amide —$N(R_3)$—$COR_3$ substituted with at least one substituent as defined in $R_3$ above;
C) a thiol —$R_3SH$, a sulfide —$SR_3$, a sulfoxide —$SOR_3$, a sulfone —$SO_2R_3$, a thioester —$SC(O)R_3$ or a thioamide —$NC(S)R_3$, optionally substituted with one substituent as defined in $R_3$ above; or
D) an ether —$OR_3$ wherein $R_3$ is as defined above;

G is (a) halogen, (b) $C_1$–$C_6$ alkyl, or (c) —OR wherein R is (a') —R", wherein R" is hydrogen or $C_1$–$C_6$ alkyl optionally containing a terminal —OR''' or —OC(O)R''' moiety wherein R''' is hydrogen or $C_1$–$C_6$ alkyl, or (b') —C(O)R''' wherein R''' is as previously defined, and $R_2$ is (a) $C_1$–$C_{12}$ alkyl, (b) —OR'''', in which R'''' is a straight chain or branched $C_2$–$C_9$ alkyl which may be substituted at the terminal carbon atom by a phenyl group, or (c) —$(CH_2)_n OR'''$ wherein n is an integer of 1 to 7 and R''' is hydrogen or $C_1$–$C_6$ alkyl; with the proviso that $R_1$ is other than a heterocyclic moiety having a labile hydrogen atom so that said moiety acts as a carboxylic acid analogue.

For purposes of this specification $C_{1-6}$ alkyl, $C_{1-6}$ alkoxy and $C_{1-6}$ alkylthio are intended to include saturated and unsaturated linear, branched and cyclic structures.

Currently more preferred compounds are those wherein G is hydroxy or lower acyloxy and wherein $R_2$ is dimethylheptyl.

According to preferred embodiments of the present invention $R_1$ is a heterocyclic moiety selected from the group consisting of an imidazolyl, an imidazolinyl, a morpholino, a piperidyl, a piperazinyl, a pyrazolyl, a pyrrolyl, a pyrrolidinyl, a triazolyl, and a tetrazolyl, optionally further substituted wherein the substituent is selected from the group consisting of $C_{1-6}$ alkyl, $C_{1-6}$ alkyloxy, $C_{1-6}$ alkylthio, keto, carboxy or nitro, saturated or unsaturated cyclic moieties or aromatic or heterocyclic moieties wherein each ring comprises 3–8 carbons interrupted by 0–4 heteroatoms, said heteroatoms each independently selected from the group consisting of N, O, and S, wherein each ring optionally is further substituted with one or more groups selected from the group consisting of $C_{1-6}$ alkyl, $C_{1-6}$ alkyloxy, $C_{1-6}$ alkylthio, keto, carboxy, or nitro, wherein $C_{1-6}$ alkyl, $C_{1-6}$ alkoxy and $C_{1-6}$ alkylthio are intended to include saturated and unsaturated linear, branched and cyclic structures.

According to more preferred embodiments of the present invention $R_1$ is selected from the group consisting of imidazole, pyrazole, oxazole, isoxazole, tetrahydropyridine, pyrazoline, oxazoline, pyrrolidine, imidazoline, 2-thio-imidazole, 2-methylthio-imidazoline, 4-methyl-2-imidazoline, 4,4-dimethyl-2-imidazoline, methyl sulfide, methylsulfoxide, acetamido, benzamide, cyano, 1,2,4-triazole, 1,3,4-triazole, 1,2,3,4-tetrazole, 1,2,3,5-tetrazole, thiophene, phenyl, morpholine, thiomorpholine, thiazolidine, glycerol, piperazine, 4-piperidinopiperidine, 4-methylpiperidine and tetrahydropyran.

According to additional more preferred embodiments of the present invention $R_1$ is selected from the group consisting of mono or di-substituted amines wherein the substituent is selected from the group consisting of $C_{1-6}$ alkyl, $C_{1-6}$ alkyloxy, $C_{1-6}$ alkylthio, imidazolyl, an imidazolinyl, a morpholino, a piperidyl, a piperazinyl, a pyrazolyl, a pyrrolyl, a pyrrolidinyl, a triazolyl, and a tetrazolyl, wherein each cyclic structure may optionally be further substituted with at least one substituent selected from the group consisting of $C_{1-6}$ alkyl, $C_{1-6}$ alkyloxy, $C_{1-6}$ alkylthio, keto, carboxy, or nitro, wherein $C_{1-6}$ alkyl, $C_{1-6}$ alkoxy and $C_{1-6}$ alkylthio are intended to include saturated and unsaturated linear, branched and cyclic structures.

In a currently preferred group of compounds, $R_2$ designates a 1,1-dimethylalkyl radical or a 1,2-dimethylalkyl radical with a total of at least 7 carbon atoms. Also preferred are precursors of such compounds. Particularly preferred compounds are those wherein $R_2$ is 1,1-dimethylheptyl or 1,2-dimethylheptyl. It is these embodiments of $R_2$ that are found in THC and its analogues. However, for the neuroprotective activity that characterizes the present invention, it is believed that any lower or mid-range alkyl substituent will be suitable at this position.

Throughout this specification, the compounds of the present invention may be referred to by their internal reference numbers rather than by their full chemical names. The prefix for this series of compounds is PRS-211, followed by a three-digit code for each specific compound of the series.

One currently most preferred compound, with which many of the physiological experiments have been carried out, is the compound, which may be referred to as (+)-(3S,4S)-6,6-Dimethyl-(1,1-dimethylheptyl)-1-hydroxy-9-(imidazolomethyl)-6a,7,10,10a-tetrahydro-6H-dibenzo[b,d]pyran. This compound is designated hereinafter as PRS-211, 095.

Another currently most preferred compound, with which many of the physiological experiments have been carried out, is the compound, which may be referred to as (+)-(3S, 4S)-6,6-Dimethyl-(1,1-dimethylheptyl)-1-hydroxy-9-(pyrazolomethyl)-6a,7,10,10a-tetrahydro-6H-dibenzo[b,d]pyran. This compound is designated hereinafter as PRS-211,220.

Another currently most preferred compound, with which many of the physiological experiments have been carried out, is the compound, which may be referred to as (+)-(3S, 4S)-6,6-Dimethyl-(1,1-dimethylheptyl)-1-hydroxy-9-(1H- imidazol-2-ylsulfanyl methyl)-6a,7,10,10a-tetrahydro-6H-dibenzo[b,d]pyran. This compound is designated hereinafter as PRS-211,092.

Another currently most preferred compound, with desirable PGE2 and NOS inhibitory activity, which may be referred to as (+)-(3S,4S)-6,6-Dimethyl-(1,1-dimethylheptyl)-1-hydroxy-9-(4-piperidinopiperidine methyl) 6a,7,10,10a-tetrahydro-6H-dibenzo[b,d]pyran. This compound is designated hereinafter as PRS-211,257.

Another currently most preferred compound, with desirable PGE2 and NOS inhibitory activity, which may be referred to as (+)-(3S,4S)-6,6-Dimethyl-(1,1-dimethylheptyl)-1-hydroxy-9-(4-methylpiperidine methyl)-6a,7,10,10a-tetrahydro-6H-dibenzo[b,d]pyran. This compound is designated hereinafter as PRS-211,251.

It is emphasized that all the compounds are of the (+)-(3S,4S) configuration, essentially free of the (−)-(3R,4R) enantiomer, the latter known to possess the undesired psychotropic side effects. Thus, for example, the enantiomers of the synthetic cannabinoid 7-hydroxy-$\Delta^6$-tetrahydrocannabinol 1,1-dimethylheptyl homolog, have been described [Mechoulam, R., et al., *Tetrahedron: Asymmetry* 1: 315–319, 1990; Mechoulam, R. et al., *Experientia* 44: 762–764, 1988]. The (−)-(3R,4R) enantiomer, herein designated HU-210, is a highly potent cannabimimetic compound (nearly 100 times more active than Δ-1-tetrahydrocannabinol, the active component of hashish). The (+)-(3S,4S) enantiomer, herein designated HU-211, also known by the trivial chemical name dexanabinol, while known to be active as an analgesic and as an anti-emetic, is inactive as a cannabimimetic even at doses several thousand times higher than the $ED_{50}$ of HU-210 (Mechoulam, R. et al., *Experientia* 44: 762–764,1988).

As mentioned above, then, the compounds of the general formula (I) as defined herein are substantially devoid of cannabimimetic central nervous system activity.

All of the compounds of the present invention are stereospecific (+) enantiomers of the naturally occurring (−) cannabinoids. The (+) stereospecificity provides compounds that are devoid of psychotropic activity, and have been shown to have substantially no binding to the cannabinoid receptor CB1 of the central nervous system. The IC50 of binding of these novel compounds to the CB1 receptor is greater than 300 nM, more preferably greater than 1 μM, most preferably greater than 5 μM.

Pharmacology

The novel compositions contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration or for injection, the term including subcutaneous, transdermal, intravenous, intrathecal, and other parenteral routes of administration. The liquid compositions include aqueous solutions, with or without organic cosolvents, aqueous or oil suspensions, flavored emulsions with edible oils, as well as elixirs and similar pharmaceutical vehicles. In addition, the compositions of the present invention may be formed as aerosols, for intranasal and like administration.

The active dose for humans is generally in the range of from 0.05 mg to about 50 mg per kg body weight, in a regimen of 1–4 times a day. However, administration every two days may also be possible, as the drug has a rather prolonged action. The preferred range of dosage is from 0.1 mg to about 20 mg per kg body weight. However, it is evident to the man skilled in the art that dosages would be determined by the attending physician, according to the disease to be treated, method of administration, patient's age, weight, contraindications and the like.

All the compounds defined above are effective as either NMDA-receptor blockers or oxidative or inflammatory pathway inhibitors and can be used as active ingredients of pharmaceutical compositions for treatment of one, or simultaneously several, symptoms of the disorders defined above. The effective dosages are essentially similar, and the more pronounced effect is that of NMDA-receptor blocking, in addition to the known characteristics of these compounds. However, it is important to note that the compounds and compositions of the present invention exhibit good blocking activity also against convulsants that may not necessarily be NMDA-receptor mediators. For example, the compositions of the present invention can prevent, or at least alleviate, poisoning caused by strychnine organophosphorous compounds and nitrous oxide.

The compounds of the present invention are administered for the above-defined purposes in conventional pharmaceutical forms, with the required solvents, diluents, excipients, etc. to produce a physiologically acceptable formulation. They can be administered by any of the conventional routes of administration. The required dose for humans ranges from 0.005 mg/kg to about 50 mg/kg per unit dosage form. The most preferred dose range is from about 0.1 mg/kg to about 20 mg/kg body weight.

It will be appreciated that the most appropriate administration of the pharmaceutical compositions of the present invention will depend on the type of injury or disease being treated. Thus, the treatment of acute head trauma, stroke or ischemic brain damage resulting from cardiac arrest will necessitate systemic administration of the drug as rapidly as possible after induction of the injury. On the other hand, diminution or prophylaxis of chronic degenerative damage, inflammation or gastrointestinal cancer therapy will necessitate a sustained dosage regimen.

PRS-211 compounds convey significant neuroprotection in different in vivo models of head trauma, as well as transient and permanent brain ischemia. This suggests neuroprotective potential in a wide spectrum of CNS diseases, poisonings or injuries, as detailed above, including conditions involving axonal damage such as that sustained in spinal cord injury. PRS-211 compounds are also particularly useful in treating neural edema, associated with trauma, infection, tumors or surgical procedures including craniotomies and spinal cord manipulation.

Moreover, the combined neuroprotective and anti-inflammatory properties of PRS-211 compounds, as well as the known anti-glaucoma properties of this class of compounds, leads to special consideration of retinal eye diseases, especially those which are associated with ischemic damage or a hostile biochemical environment. Some non-limiting examples would be diabetic retinopathy, age-related Macular Degeneration, retinal vascular occlusions that are relatively common and may cause considerable ischemic damage. All retinal occlusions, venous and arterial, including the optic nerve (ischemic optic neuropathy), as well as retinopathy of prematurity (oxygen toxicity in premature babies), may be included in this category, as well as any insult that may lead to secondary neural damage following direct retinal cell death, e.g., trauma, including surgical trauma such as laser burn injuries, inflammations, infections and degenerative processes, chronic ischemic damage, including glaucomatous optic nerve damage and toxic damage (e.g., chloroquine toxicity) and chronic malnutrition.

The inventors have discovered that certain novel compounds of formula (I), which are preferred active agents of the presently claimed compositions, such as PRS-211,092, PRS-211,095, PRS-211,128, PRS-211,132 PRS-211,220, PRS-211,251 and exhibit combined mechanisms of neuroprotection and anti-inflammation, including inhibition of prostaglandin and leukotriene synthesis, as well as the inhibition of nitric oxide synthesis (as measured by the inhibition of nitric oxide synthase (NOS))* and the production of cytokines such as tumor necrosis factor (TNFα) and interleukin-1β, in addition to the NMDA blocking and anti-oxidative activity.

Certain novel compounds of formula (I) such as the majority of the amine derivatives of PRS-211 such as PRS-211,251, PRS-211,253, PRS-211,255 or PRS-211,257 do not exhibit substantial NMDA receptor binding but exert their effect via inhibition of the AA/PG pathway and/or as anti-oxidatives. A tabulation of the more preferred compounds according the present invention, is presented in Table 1, whereas their variegated patterns of activities in terms of NMDA binding, anti-inflammatory and anti oxidative activities is shown in Table 2. These tables include the known compound, HU-211 (dexanabinol) for the sake of comparison.

TABLE 1

Chemical Structures of Novel PRS-211 compounds

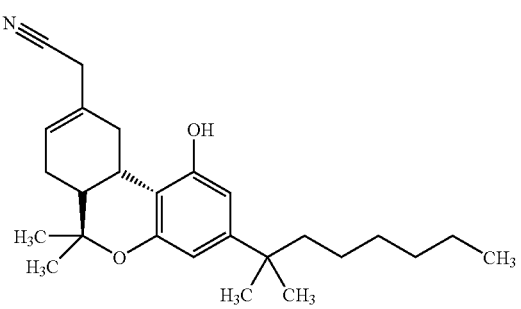

211,006-000

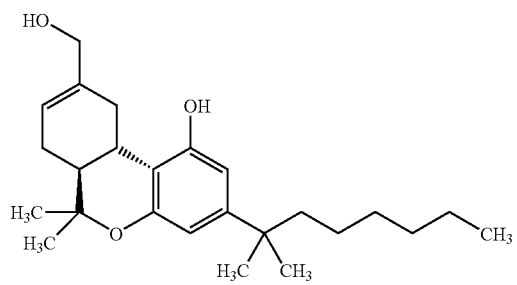

211,007-000
HU-211

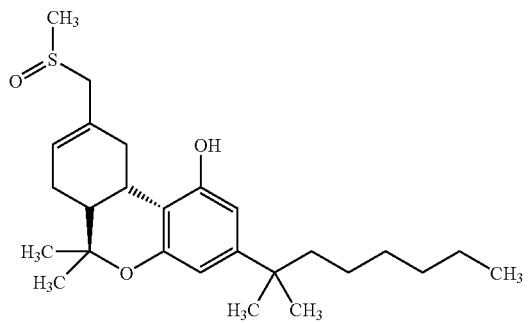

211,041-000

TABLE 1-continued
Chemical Structures of Novel PRS-211 compounds
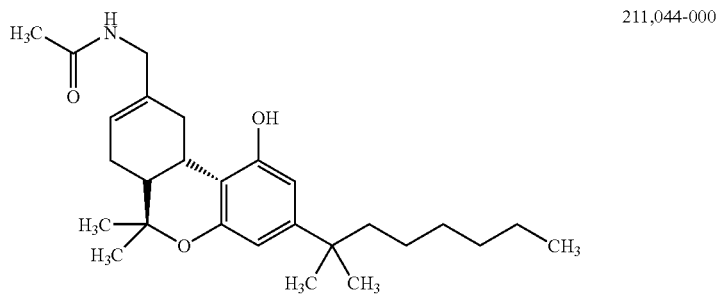
211,044-000
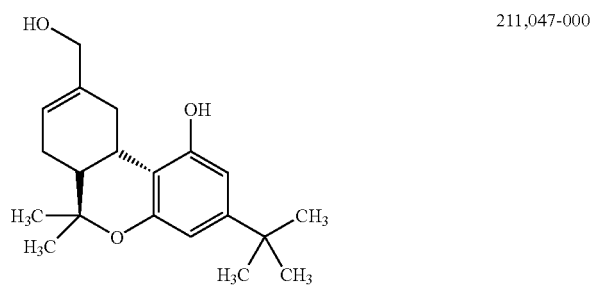
211,047-000
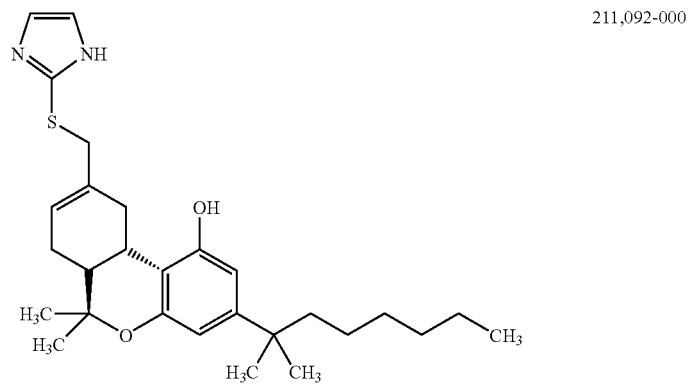
211,092-000
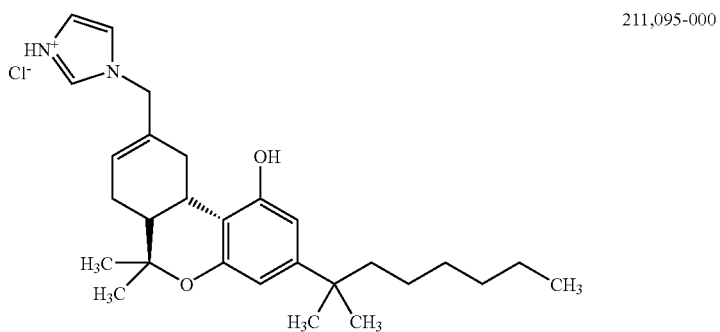
211,095-000

TABLE 1-continued
Chemical Structures of Novel PRS-211 compounds
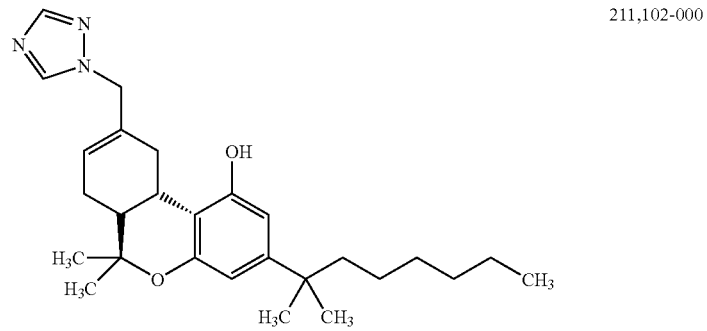
211,102-000
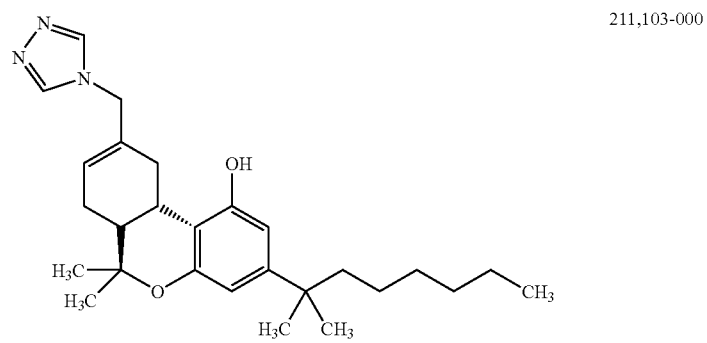
211,103-000
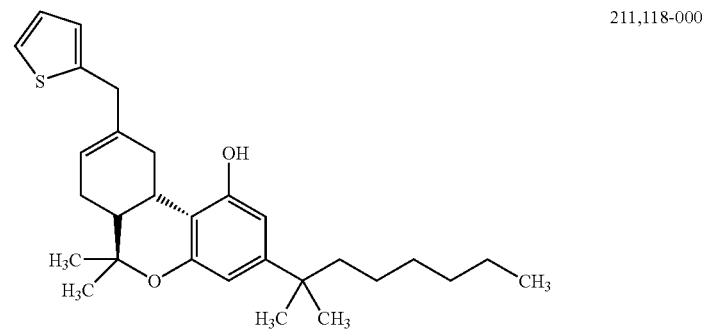
211,118-000
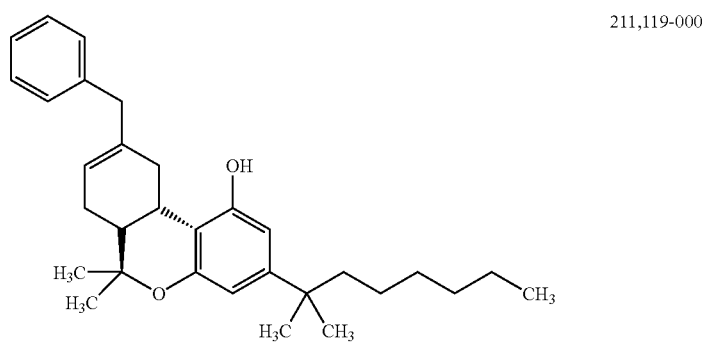
211,119-000

TABLE 1-continued
Chemical Structures of Novel PRS-211 compounds
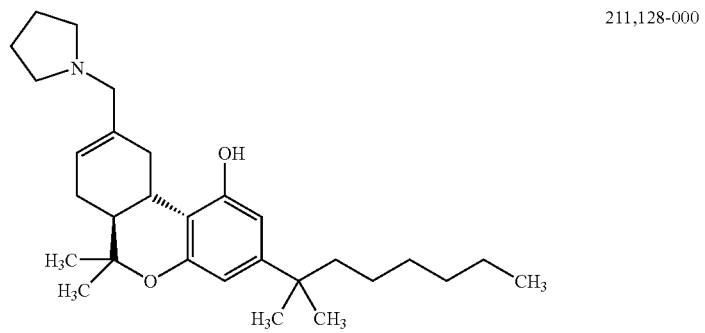
211,128-000
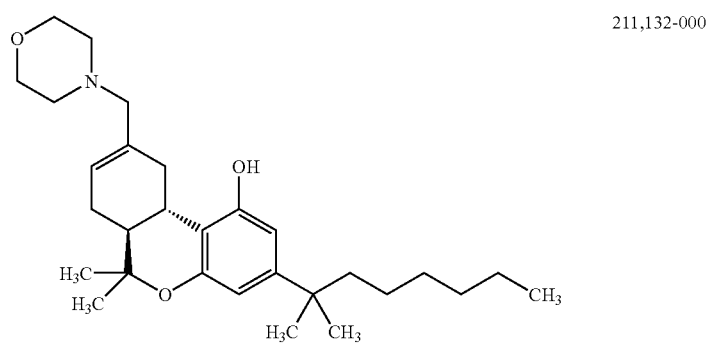
211,132-000
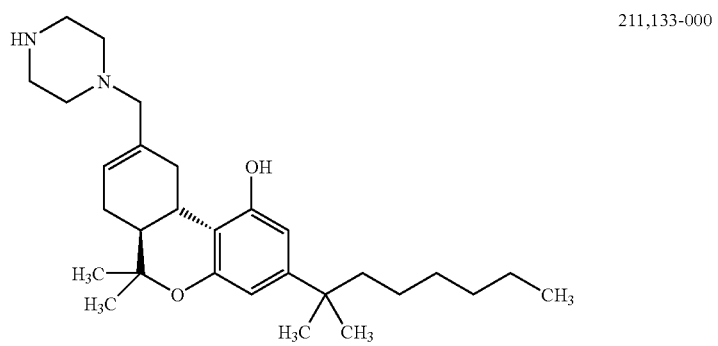
211,133-000
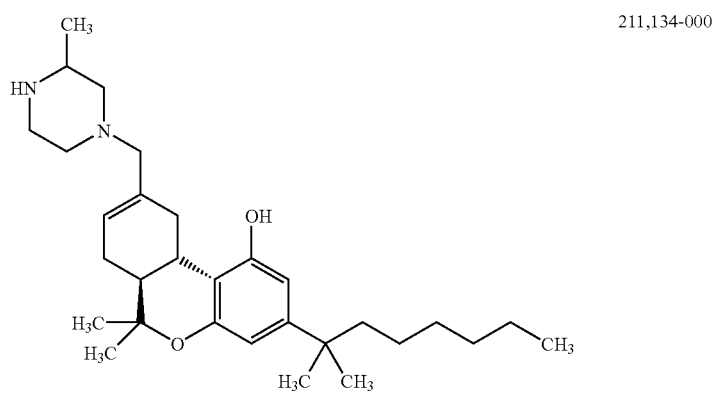
211,134-000

TABLE 1-continued
Chemical Structures of Novel PRS-211 compounds
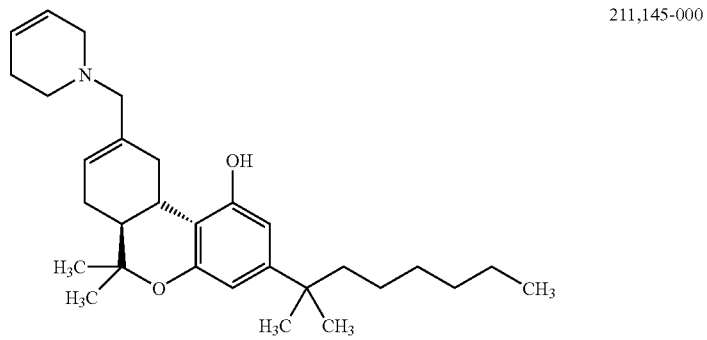
211,145-000
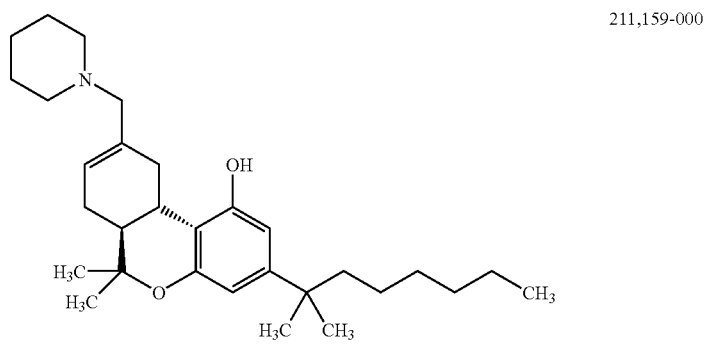
211,159-000
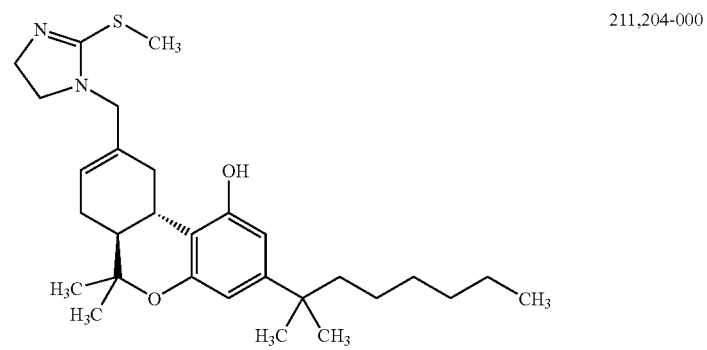
211,204-000
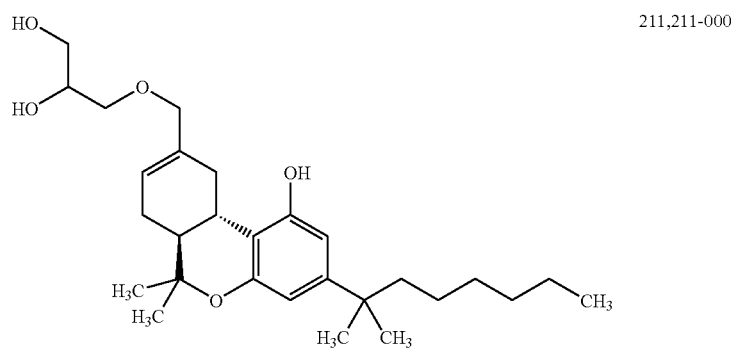
211,211-000

TABLE 1-continued
Chemical Structures of Novel PRS-211 compounds
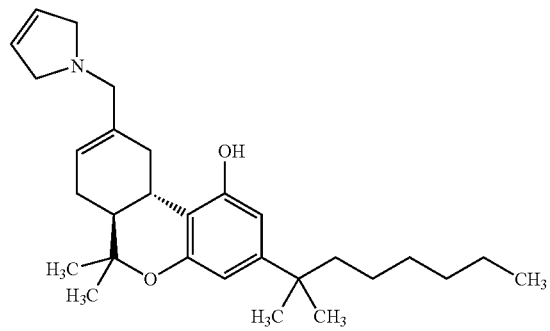
211,212-000
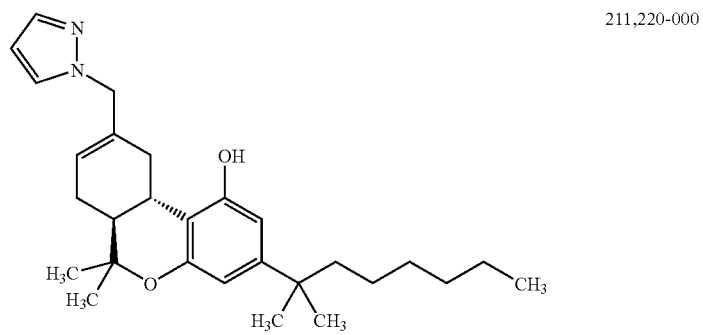
211,220-000
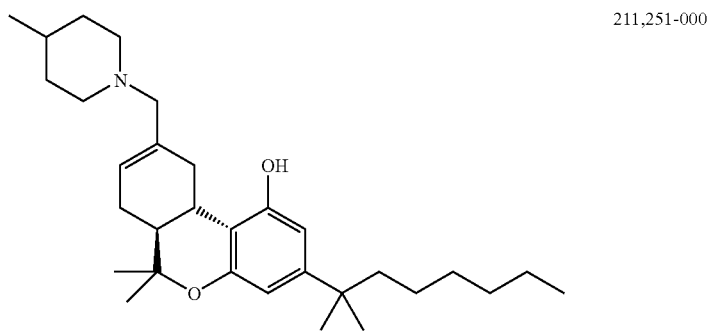
211,251-000
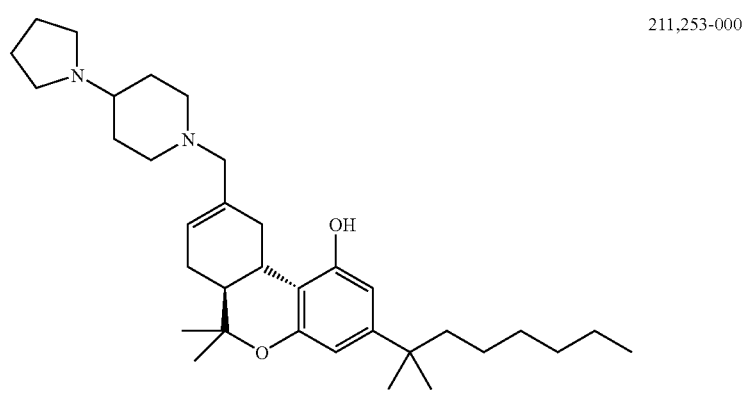
211,253-000

TABLE 1-continued

Chemical Structures of Novel PRS-211 compounds

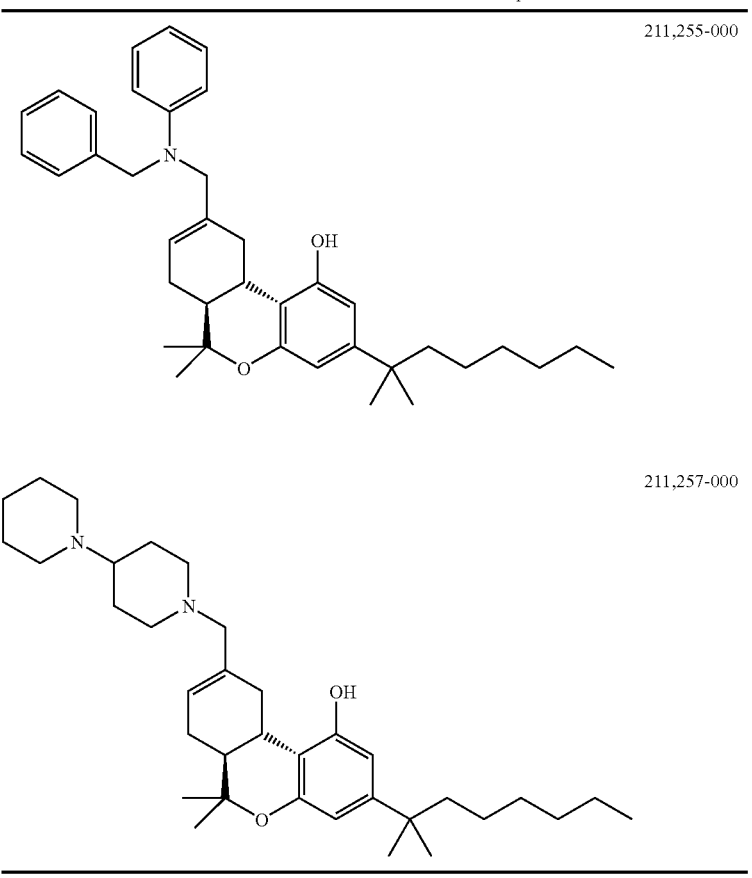

211,255-000

211,257-000

TABLE 2

ACTIVITIES OF PRS-211 COMPOUNDS.

| PRS number | NMDA BINDING IC50 (μM) | PGE2 % inhibition (at 10 μM) | TNFα % inhibition (at 10 μM) | NOS % inhibition (at 10 μM) | Ear Edema ED50 (μmol/kg) CO |
|---|---|---|---|---|---|
| 211,006-000 | 8 | 41 | 46 | 19 | 104 |
| 211,007-000 HU-211 | 10 | 54 | 33 | 20 | 25 |
| 211,041-000 | 6 | 56 | 23 | 72 | 39 |
| 211,044-000 | 6 | 24 | 0 | | |
| 211,047-000 | 100 | 28 | 0 | | |
| 211,092-000 | >50 | 57 | 22 | 86 | 28 |
| 211,095-000 | 2.5 | 72 | 11 | 34 | 29 |
| 211,102-000 | 2.5 | | | | |
| 211,103-000 | 3 | | | | |
| 211,118-000 | 32 | | | | |
| 211,119-000 | 62 | 14 | | 0 | |
| 211,128-000 | >20 | 84 | 48 | 27 | 23 |
| 211,132-000 | 4.5 | 61 | 21 | 40 | 70 |
| 211,133-000 | >100 | | | | |
| 211,134-000 | >100 | | | | |
| 211,145-000 | 13 | 63 | 15 | 60 | |
| 211,159-000 | >20 | 87 | 33 | 27 | |
| 211,204-000 | 10 | 83 | 28 | 85 | 34 |
| 211,211-000 | 4.6 | 83 | 18 | 0 | |
| 211,212-000 | 7.5 | 96 | 14 | 0 | |
| 211,220-000 | 0.35 | 59 | 11 | 24 | 57 |
| 211,251-000 | >100 | 91 | 0 | 37 | |
| 211,253-000 | >100 | 92 | 0 | 27 | |
| 211,255-000 | >100 | 94 | 0 | 7 | |
| 211,257-000 | >100 | 88 | 10 | 39 | |

The invention also relates to methods of treatment of the various pathological conditions described above, by administering to a patient a therapeutically effective amount of the compositions of the present invention. The term administration as used herein encompasses oral, parenteral, intravenous, intramuscular, subcutaneous, transdermal, intrathecal, rectal and intranasal administration.

Binding studies show that certain embodiments of the present invention block NMDA receptors in a stereospecific manner, and that the interaction occurs at binding site(s) distinct from those of some other non-competitive NMDA antagonists or of glutamate and glycine. This, and the other compounds according to formula (I), may therefore prove useful as non-psychoactive drugs that protect against NMDA-receptor-mediated neurotoxicity.

The inhibitory effect of the new derivatives of Dexanabinol on prostaglandin synthesis is evaluated in macrophage cell cultures following LPS exposure to induce the inflammatory response. These assays are an indication of the anti-inflammatory activity of the individual analogs.

(c) Inhibition of Tumor Necrosis Factor Alpha:

Specific aspects of the inflammatory response cascade are mediated by the cytokine TNFα. Inhibition of TNFα production and/or inhibition of TNFα release by the new analogs are assayed in macrophage cell cultures activated with LPS. This serves as another indication of the general anti-inflammatory potential of the novel compounds.

(d) Nitric Oxide Assay:

As one aspect of the anti-oxidative potential of the novel analogs they were tested for their ability to inhibit the enzyme nitric oxide synthase (NOS). This assay can also serve as another indication of the anti-inflammatory cascade, as well as the anti-oxidative mechanisms.

(e) Ear Edema Model:

The anti-inflammatory activity of the new analogs is screened using an ear edema model in mice. This test system utilizes Croton oil or Arachidonic acid as inflammation inducers. The ability of the test compounds to prevent or diminish the inflammatory response to these stimulants is indicative of their systemic anti-inflammatory capability.

(f) Improved Clinical Outcome After Closed Head Injury in Rats:

Severe head injury is associated with high mortality and severe neurological impairment. Animals subjected to head trauma in a controlled fashion serve as models in which to test drugs of therapeutic potential. Test compounds can be evaluated both for improved clinical outcome and for reduction of edema induced by closed head injury. The ability of compounds to reduce the severity of neurological symptoms and to reduce brain edema is considered a measure of their potency in reducing brain damage.

(g) Transient Middle Cerebral Artery Occlusion (MCAo):

The middle cerebral artery is the cerebral blood vessel most susceptible to stroke in humans. In animals, coagulation, permanent ligation or permanent placement of an occluding thread ink the artery produces a permanent focal stroke affecting the MCA territory. Transient ligation or occlusion results in transient focal stroke. Both transient and permanent focal strokes result in varying degrees of edema and infarction in the affected brain regions. The ability of compounds to reduce the volumes of edema and infarction is considered a measure of their potential as anti-stroke treatment.

(h) Optic Nerve Crush:

Application of mechanical pressure to the rat optical nerve results in crush injury of the axons, which is accompanied by immediate changes in oxidative metabolism and delayed axonal death and blindness. The ability of compounds to protect the axons and promote axonal sprouting is determined in this assay by following GAP-43 as a specific protein for nerve growth cones (i) Parkinson's Disease:

MPTP-induced model of Parkinson's Disease (PD) in mice is used to evaluate the value of the novel PRS-211 compounds as therapeutic agents for PD.

(j) Myocardial Protection:

A rat model of ischemia and reperfusion was used to test the ability of compounds to reduce the volumes of infarction is considered a measure of their potential as cardioprotectors.

(k) Prevention and Reversal of Tolerance:

A mice model of acute pain, the tail flick model, was used to test the ability of compounds to prolong the analgesic activity of opioids, by preventing the development of tolerance, and their ability to reverse established tolerance.

Each of these systems represents an aspect of neuroinflammation, neurotoxicity or ischemia, which is amenable to intervention by pharmaceutical agents. The compounds of the present invention exert their demonstrated neuroprotective and anti-inflammatory effects by virtue of a plurality of mechanisms. Certain embodiments of the present invention exert their effect by binding to the NMDA receptor. Among the compounds of the present invention, the amine derivatives in particular have been shown to possess little or no NMDA receptor blocking activity and appear to exert their effect via the AA/PG or oxidative pathways. Nevertheless, it cannot be ruled out that their activity is mediated by other receptors or additional mechanisms.

This evaluation clearly supports the concept that PRS-211 compounds are not acting solely as NMDA receptor antagonists. Rather the therapeutic effects of PRS-211 compounds may be attributable to additional mechanisms including inhibition of tumor necrosis factor, antioxidant and radical scavenger properties, anticholinergic action, platelet activating factor antagonism, anti-inflammatory activity by direct or indirect modulation of arachidonic acid, or inhibition of lipid peroxidation, among others. All of these types of pharmacologic agents have been suggested potentially to improve functional outcome after brain injury. All of these mechanisms may be involved in delayed, secondary or chronic neuronal damage following injury to the CNS (McIntosh, *J. Neurotrauma* 20:215–243, 1993).

The prototype drug used for evaluation of NMDA blocking activity is the compound MK-801, which is a potent and selective NMDA receptor antagonist that cannot be used as a human therapeutic agent due to its toxicity. We have evaluated the similarities and differences between the biological activities of MK-801 and the novel PRS-211 compounds, as summarized in Table 1 in U.S. Pat. No 6,096,740, which is incorporated by reference herein.

Compounds

The currently preferred compounds according to the present invention are novel analogs of the lead compound dexanabinol, also denoted as HU-211, which is disclosed in U.S. Pat. No. 4,876,276. The neuroprotective effects of dexanabinol are disclosed in U.S. Pat. No. 5,284,867.

Among the novel compounds tested, analogs of dexanabinol bearing a heterocyclic moiety attached via a methylene bridge at position 1 are currently more preferred. Some of these novel compounds, particularly those having shortened tails compared to dexanabinol, as residue $R_2$, have the added advantage of being more soluble in some aqueous solutions, whereas the parent compounds are extremely hydrophobic.

These preferred compounds according to the present invention can conveniently be synthesized using dexanabinol as a starting material according to Scheme I, as presented in FIG. 1.

EXAMPLES

The following examples are intended to illustrate the present invention and these are to be construed in a non-limitative manner.

Synthetic Examples

Synthesis of (+)-(3S,4S)-6,6-Dimethyl-(1,1-dimethylheptyl)-1-hydroxy-9-(bromomethyl)-6a,7,10,10a-tetrahydro-6H-dibenzo[b,d]pyran (Compound 1)

Compound 1

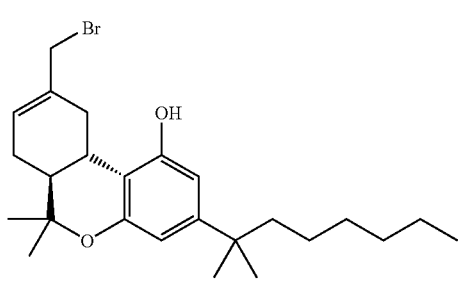

Procedure

A suspension of Dexanabinol (1.8 g, 4.66 mmol) and Triphenylphosphine (1.63 g, 6.2 mmol) in acetonitrile (8 ml) was stirred under nitrogen atmosphere at (−10)–(−5)° C. A solution of carbon tetrabromide (2.05 g, 6.2 mmol) in acetonitrile (8 ml) was added in portions. After 1 h at ~−10° C. the reaction was allowed to warm to room temperature. Stirring at 18° C. is continued then for 48 hrs. The solvent was evaporated under reduced pressure at 30° C. The residue was diluted with toluene (10 ml) and the obtained solution filtered through a silica gel column (40 g suspended in toluene), using toluene as eluent. 1.9 g (y=91%) was collected. Purity was determined by MS, and 1H-NMR.

Synthesis of (+)-(3S,4S)-6,6-Dimethyl-(1,1-dimethylheptyl)-1-hydroxy-9-(imidazolomethyl)-6a,7,10,10a-tetrahydro-6H-dibenzo[b,d]pyran (Compound 2)

Compound 2

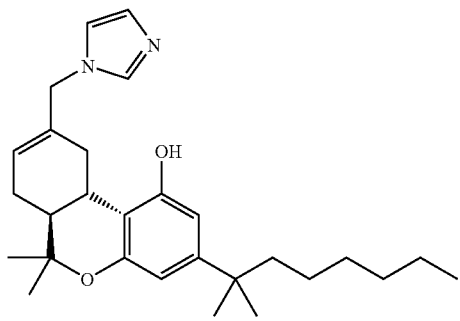

Procedure

A mixture of Compound 1 (100 mg, 0–22 mmole), Imidazole (150 mg, 2.2 mmole) and xylenes (2.5 ml) was concentrated under reduced pressure to a volume of about ~1 ml. The mixture was dissolved in anhydrous THF (4 ml) and the solution stirred at (−)10° C., under nitrogen atmosphere. Butyl lithium (0.9 ml, 18 mmole) was added portion-wise. The reaction mixture was allowed to warm slowly to room temperature and stirred for 2.5 hours. The reaction was kept overnight at −20° C. The reaction was poured into crushed ice (~4 g), neutralized with acetic acid and extracted with ether (3×20 ml). The organic phase was washed with water (20 ml), dried over MgSO$_4$ and the solvent evaporated. The product was purified by column chromatography on silica gel (5 g), using ethyl-acetate as eluent. 58 mg (yield=60%) of compound 2 was collected and purity determined by MS, and 1H-NMR.

Synthesis of (+)-(3S,4S)-6,6-Dimethyl-(1,1-dimethylheptyl)-1-hydroxy-9-(triazolomethyl)-6a,7,10,10a-tetrahydro-6H-dibenzo[b,d]pyran (Compounds 3a & 3b).

3a

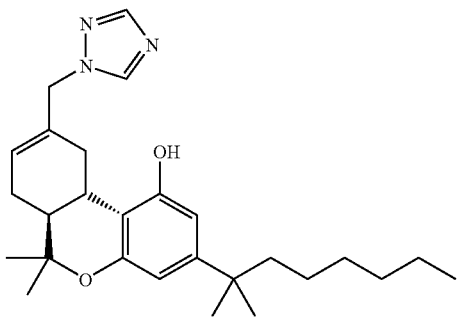

3b

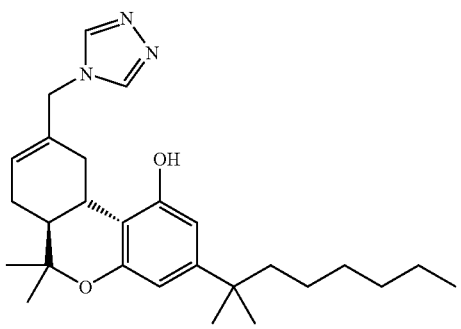

Procedure

A mixture of Compound 1 (100 mg, 0.22 mmole) and 1,2,4 triazole was stirred under nitrogen atmosphere at ~(−5° C). DBU (0.26 ml, 1.78 mmol) was added and the reaction mixture left at room temperature overnight. The reaction was poured onto ice, neutralized with acetic acid, and extracted with ethyl-ether (3×10 ml). The organic layer was dried over MgS0$_4$. On TLC two main compounds were seen and were separated by MPLC:

Compound 3a—elution with ethyl-acetate—47 mg
Compound 3b—elution with methanol-ethyl acetate (10:90)—10 mg.

Purity was determined by MS, and 1H-NMR.

Synthesis of (+)-(3S,4S)-6,6-Dimethyl-(1,1-dimethylheptyl)-1-hydroxy-9-(tetrazolomethyl)-6a,7,10,10a-tetrahydro-6H-dibenzo[b,d]pyran (Compounds 4a & 4b).

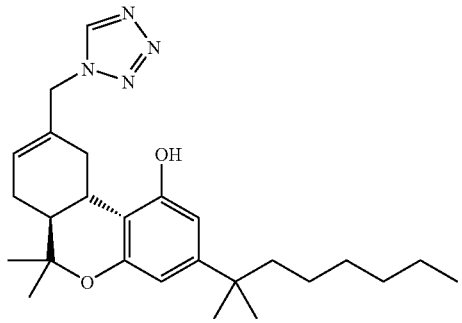

4a

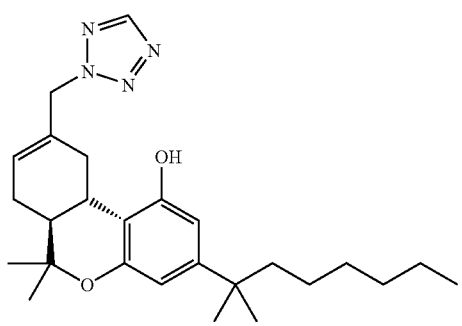

4b

Procedure

A mixture of Compound 1 (0.25 mg, 0.56 mmole) and tetrazole in dry THF (20 ml) was stirred under nitrogen atmosphere at ~(−) 5° C. (methanol/ice bath). DBU (0.65 ml, 4.4 mmole) was added (in portions), the reaction mixture was allowed to warm slowly to room temperature, left overnight and left for another 24 hours at 40° C. to fully dissolve starting material. The reaction was poured onto ice, neutralized with acetic acid and extracted with ethyl-ether (3×30 ml). The organic phase was dried over MgSO₄ and the solvent evaporated. On TLC, two main compounds were seen, that could be separated by column chromatography on silica gel (80 gr):

Compound 4a (elution with 3% ethyl-acetate in toluene)—110 mg. Compound 4b (elution with 15% ethyl-acetate in toluene)—120 mg. The compounds were washed twice with saturated solution of NaHCO₃, then with water, dried over Na₂SO₄ and evaporated.

Compound 4a–64 mg. Compound 4b–65 mg

Purity was determined by MS, and 1H-NMR.

Synthesis of (+)-(3S,4S)-6,6-Dimethyl-(1,1-dimethylheptyl)-1-hydroxy-9-(pyrazolomethyl)-6a,7,10,10a-tetrahydro-6H-dibenzo[b,d]pyran (Compound 5)

Compound 5

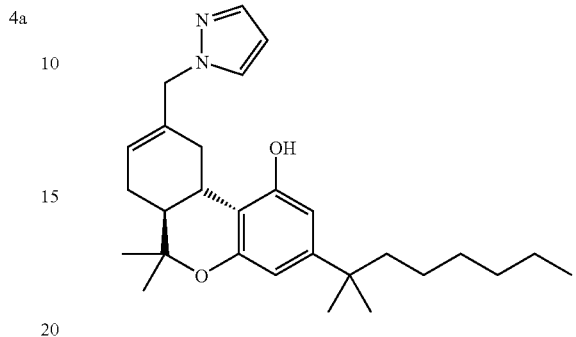

Procedure

A mixture of Compound 1 (1g, 2.2 mmole) and pyrazole (1.50 g, 22 mmol) in anhydrous THF (20 ml) was stirred under nitrogen atmosphere while being cooled. N-Butyl lithium (7 ml, 11 mmol) was added portion wise, and the reaction mixture stirred overnight at room temperature. The reaction mixture was poured into crushed ice (~4 g), neutralized with acetic acid and extracted with ethyl acetate (3×20 ml). The organic phase was washed with water (20 ml), dried over MgSO₄ and the solvent evaporated. The product was purified by column chromatography on silica gel (5 g), using 10% ethyl-acetate in petroleum ether as eluent to afford 470 mg (yield=60%) of compound Purity was determined by MS, and 1H-NMR.

Synthesis of (+)-(3S,4S)-6,6-Dimethyl-(1,1-dimethylheptyl)-1-hydroxy-9-(4,4-Dimethyl-2-imidazolomethyl)-6a,7,10,10a-tetrahydro-6H-dibenzo[b,d]pyran (Compound 6)

Compound 6

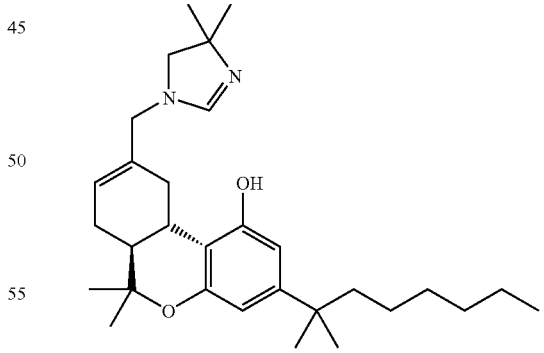

Procedure

To a solution of Compound 1 (50 mg, 0.4 mmol) in THF, 4,4-dimethyl-2-imidazoline (0.4 ml) was added and the mixture stirred overnight at room temperature. The reaction mixture was poured onto crushed ice, acidified with acetic acid (pH 5), and extracted with EtOAc. The combined organic phase was dissolved in acetonitrile and water and lyophilized. Yield: 150 mg

Synthesis of (+)-(3S,4S)-6,6-Dimethyl-(1,1-dimethylheptyl)-1-hydroxy-9-(pyrrolinomethyl)-6a,7,10,10a-tetrahydro-6H-dibenzo[b,d]pyran (Compound 7)

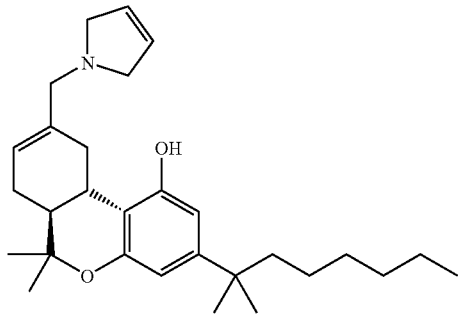

Compound 7

Procedure

To absolution of Compound 1 (200 mg, 0.45 mmol) in anhydrous THF (5 ml), pyrroline (0.3 ml) was injected and the mixture stirred at room temperature overnight. The reaction was carried out under nitrogen atmosphere. The mixture was poured into ice, acidified with acetic acid (pH 5) and extracted with EtOAc (3×20 ml). The combined organic phases were washed with water, dried and evaporated. After lyophilization, 120 mg of product was collected.

Synthesis of (+)-(3S,4S)-6,6-Dimethyl-(1,1-dimethylheptyl)-1-hydroxy-9-(pyrrolidinomethyl)-6a,7,10,10a-tetrahydro-6H-dibenzo[b,d]pyran (Compound 8)

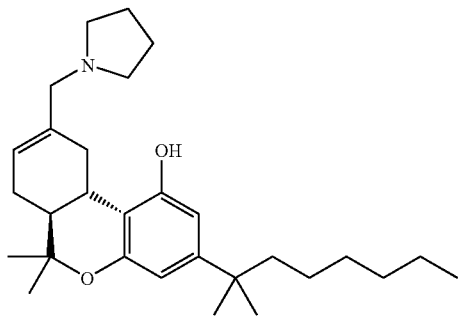

Compound 8

Procedure

A mixture of Compound 1 (0.5 g, 1.1 mmol) and pyrrolidine (0.5 ml) in dry THF was stirred at room temperature overnight. The reaction mixture was poured into water, acidified with acetic acid (pH 6) and extracted with EtOAc (3×30 ml). The combined organic phase was washed with water, dried and evaporated. The residue was chromatographed over a silica gel column and eluted with 15% methanol in EtOAc. The product obtained was lyophilized to afford 270 mg of pure product.

Synthesis of (+)-(3S,4S)-6,6-Dimethyl-(1,1-dimethylheptyl)-1-hydroxy-9-(methylsulfidomethyl)-6a,7,10,10a-tetrahydro-6H-dibenzo[b,d]pyran (Compound 9)

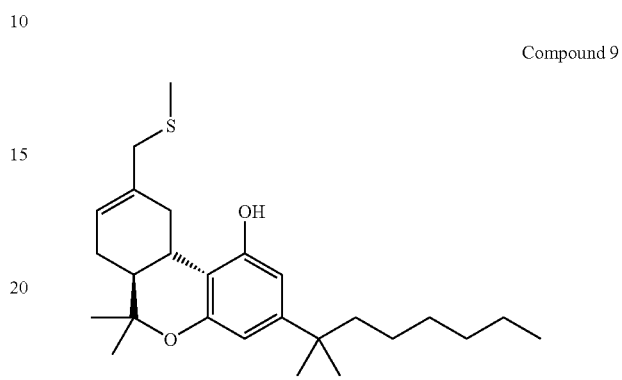

Compound 9

Procedure

To a solution of Compound 1 (100 mg, 0.2 mmol) in THF, sodium methyl sulfide was added. The reaction mixture was stirred overnight, evaporated and chromatographed over silica gel to afford 100 mg of compound 9.

Synthesis of (+)-(3S,4S)-6,6-Dimethyl-(1,1-dimethylheptyl)-1-hydroxy-9-(methylsulfoxidomethyl)-6a,7,10,10a-tetrahydro-6H-dibenzo[b,d]pyran (Compound 10)

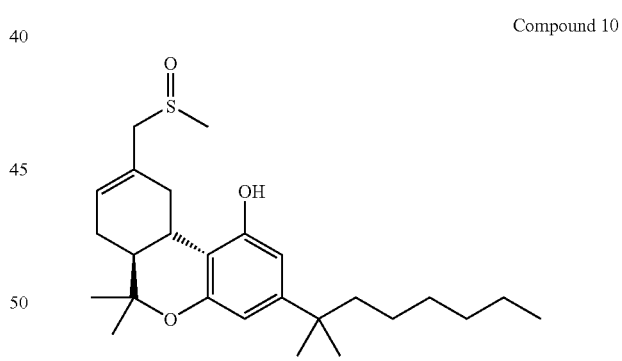

Compound 10

Procedure

To a cooled solution (−20° C.) of Compound 1 (1.7 g, 4 mmol) in dry dichloromethane (120 ml) meta chloroperbenzoic acid (0.83 g, 4.8 mmol) was added and the mixture stirred 30 min at the above temperature. The reaction was then poured into a 7% sodium hydrogenocarbonate solution (250 ml) containing excess sulfite. The product was extracted in dichloromethane (3×100 ml), washed with water (2×150 ml) dried and evaporated. The residue was chromatographed on silica gel column using 5% EtOH in EtOAc. The product obtained was lyophilized to obtain 1.2 g of white powder.

Synthesis of (+)-(3S,4S)-6,6-Dimethyl-(1,1-dimethylheptyl)-1-hydroxy-9-(2-methylthio-2-imidazolinomethyl)-6a,7,10,10a-tetrahydro-6H-dibenzo[b,d]pyran (Compound 11)

Compound 11

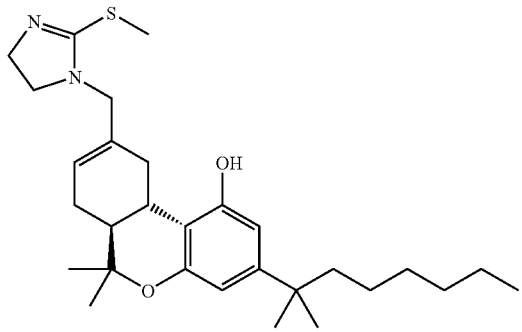

Procedure

To a mixture of 2-methylthio-2-imidazoline hydriodide (0.3 g, 1.2 mmol) in anhydrous THF (5 ml) DBU (0.18 ml, 1.22 mmol) was added and the mixture stirred at room temperature under nitrogen atmosphere. A solution of Compound 1 (0.2 g, 0.4 mmol) in anhydrous THF (2 ml) was injected and the mixture stirred overnight at room temperature. The reaction mixture was poured into water, acidified with acetic acid (pH 5) and extracted with EtOAc. The organic phase was washed with water, dried, with anhydrous sodium sulfate, and evaporated. The residue was chromatographed over silica gel using 25% methanol in ethyl acetate as the eluting system. 120 mg of compound are obtained.

Synthesis of (+)-(3S,4S)-6,6-Dimethyl-(1,1-dimethylheptyl)-1-hydroxy-9-(phtalimidomethyl)-6a,7,10,10a-tetrahydro-6H-dibenzo[b,d]pyran (Compound 12)

Compound 12

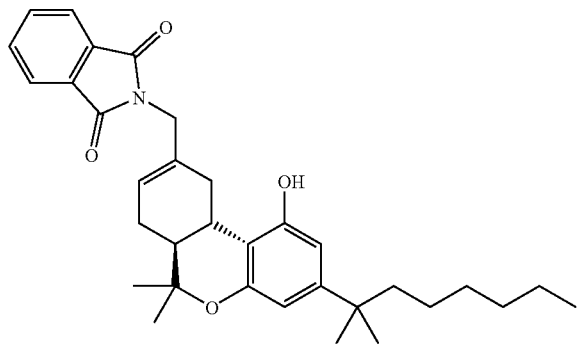

Procedure

A mixture of compound 1 (1.2 g, 2.15 mmol), phtalimide potassium salt (1.85 g) in methyl sulfoxide (6.0 ml) was stirred under argon at 50 C for 18 hours. The resulting mixture was poured onto crushed ice (20 g), acidified to pH 6 with acetic acid, and extracted with chloroform (2×20 ml). The extract was dried over sodium carbonate and concentrated under reduced pressure. The residue was subjected to column chromatography using toluene and toluene/ethyl acetate as the eluent to afford 0.4 g of product.

Synthesis of (+)-(3S,4S)-6,6-Dimethyl-(1,1-dimethylheptyl)-1-hydroxy-9-(amino methyl)-6a,7,10,10a-tetrahydro-6H-dibenzo[b,d]pyran (Compound 13)

Compound 13

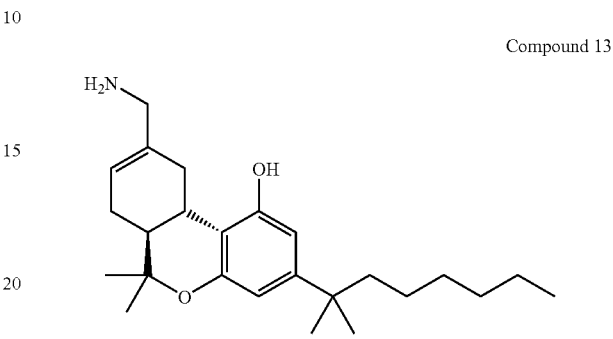

Procedure

A solution of Compound 12 (0.516 g, 1 mmol) and hydrazine monohydrate (0.159 ml, 3.1 mmol) in ethanol (15 ml) was heated to reflux under argon for 2 hours. Water (0.5 ml) containing concentrated HCl (0.5 ml, 6 mmol) was added and reflux was continued for an additional hour. The solution was left overnight at 22 C. The mixture was diluted with toluene (10 ml). The precipitate was filtered off and washed with ethanol (5 ml). The filtrate and the washings were combined, diluted with ethyl ether (10 ml) and washed with 5% sodium hydrogenocarbonate. The organic phase was separated, dried over sodium carbonate and the solvents were evaporated under reduced pressure. The residue was crystallized from acetonitrile to afford 0.3 g.

Synthesis of (+)-(3S,4S)-6,6-Dimethyl-(1,1-dimethylheptyl)-1-hydroxy-9-(acetamidomethyl)-6a,7,10,10a-tetrahydro-6H-dibenzo[b,d]pyran (Compound 14)

Compound 14

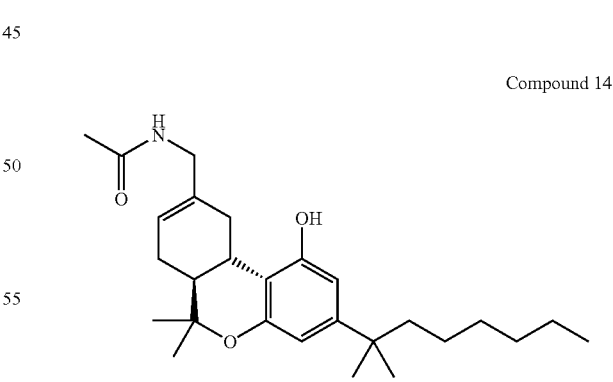

Procedure

Compound 13 (0.15 g, 0.39 mmol) was dissolved in acetic anhydride at room temperature. After about 3 minutes a precipitate formed. The mixture was set aside at 22° C. for one hour. Methanol (5 ml) was added and all precipitate dissolved giving a transparent solution. The solution was stored at 22 C for 18 hours and the solvent evaporated. The residue was dried in a vacuum oven to give 0.16 g of solid, which crystallized from acetonitrile to afford 0.1 g of crystals.

Synthesis of (+)-(3S,4S)-6,6-Dimethyl-(1,1-dimethylheptyl)-1-hydroxy-9-(1H-imidazol-2-ylsulfanyl methyl)-6a,7,10,10a-tetrahydro-6H-dibenzo[b,d]pyran (Compound 15)

Compound 15

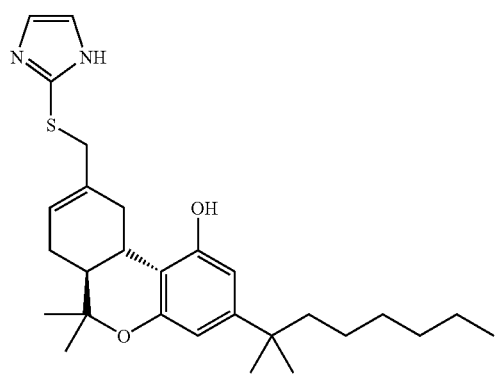

Procedure

A mixture of the Compound 1 (2.5 gr, 5.6 mmole) and 2-mercaptoimidazole (2.2 gr, 22 mmole) was stirred under nitrogen atmosphere. Triethylamine was added slowly and the obtained mixture was stirred overnight at room temperature. The reaction mixture was poured into water, neutralized with acetic acid and extracted several times with ethyl acetate. The combined organic phase was washed with water, dried over $MgSO_4$ and evaporated to give the crude product which was further purified by silica gel column (elution with 25% ethyl-acetate in petroleum-ether). After lyophilization, compound 15 was obtained as a white powder (yield 1.87 gr, 71%):

Synthesis of (+)-(3S,4S)-6,6-Dimethyl-(1,1-dimethylheptyl)-1-hydroxy-9-(4-(1-Pyrrolidinyl)-piperidinemethyl)-6a,7,10,10a-tetrahydro-6H-dibenzo[b,d]pyran (Compound 16)

Compound 16

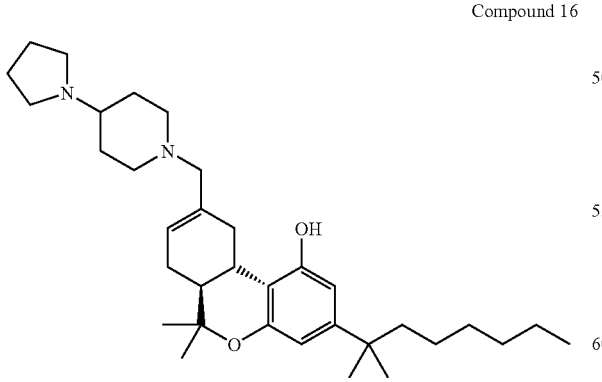

Procedure

A solution of Compound 1 (0.3 g, 0.6 mmol) and 4-(1-Pyrrolidinyl)-piperidine (0.2 g, 1.2 mmol) in dry THF (50 ml) was stirred overnight at room temperature. The reaction mixture was diluted with water (30 ml), then acidified with acetic acid and extracted with ethyl acetate (3×50 ml). The combined organic fractions were washed with water, dried with sodium sulfate and evaporated to dryness. The desired product was purified by silica gel column chromatography using ethyl acetate-petroleum ether mixture to afford pure product (yield: 85%).

Synthesis of (+)-(3S,4S)-6,6-Dimethyl-(1,1-dimethylheptyl)-1-hydroxy-9-(4-piperidinopiperidine methyl)-6a,7,10,10a-tetrahydro-6H-dibenzo[b,d]pyran (Compound 17).

Compound 17

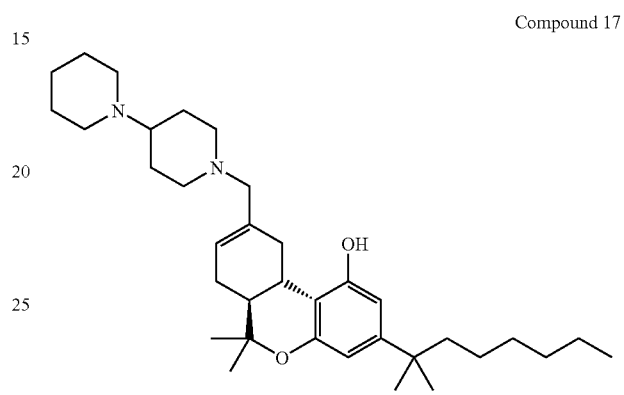

Procedure

A solution of Compound 1 (0.3 g, 0.6 mmol) and 4-piperidinepiperidine (0.21 g, 1.3 mmol) in dry THF (50 ml) was stirred overnight at room temperature. The reaction mixture was diluted with water (100 ml), then acidified with acetic acid and extracted with ethyl acetate (3×50 ml). The organic phase was washed with water (50 ml), dried with sodium sulfate and evaporated to dryness. The desired product was purified by silica gel column chromatography using ethyl acetate-petroleum ether mixture to afford pure product (yield 78%).

Synthesis of (+)-(3S,4S)-6,6-Dimethyl-(1,1-dimethylheptyl)-1-hydroxy-9-(N-benzylaniline methyl)-6a,7,10,10a-tetrahydro-6H-dibenzo[b,d]pyran (Compound 18)

Compound 18

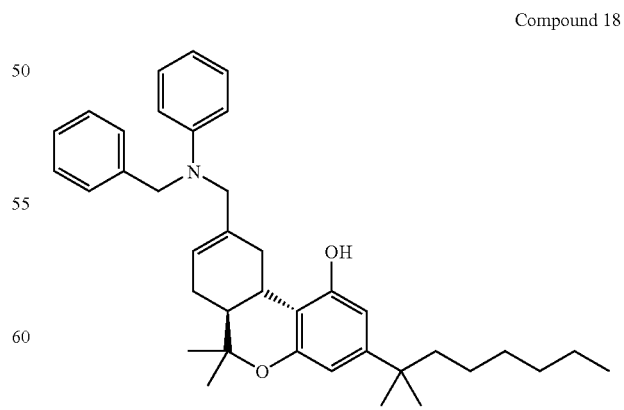

Procedure

A solution of Compound 1 (0.3 g, 0.6 mmol) and N-Benzylaniline (0.23 g, 1.3 mmol) in dry THF (50 ml) was stirred overnight at room temperature. The reaction mixture was diluted with water (100 ml), then acidified with acetic acid and extracted with ethyl acetate (3×50 ml). The organic phase was washed with water (50 ml), dried with sodium sulfate and evaporated to dryness. The desired product was purified by silica gel column chromatography using ethyl acetate-petroleum ether mixture to afford of pure product (yield: 86%).

Compound 19

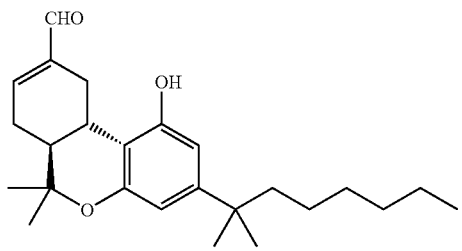

Synthesis of (+)-(3S,4S)-6,6-Dimethyl-(1,1-dimethylheptyl)-1-hydroxy-9-(N-(2-Aminoethyl)pyrro methyl)-6a,7,10,10a-tetrahydro-6H-dibenzo[b,d]pyran (Compound 20)

Compound 20

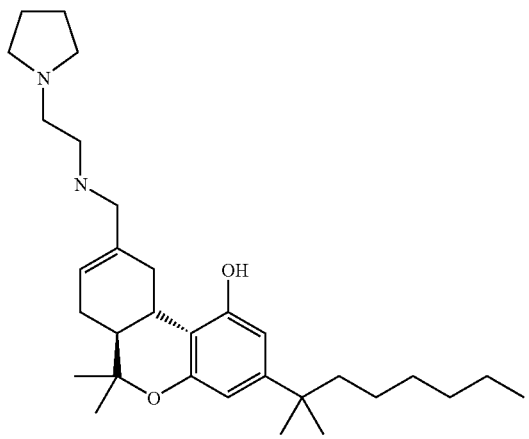

Procedure

Compound 19 (0.5 g, 1.3 mmol) and N-(2-Aminoethyl) pyrrolidine (0.44 g, 3.9 mmol) were dissolved in methanol (30 ml) and stirred at room temperature for one hour. Sodium cyanoborohydride (0.72 g) was added and the reaction stirred at room temperature overnight. The reaction mixture was acidified with diluted HCl (1N) and extracted with Ethyl acetate (3×50 ml). The organic fraction was washed with water (50 ml), dried over anhydrous sodium sulfate and evaporated under vacuum. The residue was chromatographed over silica gel column using ethyl acetate-petroleum ether as the eluting system to afford the desired product (yield: 69%).

Synthesis of (+)-(3S,4S)-6,6-Dimethyl-(1,1-dimethylheptyl)-1-hydroxy-9-(N-diethanolamine methyl)-6a,7,10,10a-tetrahydro-6H-dibenzo[b,d]pyran (Compound 21)

Compound 21

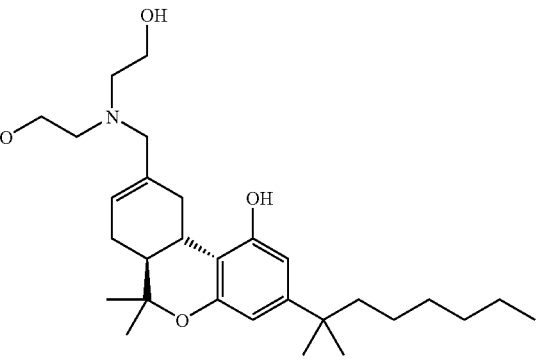

Procedure

Compound 19 (0.5 g, 1.3 mmol) and diethanolamine (0.35 g, 3.3 mmol) were dissolved in methanol (30 ml) and stirred at room temperature for one hour. Sodium cyanoborohydride (0.72 g) was added and the reaction stirred at room temperature overnight. The reaction mixture was acidified with diluted HCl (1N) and extracted with Ethyl acetate (3×50 ml). The organic-fraction was washed with water (50 ml), dried over anhydrous sodium sulfate and evaporated under vacuum. The residue was chromatographed over silica gel column using ethyl acetate-petroleum ether as the eluting system to afford the desired product (yield: 69%).

Synthesis of (+)-(3S,4S)-6,6-Dimethyl-(1,1-dimethylheptyl )-1-hydroxy-9-(4-methylpiperidine methyl)-6a,7,10,10a-tetrahydro-6H-dibenzo[b,d]pyran (Compound 22)

Compound 22

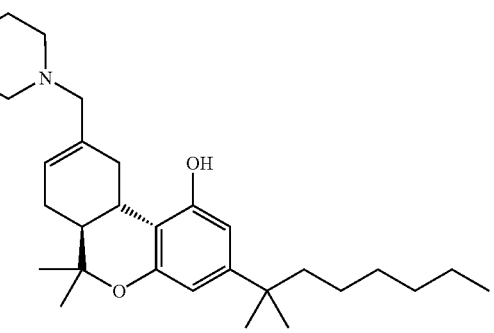

Procedure 4-methyl piperidine (0.47 ml, 6 mmole) was added to a solution of Compound 1 (1.0 gr, 2.24 mmol) in dry THF (50 ml) and the obtained mixture was stirred overnight at room temperature. The reaction mixture was poured into water, neutralized with acetic acid and extracted several times with ethyl acetate. The combined organic phases were washed with water, dried over anhydrous MgSO$_4$ and evaporated to give a crude product which was purified by flash silica gel column chromatography (elution with 25% ethyl-acetate in petroleum-ether). After lyophilization, compound 22 was obtained as a white powder (0.62 g).

Physiological Examples

Physiological Example 1

PRS-211 Analogs Analyzed by Radioligand Binding Studies

The identification of possible recognition sites for PRS-211 analogs was carried out by measuring the ability of these PRS-211 analogs to inhibit the binding of MK-801 to rat forebrain membranes. Radioligand binding studies demonstrated that the parent compound HU-211 competes with the binding of MK-801 to membranes, while it is unable to inhibit AMPA or kainic acid binding.

Forebrain Membrane Preparation:

Brains were removed from Sprague-Dawley rats no more than 5 min after decapitation. Membrane preparations were isolated according to a procedure described previously (Eshhar et al., *Brain Res.* 476:57, 1989). Prior to radioligand binding measurements, endogenous glutamate present in membranes was removed from the preparation by subjecting the membranes to 3–4 successive washings in 10 mM Tris HCl pH 7.2, performed at 4° C.

Radioligand Binding Studies:

The specific binding of the new analogs to NMDA receptors was determined by their ability to displace [$^3$H] MK-801 from NMDA receptor in rat forebrain preparations. Specifically, rat-forebrain membranes (0.1 mg) were incubated for 2 hours at room temperature with 10 nM of tritiated MK-801 and with the PRS-211 compounds at 3 doses each. Non-specific binding was determined by the use of 0.1 mM MK-801. Following the incubation, bound radioligand was separated from unbound by filtration through GF/B filters. The filters were counted in a β-counter and log of analog concentrations versus % of [$^3$H]MK-801 specific binding was plotted. The $IC_{50}$ was calculated from this plot.

Binding of [$^3$H]MK-801 to membranes was carried out in the presence of 30 μM glycine and 10 μM L-glutamate. Membranes (250 μg protein) were resuspended in 50 mM tris-acetate pH 7.4 buffer and incubated with 10 nM [$^3$H] MK-801, either alone or in the presence of PRS-211 compounds at 0.1–100 μM concentrations for three hours at room temperature (RT). Reaction buffers used in the different radioligand binding studies contained 10% of an ethanol/Emulphor 620/deionized water mixture. The ratio (by volume) of the respective components in the mixture was 20/3/57. This mixture is required for solubilizing PRS-211 compounds at concentrations above 30 μM. Reaction volume was 1 ml. Non-specific [$^3$H]MK-801 binding was determined in the presence of 100 μM unlabeled MK-801.

Figure 2:
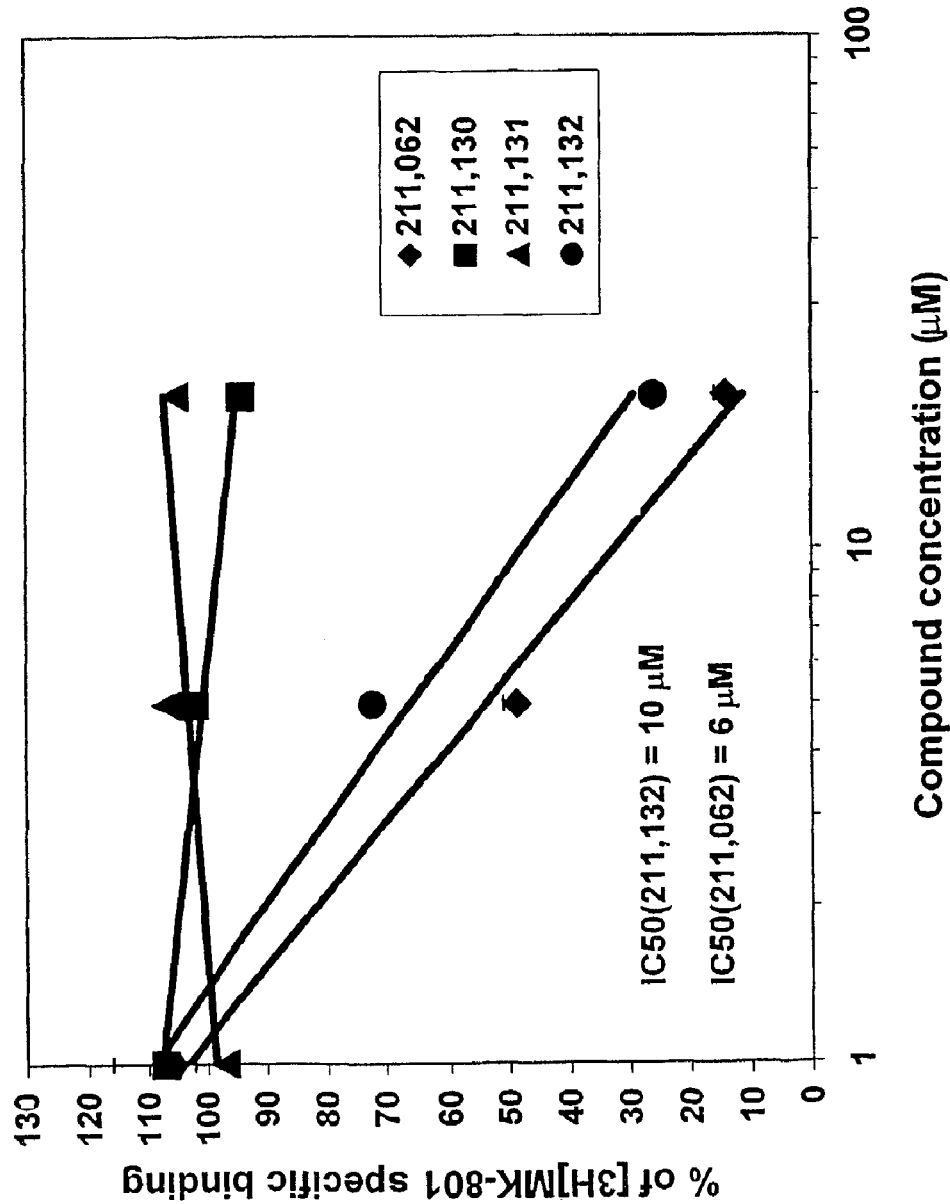
FIG. 2 shows binding curves of compounds according to the present invention to the NMDA receptor, as measured by the displacement of labeled MK-801.
Figure 3:
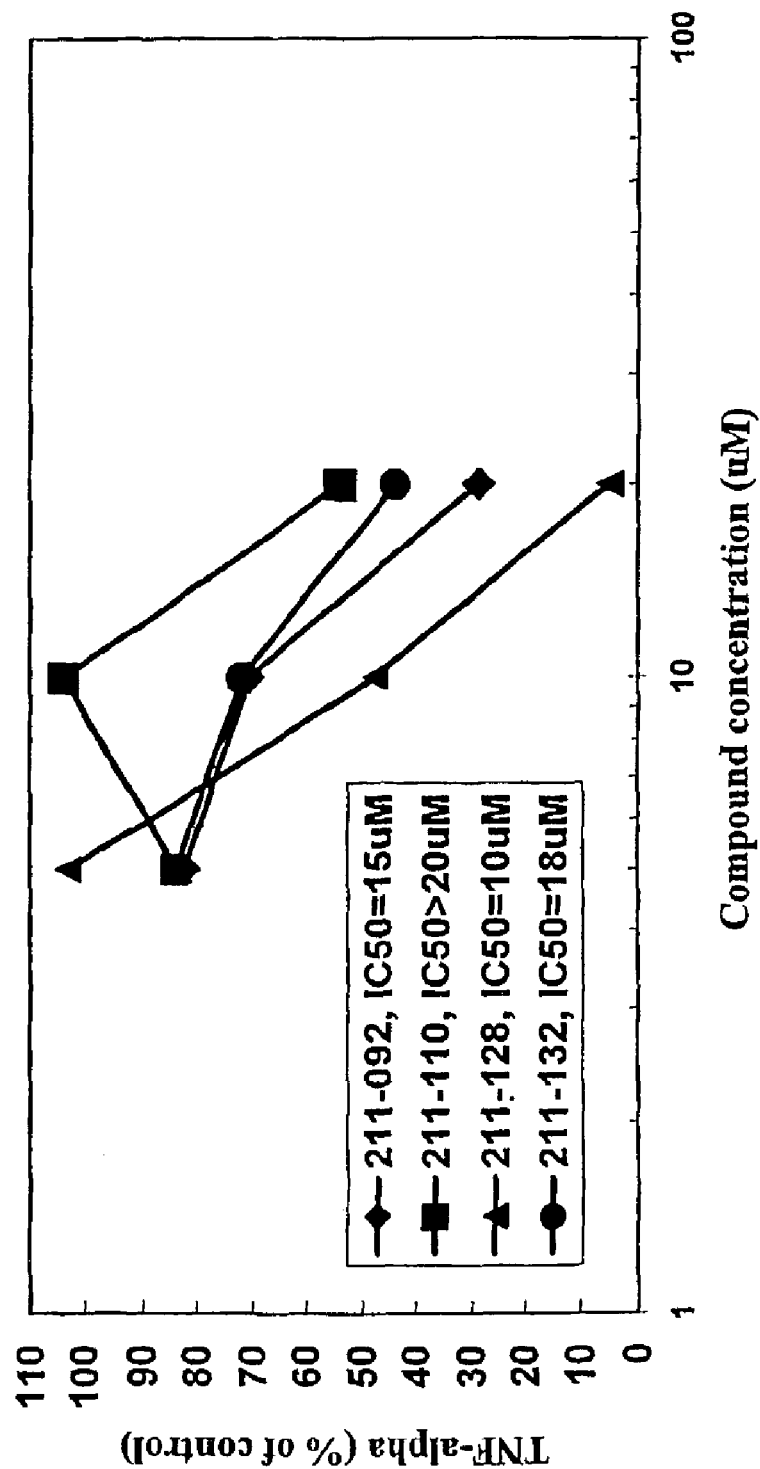
FIG. 3 shows TNF alpha inhibition by novel dexanabinol derivatives.
Figure 4:
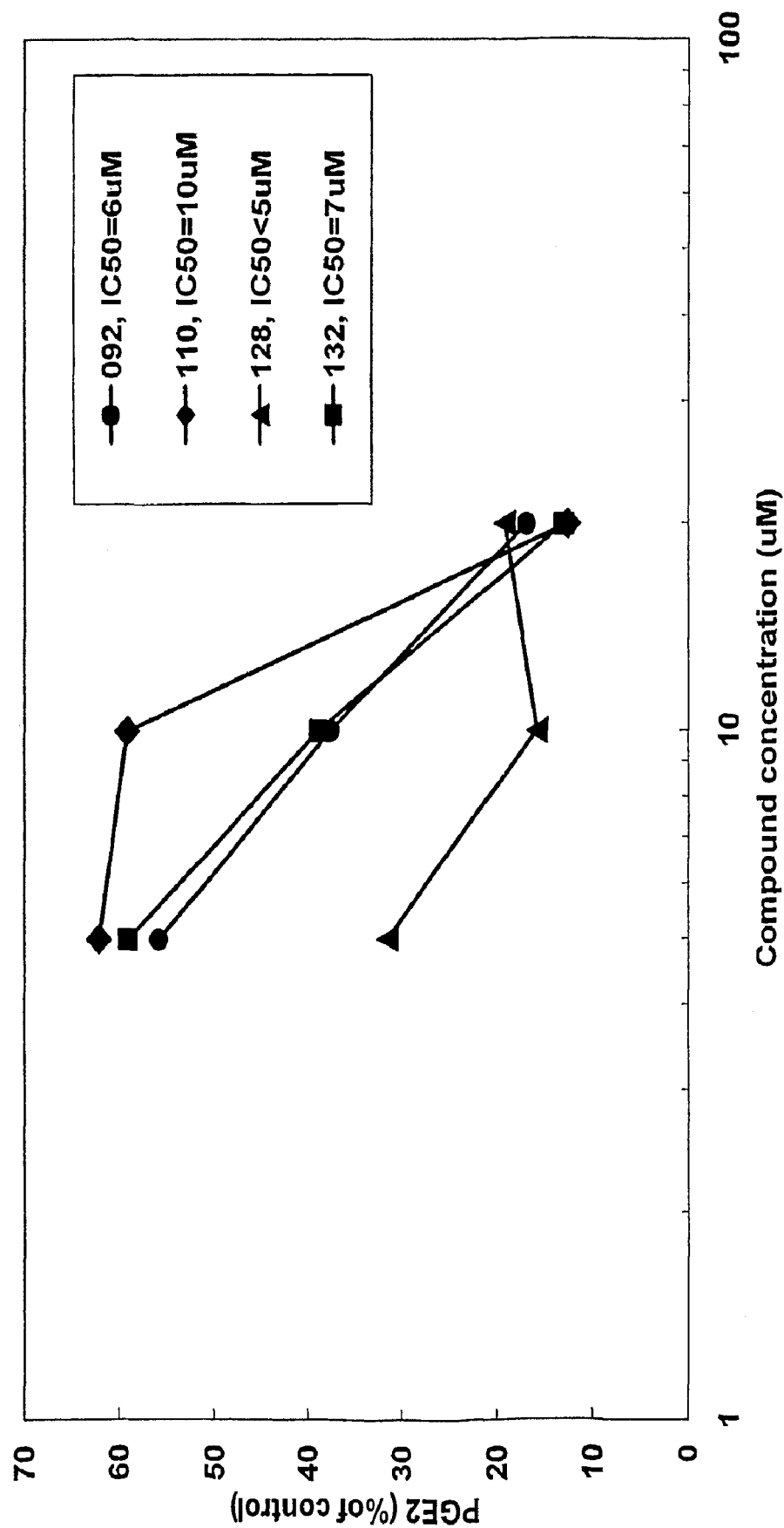
FIG. 4 illustrates inhibition of PGE2 by novel dexanabinol derivatives.
Figure 5:
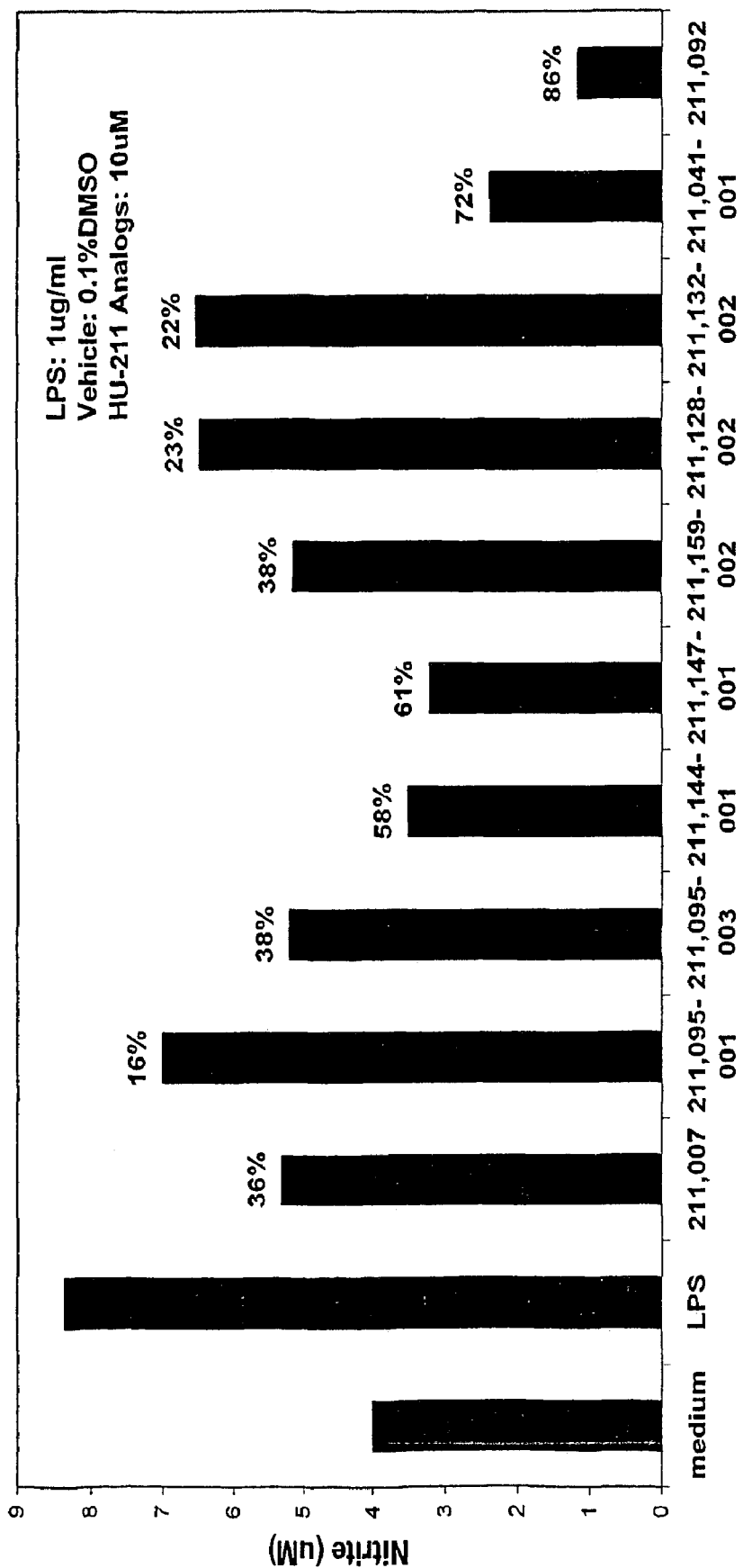
FIG. 5 shows nitric oxide synthase inhibition by novel dexanabinol analogs.

Concentration dependence of certain PRS-211 analogs on inhibition of [$^3$H]MK-801 binding is illustrated in FIG. 1. The inhibition constant ($K_I$) value displayed by PRS-211, 007 was found to be 11.0±1.3 μM. The $IC_{50}$ of several dexanabinol derivatives is presented in FIG. 2. Thus, for example, the mean IC50 of HU-211 (PRS-211,007) was 10 μM compared with that of 2.5 μM for PRS-211,095 (imidazole derivative), versus >20 μM of PRS-211,128 and 4.5 μM for PRS-211,132 and 0.35 μM of PRS-211,220 (pyrazole derivative).

Physiological Example 2

The In Vivo Anti-Inflammatory Effect of PRS-211 Compounds in the Ear Edema Model The anti-inflammatory activity of the new analogs was established in the ear edema model in mice using Croton oil (CO) or Arachidonic acid (AA) as inflammation inducers.

Briefly, the animals were anesthetized and either test analog or identical volume of vehicle is injected IP. CO or AA solution diluted with acetone was injected (ear/ear) to one ear. The contralateral ear, serving as control, received an equal volume of the diluent. One to 3 hours post injection the animals were euthanized and ear thickness measurements are taken in duplicates using a low tension, spring loaded dial micrometer. The edge of the micrometer pads was placed on the outer edge of the ear. Thickness was measured in units of 0.01 mm. Tissue weight was determined by excising a 6 mm diameter disc of ear tissue from the ear lobes using a metal punch. Inflammation/Edema is expressed as the increase in thickness/weight of treated versus diluent treated contralateral ear in animals injected with either test new analogs or vehicle. Dose response curves, with at least 4 doses, are used to calculate potency ($ED_{50}$), and the maximal efficacy (% of inhibition of Edema), for each of the test drugs. The results obtained with certain preferred novel analogs are summarized in Table 2 above.

Physiological Example 3

In Vitro Screening of Anti-Inflammatory Activity

A. Inhibition of Prostaglandin Synthesis

The inhibitory effect of Dexanabinol new analogs on prostaglandin synthesis was evaluated in macrophage cell cultures. Macrophages were seeded in a 24 well NUNC plates, and incubated with DMEM medium for 24 hours to allow attachment to plastic. The wells were vacuumed and a different new analog is added for 1 hour. Treatments are done in triplicates. Following, LPS was added for a duration of 3–24 extra hours, to induce the inflammatory response. The supernatants were collected and analyzed for $PGE_2$ by enzyme immunoassay technique Biotrak kit (Amersham Pharmacia Biotech).

The results obtained with certain preferred novel analogs are summarized in Table 2 above.

B. Inhibition of TNFα

The method for macrophage cell culture growth is identical to the one described in PGE2 assay. Aliquots of the supernatants collected following stimulation with LPS were quantitated for TNFα by enzyme linked immunosorbent assay (ELISA) using HRP conjugated to anti-TNFα antibodies and peroxidase as a substrate for the colorimetric reaction. The peroxidase catalyzed color reaction was stopped by acidification and the absorbance at 450 nm is measured. The absorbance at this wavelength is proportional to the concentration of TNFα in the sample determined from a standard curve plotting the concentrations of TNFα standards versus their absorbance.

C. Inhibition of Nitric Oxide Synthase (NOS)

The final products of NOS are Nitrite ($NO_2$) and Nitrate ($NO_3$). The in vitro fluorimetric assay provides an accurate method for the measurement of the Nitrite, which is the majority of NO products. The principle of the fluorimetric assay is based on the addition of DAN (2,3-diaminonaphthalene) to the aliquots of the supernatants collected from macrophage cell cultures incubated with the new analogs and stimulated with LPS. Following, NaOH was added to convert Nitrite to a fluorescent compound 1(H)-naphthtriazole. The fluorescence was measured immediately in a fluorimeter using excitation wavelength of 365 nm and an emission wavelength of 450 nm.

Physiological Example 4

The Effect of PRS-211 Compounds on Cerebral Edema in a Rat Model of Closed Head Injury The cerebroprotective effect of PRS-211 compounds was assessed in a model of head trauma (HT) in rats. Injury was induced in anesthetized rats by a weight-drop device followed by a recovery period of up to 48 hours. This type of trauma produces brain edema (i.e. increase in water content, decrease in specific gravity in the brain), breakdown of the blood brain barrier (BBB) and clinical dysfunction. The clinical status of the rats was evaluated 1, 24 and 48 hours after injury along with measuring the extent of cerebral edema. The neurological deficit, assessed by a set of criteria termed the Neurological Severity Score (NSS), is maximal at 1 hour after the initiation of head trauma. The NSS slowly decreases over time from the initiation of HT, with the gradual spontaneous recovery of the rats.

at any particular metabolic cascade studied. During the recovery period, the clinical status was evaluated by a set of criteria (NSS).

Trauma induced a significant decrease in specific gravity (SG) of brain tissue and increase in water content following head injury. Edema developed since more water accumulates in either the extracellular (vasogenic) or intracellular (cytotoxic) spaces. The methods employed to determine edema are based on linear gradient columns of bromobenzene and kerosene (for SG) and for water content on drying the tissue in a desiccated oven. Tissue pieces (20 mg each) were placed on top of the column and the SG calculated from the equilibrium position in the column, using a standard curve.

Results

Table 3 summarizes the results of a typical experiment in which the novel analog PRS-211-095 was injected at doses of 5–10 mg/kg. The drug was given half an hour before, or one hour after, the induction of trauma and its effect on edema and clinical outcome was evaluated 1 and 24 hours later. The results indicates a significant (p=0.003) decrease in the degree of edema developed after-head trauma (CHI), as well as a highly significant decrease (p<0.001) in the neurological deficit score as a result of PRS-211-095 treatment to traumatized rats.

TABLE 3

Cerebroprotective effects of HU-211 and PRS-211,095 in rats following Closed Head Injury (CHI)

| Treatment | Water content | | Neurological score | | ΔNSS | N = no. of rats |
|---|---|---|---|---|---|---|
| | Left | Right | 1 hr | 24 hr | 24 hr | |
| Untreated CHI-control | 84.82 ± 0.33 | 79.44 ± 0.32 | 12.2 ± 0.6 | 8.7 ± 0.6 | 3.5 ± 0.31 | 13 |
| Dexanabinol HU-211 | 83.09 ± 0.51 *p = 0.007 | 79.37 ± 0.30 | 11.7 ± 0.7 | 6.3 ± 0.6 | 5.5 ± 0.42 | 8 |
| PRS-211,095 | 82.89 ± 0.48 *p = 0.003 | 79.75 ± 0.20 | 11.9 ± 0.6 | 5.4 ± 0.5 | 6.5 ± 0.45 | 10 |

The novel analog PRS-211-095 significantly reduces edema formation and BBB disruption when given before (30 min), immediately after HT (0 min) or even 1 and 2 hours after HT.

The doses required for significant neuroprotection depend on the mode of administration and range from 0.5–20 mg/kg. It is also important to note that the NSS, mainly specific motor function (e.g. beam-walk and balance) improved significantly upon administration of PRS-211. In fact, even one dose of 5 mg/kg of PRS-211-095, given 1 hour after the impact, effectively reduced edema and improved the clinical outcome measured 24 hours after HT.

Experimental Procedure:

The model was described in detail by Shapira et al., Crit. Care Med. 16:258–265, 1988. Rats were subjected to head trauma (HT) by a surviving rats were followed up after one week. During that period they had free access to food and water, and were kept 2–3 rats to a cage. At any predesignated time (15 min, 1, 4, 24, 48 hrs, etc.) rats were sacrificed. Their brains were then rapidly removed and cortical tissue taken to determine water content, ions and the metabolites of interest The effect of PRS-211 analogs was calculated by the percent edema formation, where 100% was taken as edema in control, non-treated rats. Thus, the reduction in the SG was calculated as follows:

$$SG(\text{sham}) - SG(\text{drug}) / SG(\text{sham}) - SG(\text{cont}) \times 100$$

The increase in water content was calculated as follows:

$$[\% \ H_2O(\text{drug}) - \% \ H_2O(\text{sham}) / \% \ H_2O(\text{cont}) - H_2O(\text{sham})] \times 100$$

All results presented in the table are statistically different (p<0.05) from control, traumatized vehicle treated rats.

Figure 6:
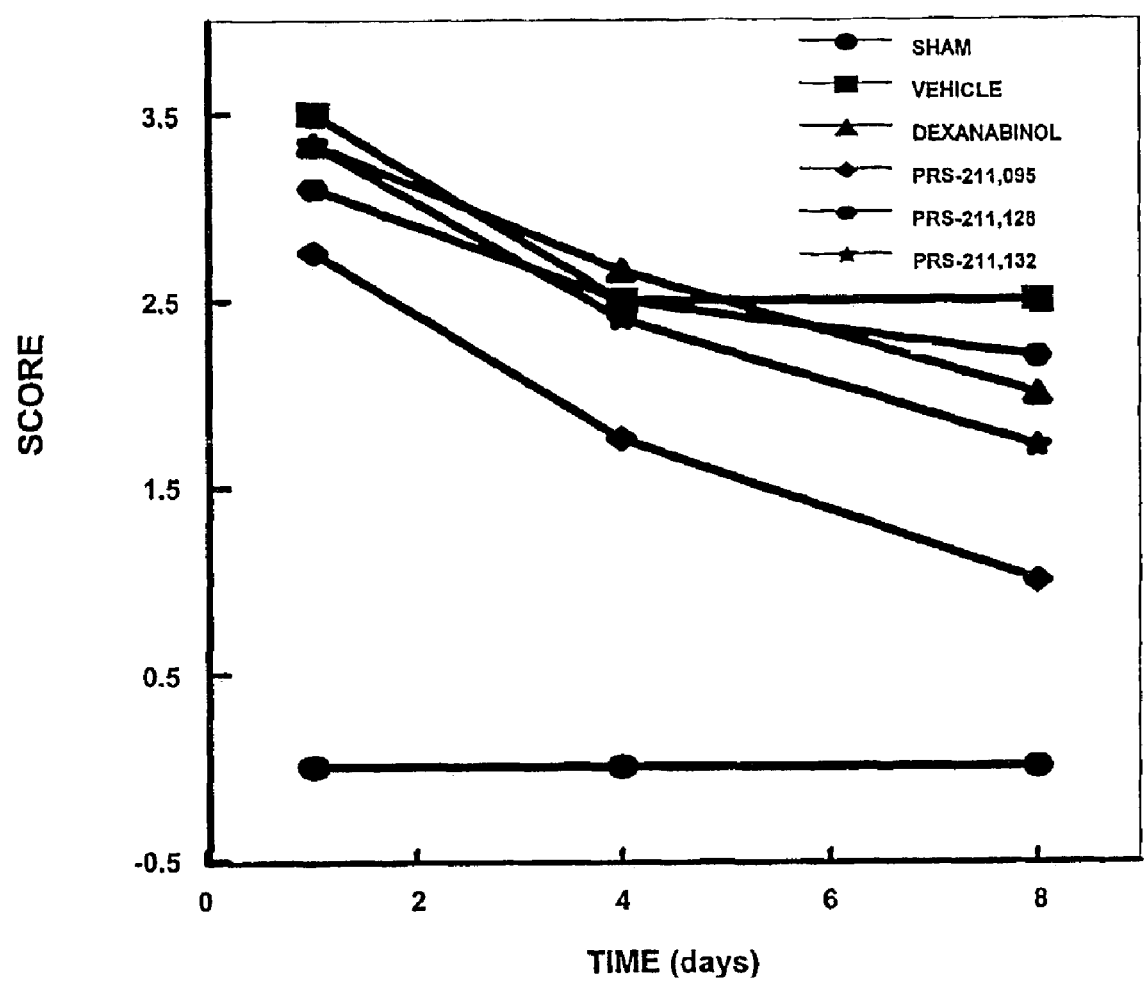
FIGS. 6–8 show the decreased mortality and improved clinical and neurological outcome following transient middle cerebral artery occlusion in rats treated with certain preferred dexanabinol derivatives.
Figure 7:
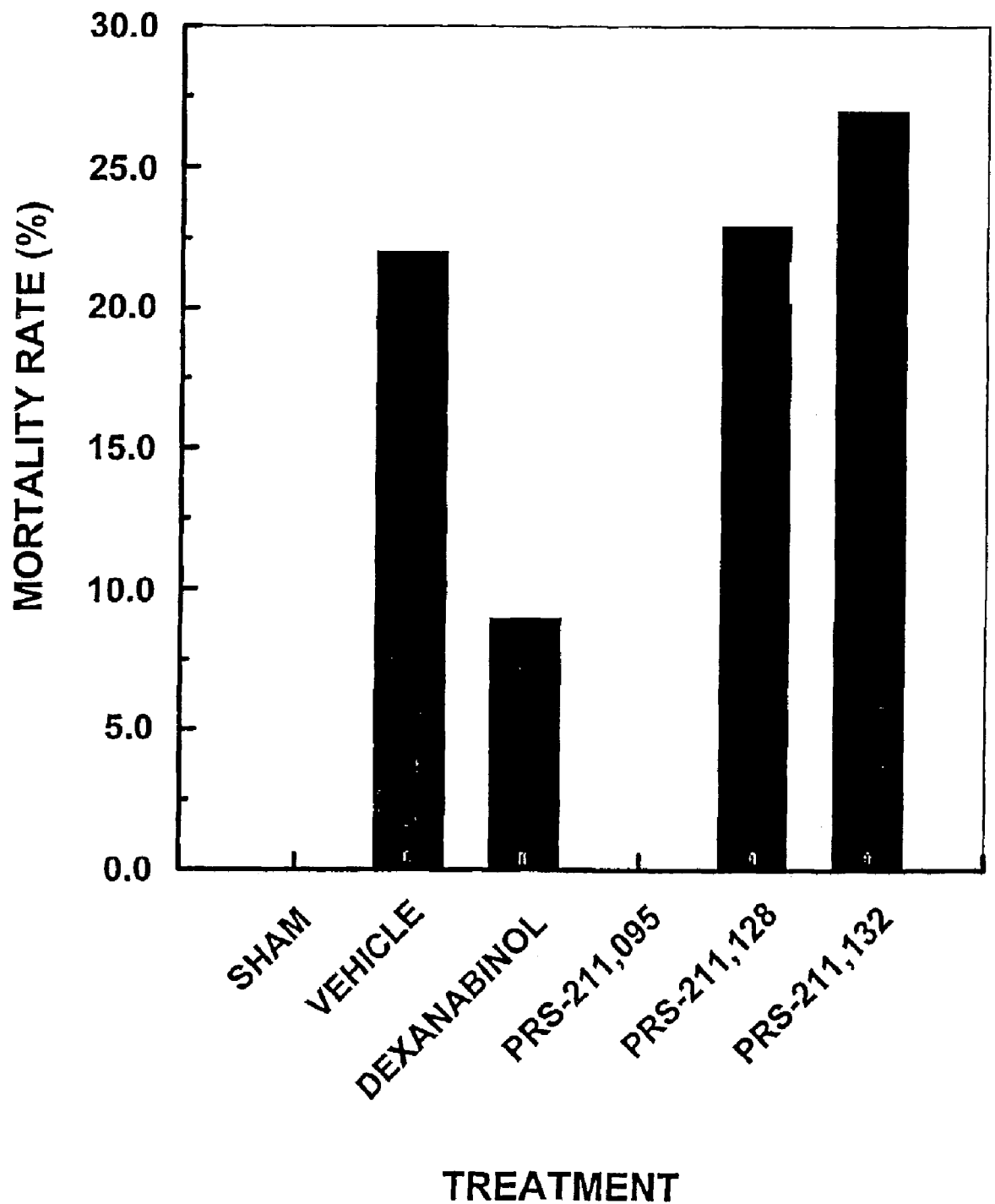
Figure 8:
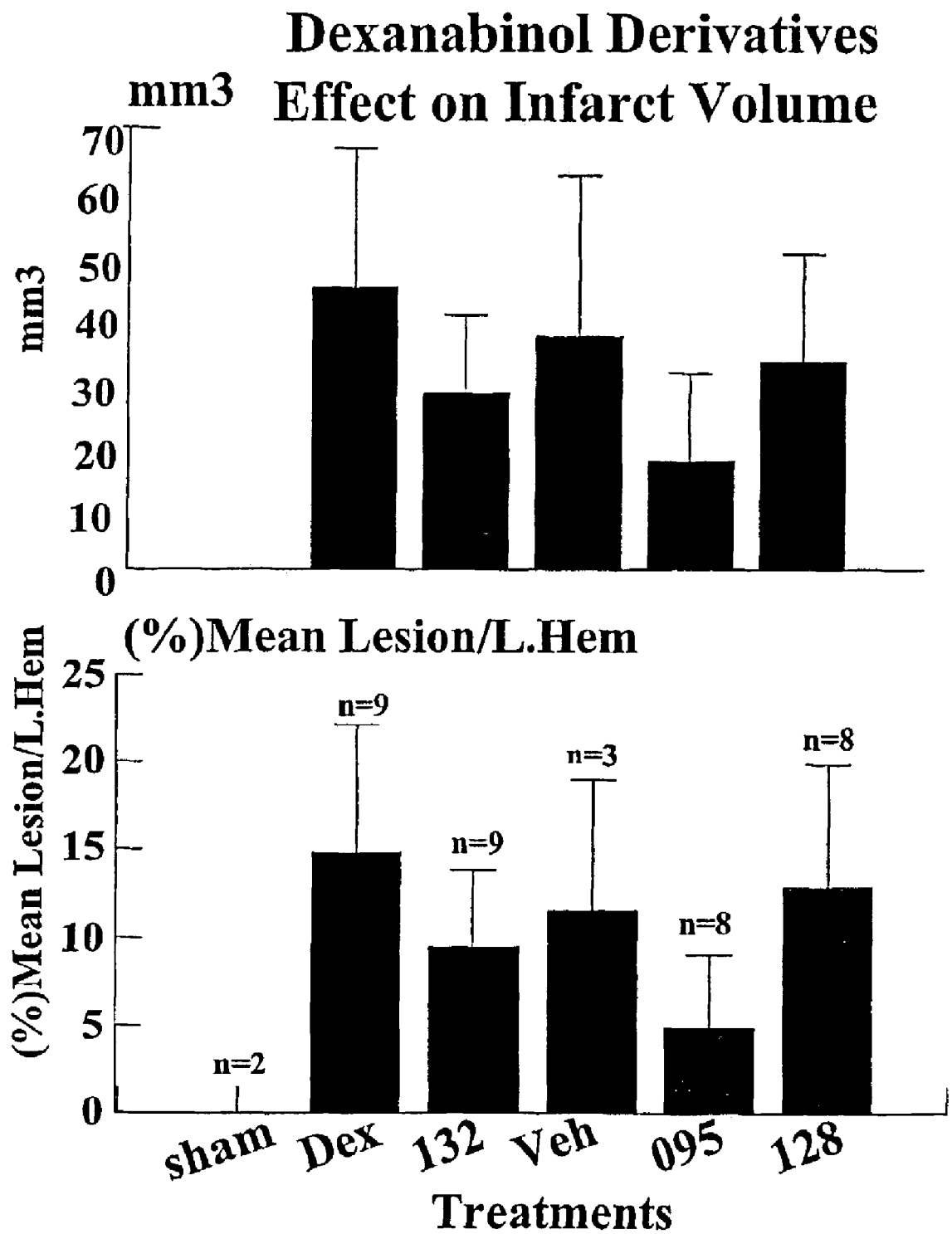
Figure 9:
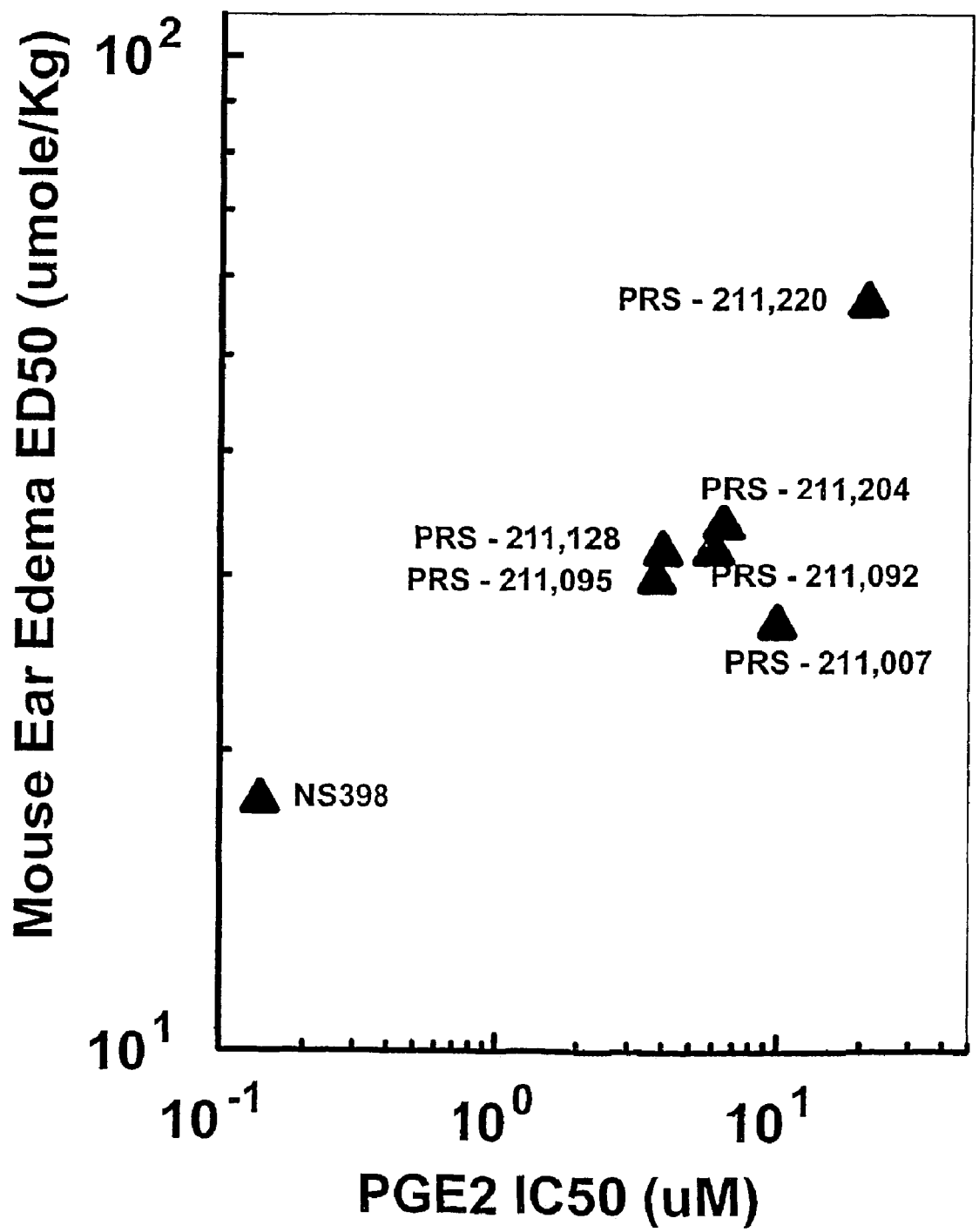
FIGS. 9–10 show the ED 50 of certain preferred dexanabinol derivatives in inhibiting inflammation as assessed in the standard ear edema test.
Figure 10:
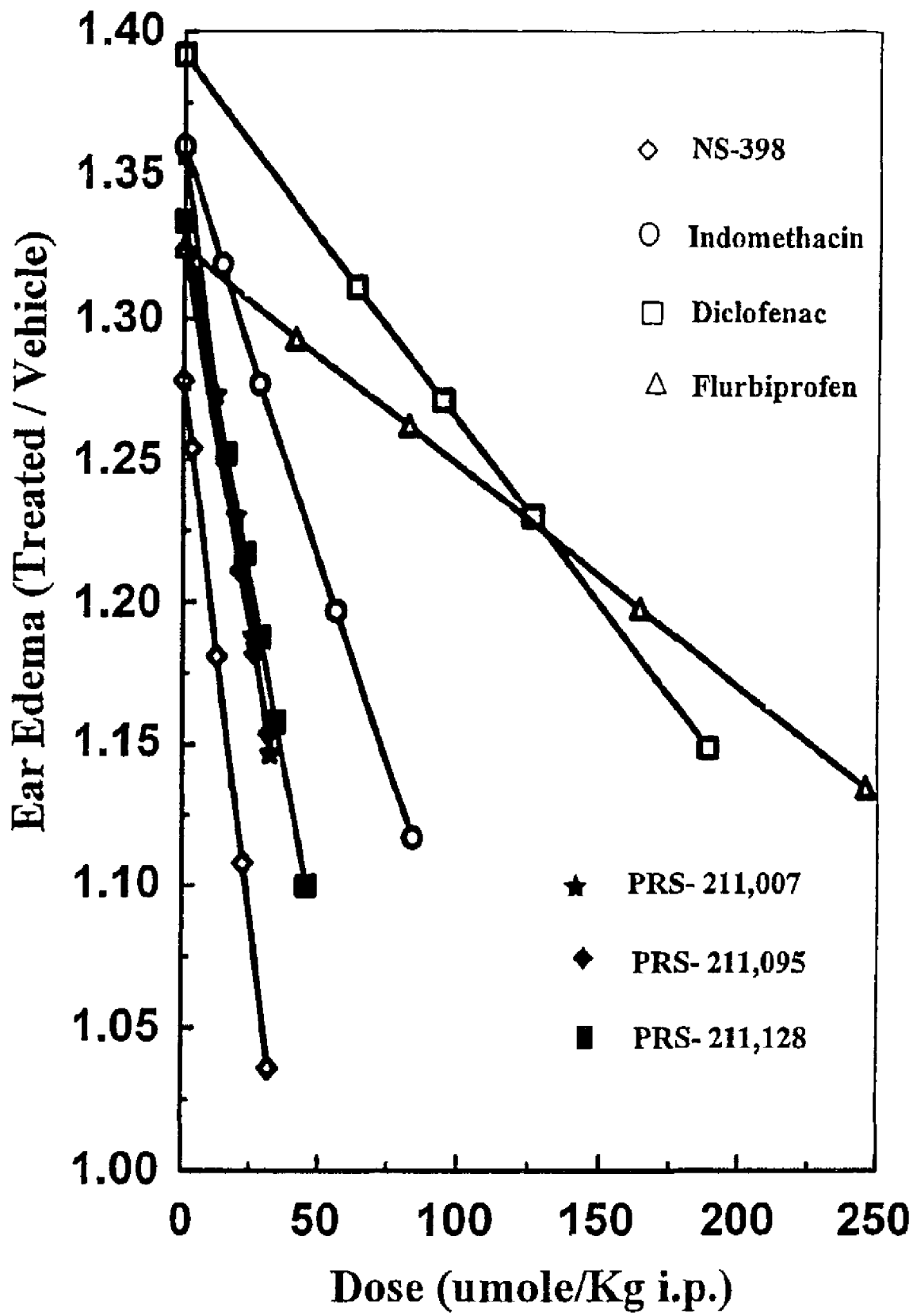

After we established the effect on edema, when given 30 minutes prior to, or right after, HT, we investigated the "therapeutic window," namely PRS-211, 25 mg/kg i.p. was given one, two or three hours after HT. Its effect on NSS (and on specific motor function) was assessed, as well as the effect on edema and BBB integrity. FIGS. 6–8 summarize the results of these studies. As can be seen, PRS-211 was fully effective, even when administered up to 2 h post-injury; at 3 h post-trauma the effect was less pronounced.

CONCLUSION

Severe head injury, or cerebral ischemia, is associated with a high mortality rate (exceeding 50%) and poor functional outcome. Despite extensive clinical and experimental research, there are no well-defined therapies for these conditions. There are very few available treatments for brain injury today and the gradual progressive biochemical changes that occur after head trauma can lead to the evolution of permanent neuronal damage. The results clearly demonstrate that the compounds of the instant invention, namely PRS-211 compounds possess cerebroprotective properties in a model of closed head injury.

Physiological Example 5

Neuroprotection by PRS-211 Compounds in Transient Middle Cerebral Artery Occlusion (MCAo), Infarct Size Evaluation Experimental Design.

The design was a randomized one, performed in a masked fashion as to whether drug or vehicle was being given, and an attempt was made to generate approximately equal numbers of drug- and vehicle-treated animals.

Materials
   a. Male rats (8/treatment group) 320–380 gr. (Harlan Israel).
   b. Halothane (Rhone Poulenc France)
   c. Pentobarbitone (Pental Veterinary, CTS Israel).
   d. Poly-L-Lysine (Sigma, USA).
   e. Silk suture material 3-0 and 4-0.
   f. Nylon (Polyamid) suture material 3-0. Four cm pieces were cut and positioned in a solution of 1% Poly-L-Lysine for 1 minute and dried in an oven (60 ° C.) for 60 minutes. The tip of each piece was rounded under a flame.
   g. Saline (Teva Medical).
   h. Blank cremophor ethanol cosolvent (Pharmos).
   i. Dexanabinol in cremophor ethanol cosolvent 50 mg/ml. (Both Dexanabinol and its vehicle were diluted in saline prior to drug administration.
   j. Analogs PRS-211,092, PRS-211,095, PRS-211,128 PRS-211,132 and PRS-211,220 in cremophor ethanol cosolvent, 50 mg/ml.
   k. The analogs were diluted in saline prior to drug administration.

Methods

Transient MCAo
   a. Surgical details of the MCAO method used for testing dexanabinol analogs, are presented in Belayev, et al., (Belayev, Busto, Weizhao, and Ginsberg, *Stroke* 26:2313–2319, 1995) which is incorporated herein in its entirety by reference.
   b. Two hours after the start of MCAo, the animals were reanesthetized with halothane, the neck wound was re-opened and the nylon thread pulled out of the Internal carotid artery (ICA). The skin wound was then closed with 3-0 silk suture material and the animals allowed to recover from the anesthesia.
   c. Three sets of animals were tested. In the first test immediately (2+0 hours) before thread removal the animals were injected IV with either analogs PRS 211,095, PRS 211,128, PRS 211,132, or Dexanabinol (PRS-211,007) each at a dosage of 5 mg/kg. One group of animals was treated with 5mi/kg vehicle alone. In another group, the animals subjected to "sham" operation, the suture was passed into the ICA, as described above, but immediately withdrawn. In the second set dexanabinol, PRS-211,092, PRS-211,095 and PRS-211,220 were used, at 2+0 hours. In the third set dexanabinol, PRS-211,092, PRS-211,095 and PRS-211,220 were administered 1 hour after thread removal (2+1 hours). Laser Doppler Flow (LDF) determined the success of MCAo—a drop of more then 50% in cerebral blood flow was considered as a sign of successful MCAO. Although LDF was a helpful corroborative sign, clinical outcome remained the final inclusion/exclusion criterion, since, with the exception of the PRS-211,220 staircase study, LDF was introduced only after initiation of the study.

Behavioral/Neurological Outcome Assessment

A detailed investigation of neurological performance was carried out on the first, third and the $7^{th}$ day after the MCAo. Two parameters were examined: posture and the flexion reflex (based on Nokon and Chuang, *NeuroReport* 9, 1998: 2081–2084). Animals were scored according to their performance:

Posture Score
   0—Normal
   1—Slight twisting
   2—Marked twisting
   3—Marked twisting and forelimb flexion Flexion Reflex Score
   0—Normal
   1—Slight deficit
   2—Moderate deficit
   3—Severe deficit Morphological Assessment of the Infarct Size One week after the ischemic insult, animals were euthanized with pentobarbitone 100 mg/kg IP. The animals were perfused through the heart with heparinized 4% formaldehyde solution in PBS (pH 7.4). Brains were then removed, and kept in the same solution before preparation for histological evaluation of the brain infarct volume.

Statistical Analysis

The infarct size was compared using ANOVA (analysis of variance) followed by Duncan's post hoc test.

Results a. Mortality Rate

No mortality was detected in the sham and 211,095 treated rats. A low mortality rate (9%) was seen in the Dexanabinol treated animals. The mortality rate among the other treatment groups (vehicle, 211,128 and 211,132) was similar (around 25%).

b. Behavioral/Neurological Outcome

Animals treated with analog PRS-211,095 demonstrated fewer neurological deficits and recovered faster compared to the other treatment groups.

c. Neuropathology

The means of the infarct volume and the percentage relative size to the contralateral hemisphere were least in animals treated with PRS-211,095, PRS-211,092 and PRS-211,220, the latter at 0.5 mg/kg, followed by the values in animals treated with 211,132. The reduction of infarct size was 60%, 52% and 48% for PRS-211,095, PRS-211,092 and dexanabinol (PRS-211,007), respectively.

CONCLUSIONS

These results show the novel analogs PRS-211,095, PRS-211,092 and PRS-211,220 are potent both in terms of preservation of function and reduction of brain lesion size after MCAo. These data can possibly be interpreted in the context of the relatively high affinity of PRS-211,095 and PRS-211,220 for the NMDA receptor as well as being potent inhibitors of COX-2. In contrast, PRS-211,128 has no detectable affinity for the NMDA receptor and was inactive in terms of function, reduction of mortality and brain morphometry. These structure-activity relationships suggest that affinity for the NMDA receptor is an important, but not the only, component for neuroprotection against ischemia. PRS-211,092 shows low affinity for the NMDA receptor and suggests that other, unidentified mechanisms are important for neuroprotection.

Physiological Example 6

Neuroprotection by PRS-211 Compounds in Transient MCAo: Evaluated by the Staircase Test.

The test challenges fine motor, sensory and stereognostic function of the cortex in enabling the forepaw (hand) to identify, grasp and accurately manipulate small objects such as food pellets. Loss of the ability to identify, grasp and manipulate small objects reflects a lesion of the fronto-parietal cortex and is a common and crippling deficit after stroke in humans.

Materials

The materials for this procedure are identical to those from Physiological Example 5, except for the different concentrations of PRS-211,095. The procedural differences are as follows:

Male Sprague Dawley rats, 230–270 gr (Harlan, Israel) were used. The following compounds and their respective concentrations were tested:

Dexanabinol and analogs PRS-211,095 and PRS-211,220 in PEG ethanol cosolvent 50 mg/ml. Dexanabinol, the analogs and their vehicle were diluted in Intralipid® 20% (Pharmacia) prior to drug administration.

Methods

1. Training for Functional Evaluation

The procedure is essentially as described in Montoya et al. (Montoya, Campbell-Hope, Pemberton and Dunnet, *J. Neurosci. Meth.* 36:219–228,1991) Animals were kept under mild food deprivation for 3–5 days, receiving 15-gr. food once a day (between 16:00 and 17:00) and free access to water.

Animals were trained prior to the test for 3–5 days according to the protocol of Sharkey et. al. (Sharkey, Crawford, Butcher and Martson, *Stroke* 27:2282–2286, 1996).

In brief, the staircase box contains two rows of seven stairs in each. Two 45 mg food pellets were placed on each step. Animals were placed in the box for 15 minutes sessions. At the end of the session the number of eaten (grasped) and displaced pellets was counted and recorded. Animals were tested twice a day, 4 hours apart. The first session was performed between 8–9 AM and second between 12–13 PM. The animals were trained until they grasped (ate) at least 8 pellets from each set of stairs for two consecutive sessions. Up to one week after the end of the successful training session the animals underwent transient MCAo.

Transient MCAO was performed in essentially the same manner as described in Physiological example 5 with the following modification at step i:

Two minutes prior to thread removal rats were re-anesthetized and administered IV with Dexanabinol 5 mg/kg, analogs PRS-211,220 or PRS-211,095 at 0.5, 2.5, 5 or 10 mg/kg or vehicle 5 ml/kg. One additional group was sham-treated.

2. Functional Assessment Following Transient Focal Ischemia

Animals were allowed to recover from the surgery for five days. The mild food deprivation was re-employed during the days following the ischemic insult. They were tested in the staircase box using the above method for 9–12 days. Animals were weighed twice a week during this period.

3. Morphological Assessment of the Infarct Size

At the end of the evaluation period, animals were euthanized with pentobarbitone 100 mg/kg IP. The animals were perfused through the heart with heparinized 4% formaldehyde solution in PBS (pH 7.4). Brains were then removed, and kept in the same solution for at least 24h. Then the brains—from the rostral side of the cortex to the cerebellum—were sunk in 30% sucrose in PBS, cryosectioned (20 µm), dried and stained with thionin for histological evaluation of the brain infarct volume. Eight sections at the levels of: 3.3;+2.8;+1.8; +0.8; −0.4;−1.4; −2.2; and −3.4 from Bregma were measured (Swanson, Rat Brain Atlas, 1992). Sections were captured by a CCD camera (V-tech MP-470) and image analyzed (Scion image 1.62A). Infarct size was determined from the series of the 8 sections by either calculation of the infarct volume (mm3) by summing the series of mean lesion areas of two adjacent sections multiplied by the distance between them or calculation of the mean infarct size as percentage of the contralateral hemisphere size; calculation of the mean of the surviving ipsilateral side as percentage of the contralateral hemisphere size; calculation of the mean ipsilateral side ventricle as percentage of the contralateral hemisphere ventricle.

Statistical Analysis a. The infarct size was compared using ANOVA (analysis of variance) followed by Duncan's post hoc test.

b. The staircase task performance was evaluated after collecting the data and compressing it into four blocks of six trials:

First block—The last day of preoperative testing

Second block—Tests from day 6, 7 and 8 post ischemic insult

Third block—Tests from day 9, 10 and 11 (or 12 or 13) post ischemic insult (a pool of the second 3 days)

Fourth block—Tests from day 14–18 post ischemic insult c. Data were analyzed using ANOVA (analysis of variance) followed by Tukey's post hoc test.

Results a. Physiological Parameters

No differences in the two measured physiological (blood glucose and rectal temperature) among the different treatment groups or at different treatment times were detected.

b. Mortality Rate

Mortality in the present study was low as can be seen in Tables 4 and 5.

TABLE 4

Mortality rate for PRS-211,095 treated animals

| Treatment | N | No. Dead Animals | Mortality Rate(%) |
|---|---|---|---|
| Sham | 13 | 0 | 0 |
| Vehicle | 13 | 1 | 8 |
| Dexanabinol 5 | 8 | 0 | 0 |
| 211,095 0.5 | 14 | 3 | 21 |
| 211,095 2.5 | 10 | 3 | 30 |
| 211,095 5 | 9 | 0 | 0 |
| 211,095 10 | 11 | 1 | 9 |

TABLE 5

Mortality rate for PRS-211,220 treated animals

| Treatment | N | No. Dead Animals | Mortality Rate (%) |
|---|---|---|---|
| Sham | 18 | 0 | 0 |
| Vehicle | 25 | 4 | 16 |
| 211,220 0.1 | 16 | 4 | 25 |
| 211,220 0.5 | 16 | 3 | 18.75 |
| 211,220 2.5 | 13 | 4 | 30.7 |
| 211,220 5 | 14 | 2 | 14 |
| Dexanabinol 0.5 | 11 | 4 | 36 | b. Body Weight Gain

Animals were kept under mild food deprivation during the staircase testing (except during weekends). Under these conditions, the following results were observed:

Sham and PRS-211,095 10 mg/kg treated rats gained the maximal body weight (15 and 17% respectively compared to base line). This was statically different (p<0.05) from vehicle-treated rats, which did not gain weight at all. (They even lost 4% of their body weight) Dexanabinol and PRS-211,095 (both 5 mg/kg) and PRS-211,220 0.1, 0.5, 2.5 and 5 mg/kg treated rats demonstrated a moderate body weight gain (7 and 4% for PRS-2 11,095 and 3, 10, 5 and 4% for PRS-211,220, respectively). These differences were not statistically different. The other groups (PRS-211,095 0.5 and 2.5 mg/kg) did not gain weight.

C. Staircase Test Performance

No significant differences in the ipsilateral performance were observed among the different treatment groups. The mean number of pellet consumption was between 8–11 per test. There was a slight decrease in pellet consumption detected in all treatment groups during the first session following the ischemic insult (the end of the first week post insult). This decrease was transient and disappeared during the next sessions.

A marked impairment was evident in the vehicle-treated rats for contralateral performance. Pellet consumption was reduced to less than 3 in the first session following the ischemic insult. This went up to 5 pellets in the third session. PRS-211,095 treated rats demonstrated an improved performance in a dose-related manner. PRS-211,095 0.5 and 2.5 mg/kg treated animals showed moderately improved pellet consumption, while the 5 and 10 mg/kg dose levels demonstrated a robust improvement (p<0.05 compared to vehicle).

Dexanabinol 5 mg/kg had a similar effect. PRS-211,095 5 mg/kg was superior to the 10-mg/kg dosage and to the Dexanabinol only in session 1. No improvement was detected in the Dexanabinol 0.5 mg/kg treated rats. PRS-211,220 treated rats demonstrated an improved performance in a dose-related manner. PRS-211,220 0.1 2.5 and 5.0 mg/kg treated animals showed moderately improved pellet consumption (20–30% improvement over vehicle), while the 0.5 mg/kg dose level demonstrated a robust improvement (more then 60% relative to that of vehicle alone: p<0.05). The best performance in the last session (session no. 3) was seen with PRS-211,220 0.5 mg/kg.

Figure 11:
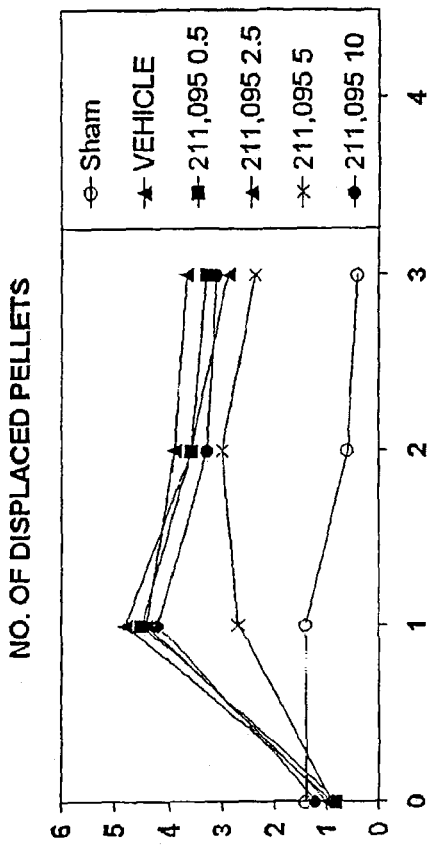
FIG. 11 A–B illustrate the improvement in contralateral performance in animals treated with certain preferred dexanabinol derivatives as assessed in the Staircase test.
Figure 11:
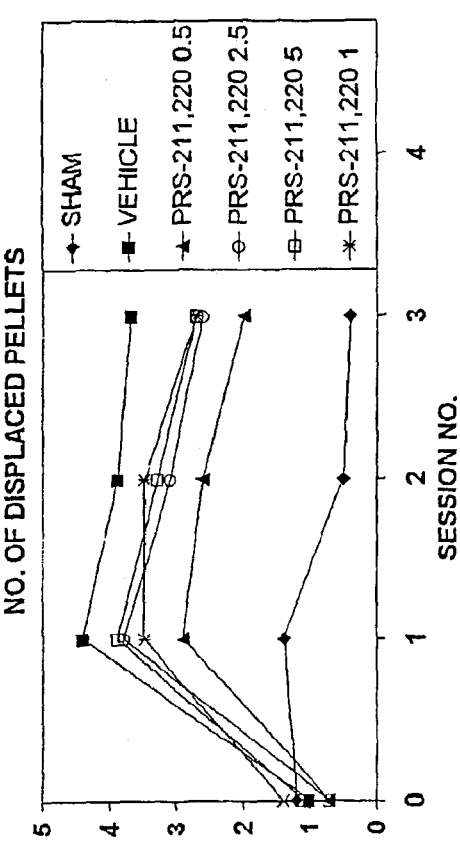
Figure 11:
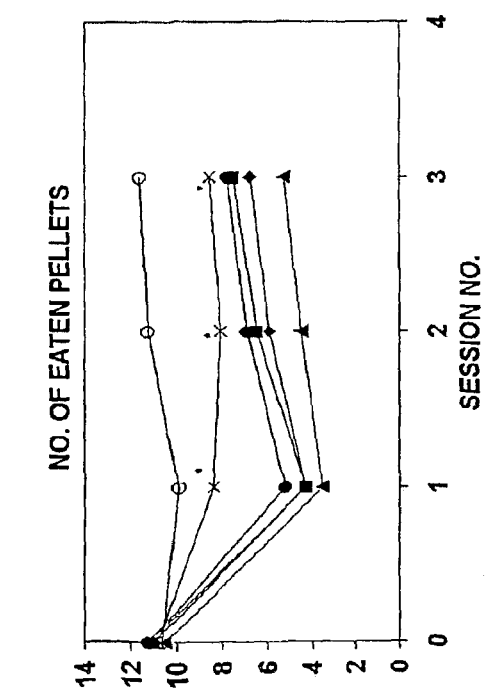
Figure 11:
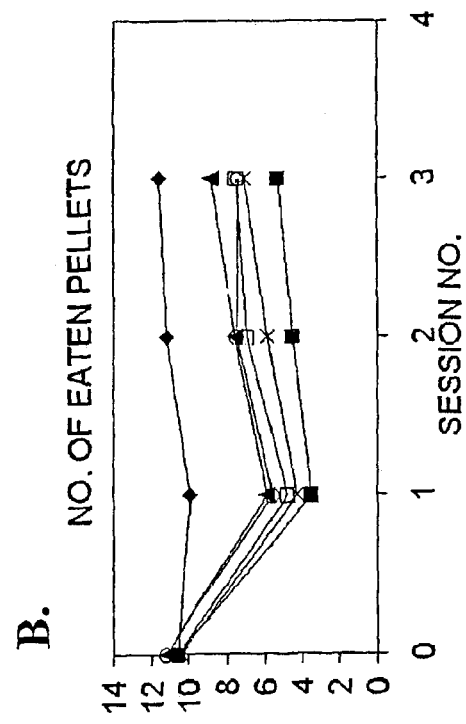

A similar phenomenon was detected in the displaced pellets parameter. The vehicle-treated rats displaced the highest number of pellets, while the sham-operated rats displaced the least. PRS-211,095 and Dexanabinol 5 mg/kg and PRS-211,220 0.5 mg/kg induced an improved performance similar to that seen in the previous parameter FIG. 11 depicts contralateral performance in the staircase test. A. Results for PRS-211,095 pellets eaten and pellets displaced and B. Results for PRS-211,220 pellets eaten and pellets displaced.

e. Histopathology

Figure 12:
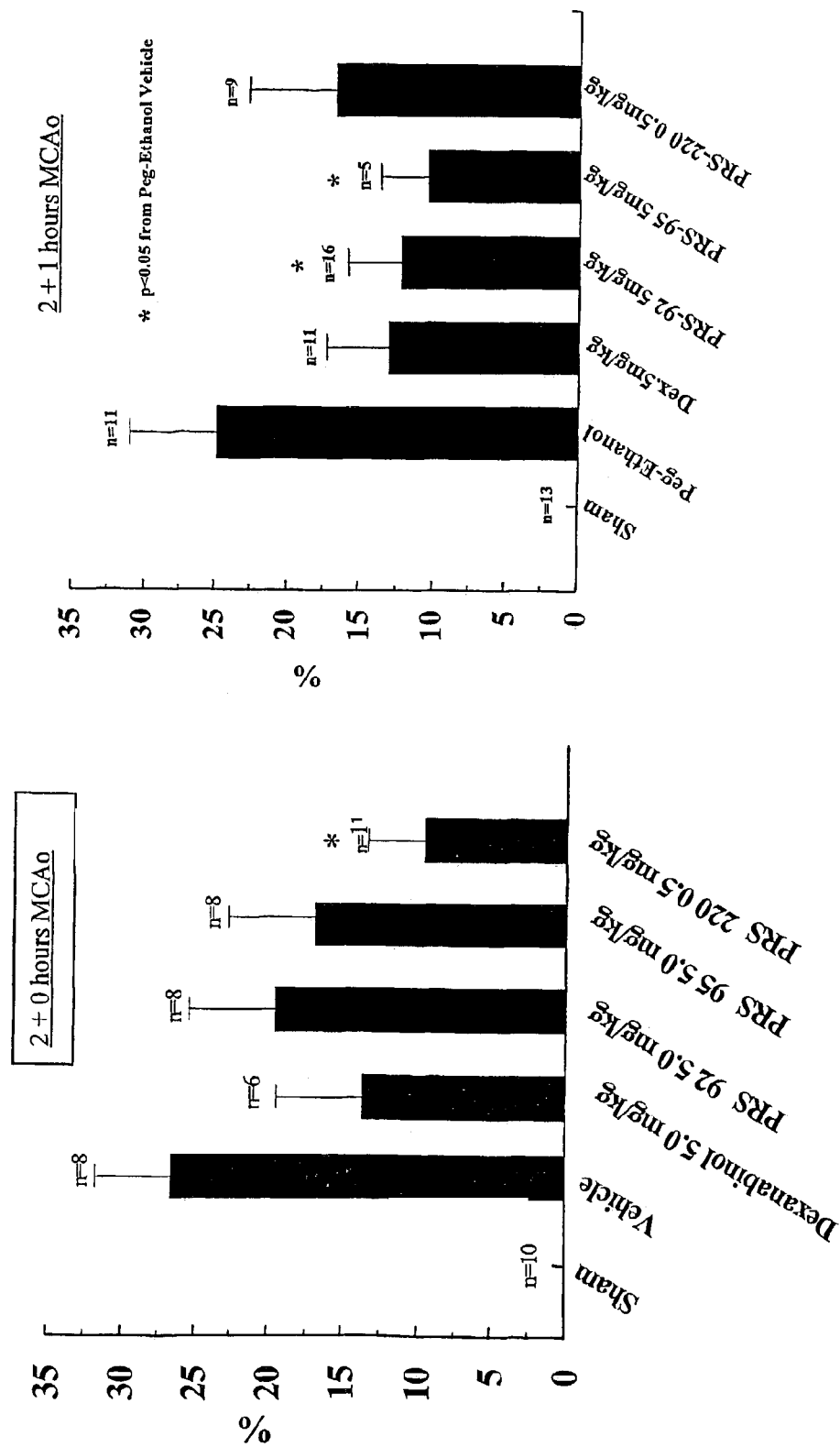
FIG. 12 shows the change in cerebral infarct size in animals treated with certain preferred dexanabinol derivatives as assessed in the transient MCAo test.

7–8 animals in 3 treatment groups underwent histopathological analysis: Dexanabinol 5 mg/kg, PRS-211,095 2.5 and 5 mg/kg. Under the treatment conditions, Dexanabinol and PRS-211,095 5 mg/kg reduced the infarct volume by 35% compared to vehicle. This effect was not statistically different. No protection was seen with any other dosage. FIG. 12 shows the change in cerebral infarct size in animals treated with certain preferred dexanabinol derivatives as assessed in the transient MCAo test. The left panel shows results of preferred PRS-211 compounds in the 2+0 hour assay, where the preferred compounds were administered immediately upon MCAo completion. The right panel shows results of preferred PRS-211 compounds in the 2+1 hour assay.

CONCLUSIONS

First, when administered 2 hours post-injury, analog PRS-211,095 and dexanabinol demonstrated similar neuroprotection following 120 minutes of transient MCAo. This was evident from the contralateral performance in the staircase as well as from the reduction in infarct size. PRS-211,220 at 0.5 mg/kg had the most potent effect in session 3 of the staircase. This is at least 10 times more potent than PRS-211,095 and dexanabinol. Second, all dose levels of PRS-211,095 demonstrated improved performance in the staircase test, but the best activity was seen with the 5 mg/kg dose. It is worth noting that PRS-211,220 at the 0.5 mg/kg dose performs better than PRS-211,095 or dexanabinol, both at a 5 mg/kg dose. The histopathological evaluation revealed that both Dexanabinol and analog PRS-211,095 (both at the 5 mg/kg dose) reduced the infarct size by 35% (compared to vehicle).

Additional experiments have shown that when the compounds were administered 3 hours, instead of 2 hours, following transient MCAo, they still retained neuroprotective activity as expressed by the number of pellet eaten in the staircase test, with an increase in consumption of 58% for animals treated with 5 mg/kg PRS-211,092; 27% for animals treated with 0.5 mg/kg PRS-211,220 and 17% for animals treated with 5 mg/kg PRS-211,095 in session 3.

Further experiments when the compounds were administered 6 hours following transient MCAo, confirm the potent neuroprotective activity of compounds of the invention and their impressive therapeutic window. In this experimental setup, treatment with 5 mg/kg of PRS-211,092 increased the consumption of pellet by 30% while treatment with 0.5 mg/kg of PRS-211,220 yielded an increase of 40% in session 3.

Physiological Example 7

Neuroprotection by Dexanabinol Analogs in the MPTP Model of Parkinson's Disease (PD)

The MPTP-mouse model of Parkinson's disease is used to test the efficacy of the compounds to prevent the onset of PD symptoms.

Materials
a. 190 g, eight week old male C57/BL mice (Harlan Israel).
b. MPTP-HCl (Sigma USA).
c. Saline (TevaMedic Israel).
d. Rat antibody against MAC-1 or F4/80 (Serotec).
e. Rabbit anti-GFAP (Sigma).
f. Rabbit anti- e,n or iNOS (Serotec)
g. Sheep anti-Tyrosine Hydroxylase (TH) (Calbiochem).
h. Secondary antibodies (Zymed)
i. Pentobarbitone sodium 200 mg/m (CTS Israel).
j. Heparin (500 IU/ml, Chaoi France).
k. 4% formaldehyde buffer solution (Frutarom Israel).

Methods

The protocol is based on Liberatore et al. (Liberatore, Jackson-Lewis, Vukosavic, Mandir, Vila, McAuliffe, Dawson, Dawson and Przedborski, *Nature Medicine* 5:1403–9, 1999).

The treatment groups are as follows:
Vehicle 5 ml/kg IP once just before MPTP administration.
Dexanabinol or analog 10 mg/kg IP once just before MPTP administration.
Dexanabinol or analog 20 mg/kg IP once just before MPTP administration.
Dexanabinol or analog 20 mg/kg IP once just before MPTP administration+additional dose 24 hours later.

Table 6 depicts the experimental strategy followed to determine the most effective treatment in the MPTP model. 19 groups of animals are treated as follows:

TABLE 6

| Days post MPTP | | | TREATMENTS | | | |
| --- | --- | --- | --- | --- | --- | --- |
| 24 hours | MPTP | Saline | MPTP + Dex (10 mg) | MPTP + Dex (20 mg) | MPTP + Dex (30 mg) | MPTP + Dex (20 mg × 2) |
| 3 days | MPTP | Saline | MPTP + Dex (10 mg) | MPTP + Dex (20 mg) | MPTP + Dex (30 mg) | MPTP + Dex (20 mg × 2) |
| 7 days | MPTP | Saline | MPTP + Dex (10 mg) | MPTP + Dex (20 mg) | MPTP + Dex (30 mg) | MPTP + Dex (20 mg × 2) |
| Naive | | | | | | |

Dex = dexanabinol or analog

Results:

Seven days after MPTP administration the mice were euthanized and their brains removed cut and stained using an antiserum to tyrosine hydroxylase (TH-IR), the rate limiting enzyme in monoamainergic neurons. Attention was focused on the Substantia nigra, pars compacta (SNpc), which are comprise of dompaminergic neurons that project to the striatum. It is these neurons that undergo degeneration in Parkinson's Disease. MPTP acts as a specific neurotoxin for these neurons, and the aim was to determine whether MPTP-induced nerve degeneration could be ameliorated by Dexanabinol at 10 (D-10), 20 (D-20) or 30 (D-30) mg/kg, or 2 injections of Dexanabinol at 20mg/kg (D-20×2) relative to vehicle alone (V). The results show that MPTP induced a massive decrease in the number of TH-IR neurons in the SNpc relative to that in animals treated with vehicle alone, and that this decrease was significantly reduced by Dexanabinol at 20 and 30 mg/kg.

The rescue effect of the various treatments was calculated by comparing the number of the TH-IR cells in each group relative to that in animals treated with MPTP alone, which was arbitrarily assigned a value of zero. The data in Table 7 show that the maximal protective effect of Dexanabinol was obtained at 20 mg/kg.

TABLE 7

| Treatments | TH-IR SNpc |
| --- | --- |
| MPTP | 0 |
| V | −0.19 |
| D-10 | −7.85 |
| D-20 | 28.52 |
| D-30 | 22.73 |
| D-20x2 | 8.5 |

Physiological Example 8

Optic Nerve Crush Model

The novel compounds are tested in an Optic Nerve Crush model to determine their effects in axonal survival and regeneration.

Materials
a. Adult, male Sprague Dawley rats 350–550 gr. (Harlan Israel).
b. Dexanabinol or analogs 5% in Cremophore Ethanol (Pharmos).
c. Blank Cremophore Ethanol (Pharmos).
d. Pentobarbitone (Pental Veterinary, CTS, Israel) 1 mg/kg, 1:5 with Saline
e. Xylazine (Vitamed) 1 mg/kg, 1:5 with Saline
f. Antibodies:Mab anti-Gap43 (Sigma, G-9264) Anti-GFAP (Sigma)

Methods

The methodology is as described in Duvdevani et al., (Duvdevani, Rosner, Belkin, Sautter, Sabel, and Schwartz, *Rest. Neurol. Neurosci.* 2:31–38, 1990).

Evaluation of Optic Nerves

At the end of the experiment (8 weeks) the animals are deeply anesthetized with pentobarbitone 60 mg/kg IP and cardially perfused with 4% heparinized formaldehyde solution. The eye and the optic nerves from the globe to the chiasm are removed and further fixed by immersion in 4% paraformaldehyde overnight. The optic nerves (from the globe to the chiasm) and the brains (the areas of the lateral geniculate body and the superior colliculus) are cryoprotected in 30% sucrose, frozen and sectioned (serial sections: Optic nerves—longitudinal, 16 µm; Brains-coronal 30 µm). Retinas are prepared as whole mounts. The retinas and sections are immunohistochemically stained with anti-GAP-43 and anti-GFAP. GAP-43 is an acidic, axonally transported membrane protein present in the CNS and PNS whose presence is indicative of regenerative growth (Skene and Willard, *J Neurosci* 1:419–26 1981) while GFAP, Glial fibrillary acidic protein, is a marker for astrocytes.

GAP-43 positive labeling indicates regenerative growth while GFAP positive labeling is indicative of glial scar formation.

Treatments demonstrating positive labeling for GAP-43 are repeated and processed for electron microscopy analysis. The number of viable axons in each treatment, as a measure for neuroprotection and the number of unmyelinated, thinly myelinated axons and growth cones, as a measure of regeneration, are compared in a cross section, 1 mm distal from the site of injury. In animals demonstrating regenerative growth, we measure the length of regenerating axons.

Physiological Example 9

Rat Model of Myocardial Ischemia

The following model of myocardial infarction and heart failure was used to test the ability of compounds to reduce the volumes of infarction is considered a measure of their potential as cardioprotectors.

Materials and Methods

The methods used are essentially as described in Leor and Kloner (Leor and Klonner, Am. J Cardiol. 75:1292–3 1995). The experiment was performed in a masked fashion. In brief, Sprague-Dawley rats were given either vehicle or PRS-211,095 15 minutes before occlusion. They were subjected to 45 minutes of coronary occlusion and 4 hours of reperfusion, after which the coronary artery was reoccluded and 0.25 ml of Unisperse™ dye was injected IV to determine area of risk (AR). The rats were euthanized and hearts were analyzed as to infarct size using a 1% solution of triphenylteuazolium chloride for 15 minutes at 37° C. The area of necrosis (AN) in each heart was expressed as a percentage of the area at risk. This was multiplied by the weight of each slice to obtain the mass of tissue at risk and necrosis.

RESULTS AND CONCLUSIONS

Figure 13:
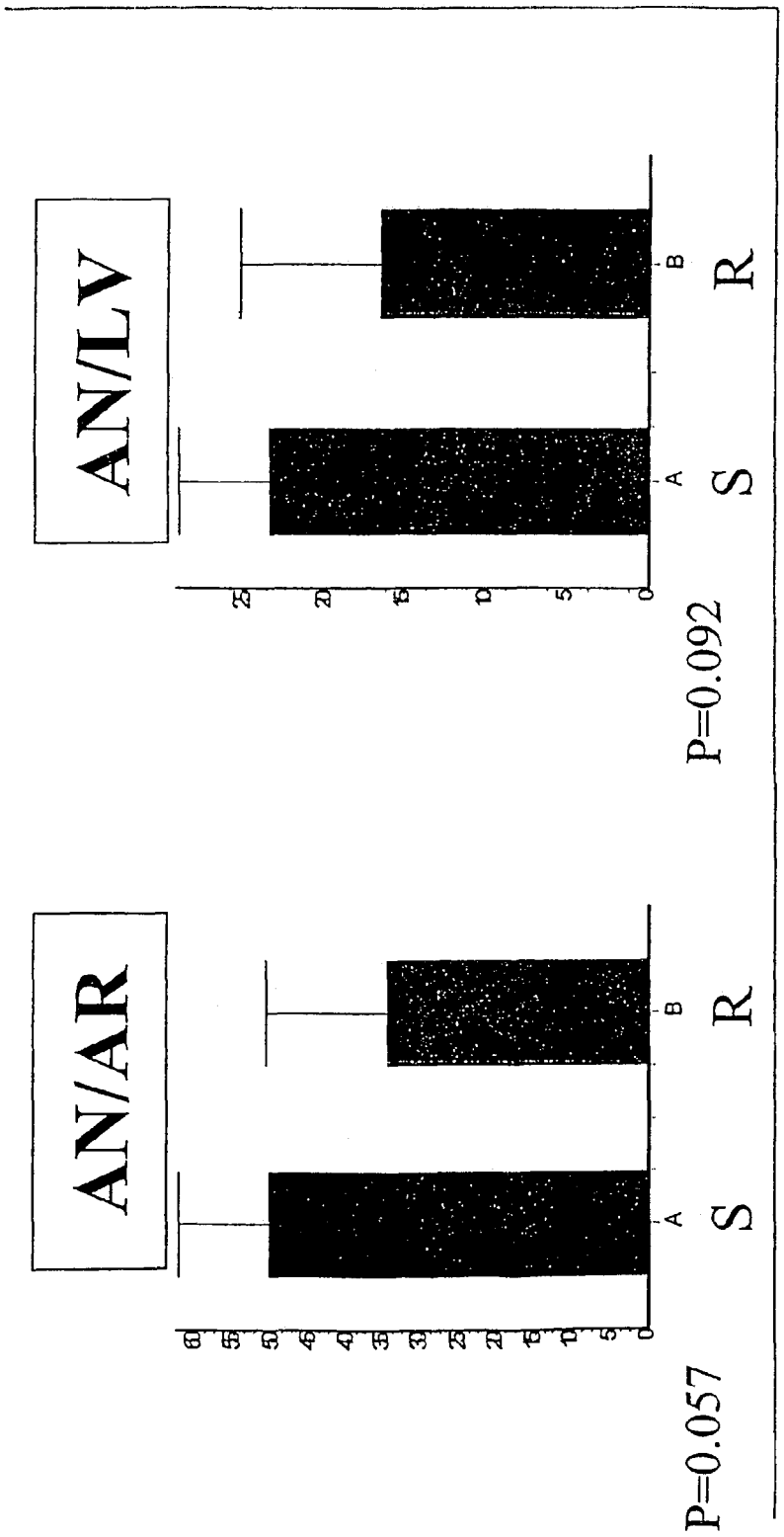
FIG. 13 depicts the change in necrotic area in animals treated with certain preferred dexanabinol derivatives as assessed in the myocardial ischemia model.

FIG. 13 shows the area of necrosis per area of risk (AN/AR) for R (PRS-211,092) and S (vehicle) and the area of necrosis of the left ventricle (AN/LV). The Y axis measures the effect on infarct volume in $mm^3$. There is a clear decrease in infarct size in the dexanabinol derivative treated animals.

Physiological Example 10

The Tail Flick Model: Analgesic Effect and Reversal of Tolerance.

The following animal model of acute pain was used to assess the potential analgesic effects of test compounds either alone or in combination with morphine. Moreover, the effect of the compounds was tested both on naïve animals and on animals that have developed tolerance to a previous opioid treatment. In this model the nociceptive stimulus is thermal and the latency time till the animal flicks its tail is monitored (Le Bars D., Gozariu M. & Cadden S. W., Pharmacol. Rev. 53: 597–652, 2001).

Materials and Methods

Hyperalgesia to radiant heat was assessed as follows. ICR male mice (20–30 g average body weight, Harlan, Israel) were injected with test compounds i.p. at the volume dose of 5 ml/kg. Each treatment group contained at least 6 animals. The test compounds were dissolved in Cremophor®:ethanol (70:30 weight/weight) and diluted 1:20 in saline prior to injection. Morphine HCl was directly dissolved in saline. Its vehicle was also included as control. Pain threshold was determined 30 minutes post-administration by measuring the foot-withdrawal latency defined as the time from the onset of radiant heat to foot withdrawal. The cut-off time was preset to 10 seconds in order to prevent tissue damage. To assess the effect of preferred compounds on development of tolerance to opioid, tolerance was induced by twice daily i.p. injections of 10 mg/kg morphine, 4 hours apart from one another. Test compounds (5 mg/kg) and vehicle (5 ml/kg) were administered 15 minutes before morphine and pain threshold was determined 30 minutes after the first injection of morphine on day 1, 5, 8 and 10. To assess the effect of preferred compounds on reversal of tolerance to opioid, tolerance was first established by twice daily i.p. injections of 5 mg/kg morphine, 5 hours apart from one another, for a period of 10 days. Pain threshold was determined on day 1 and 10. On day 10 the animals that did not show analgesia in response to morphine were divided into the three groups, and the different treatments were administered starting day 11. Once tolerance has developed test compounds (5 mg/kg), Dextromethorphan (20 mg/kg) and vehicle (5 ml/kg) were administered 15 minutes before morphine and pain threshold was determined 30 minutes after the second injection of morphine on day 12, 15 and 17.

In each type of study, the animals were tested on given days 30 minutes after morphine injection in the tail flick apparatus (Socrel, model DS 20). Animals were gently held while their tails were located above the photoelectric cell. The tails were then illuminated (21V) at 2 cm from the distal tip and the latency time, measured in seconds, was recorded in duplicates. The results are expressed either as absolute latency time or as percent of animals that enjoyed significant analgesia as measured by the fact that their latency time is at least twice the latency time for vehicle treated animals. At the end of the study, the animals were euthanized by i.p. injection of 100 mg/kg sodium pentobarbitone.

The differences between the latency times among various treatment groups was analyzed by analysis of variance (ANOVA) followed by post-hoc Duncan test. The differences between the % of animals showing analgesia among various treatment groups was analyzed by analysis of variance (ANOVA) followed by post-hoc Fisher exact test. A value of $p<0.05$ is considered to be statistically significant.

RESULTS AND CONCLUSIONS

In the plain analgesic study, animals treated with either vehicle displayed an identical latency time of 2.8 sec. Administration of 5 mg/kg morphine reduced the hyperalgesia as monitored by a significantly longer latency time of 7.5 sec. PRS-211,092, PRS-211,095 and PRS-211,220 administered separately at escalating doses of up to 10 mg/kg had no significant analgesic activity as expressed by latency times similar to baseline.

Figure 14:
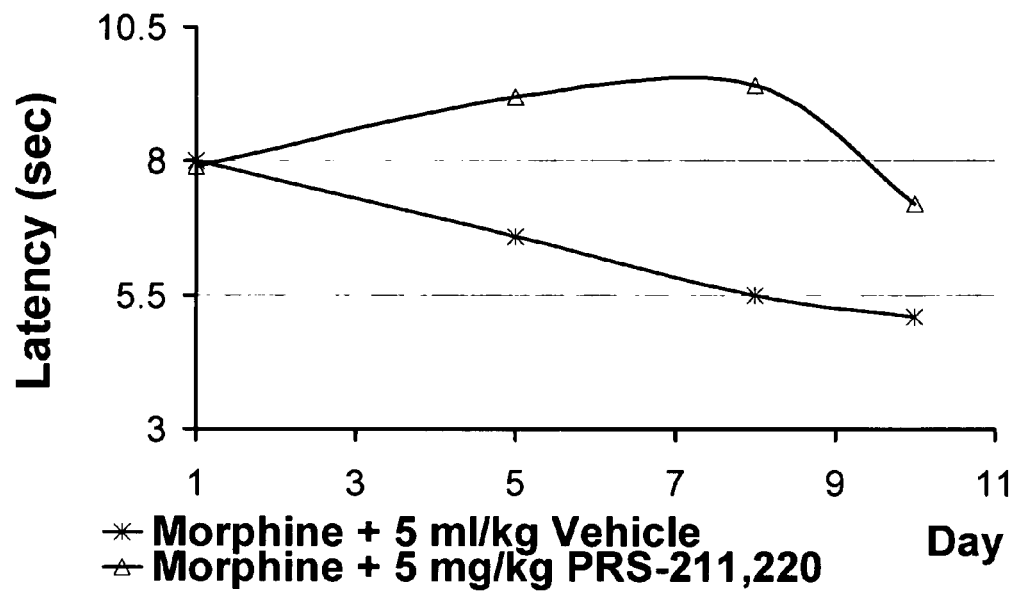
FIG. 14 A–D show the effect of certain preferred dexanabinol derivative on tolerance toward morphine.
Figure 14:
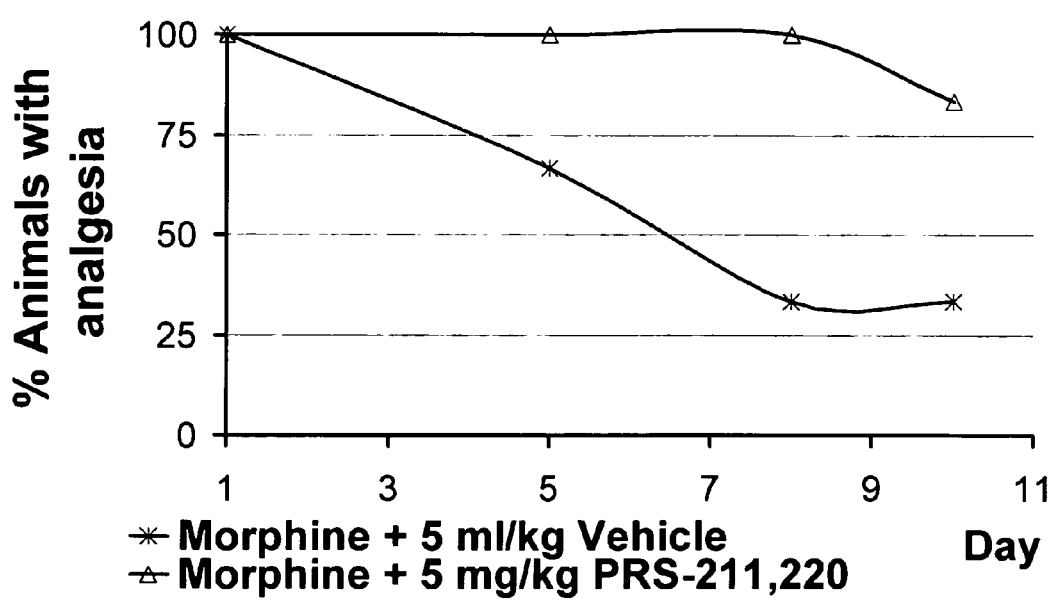
Figure 14:
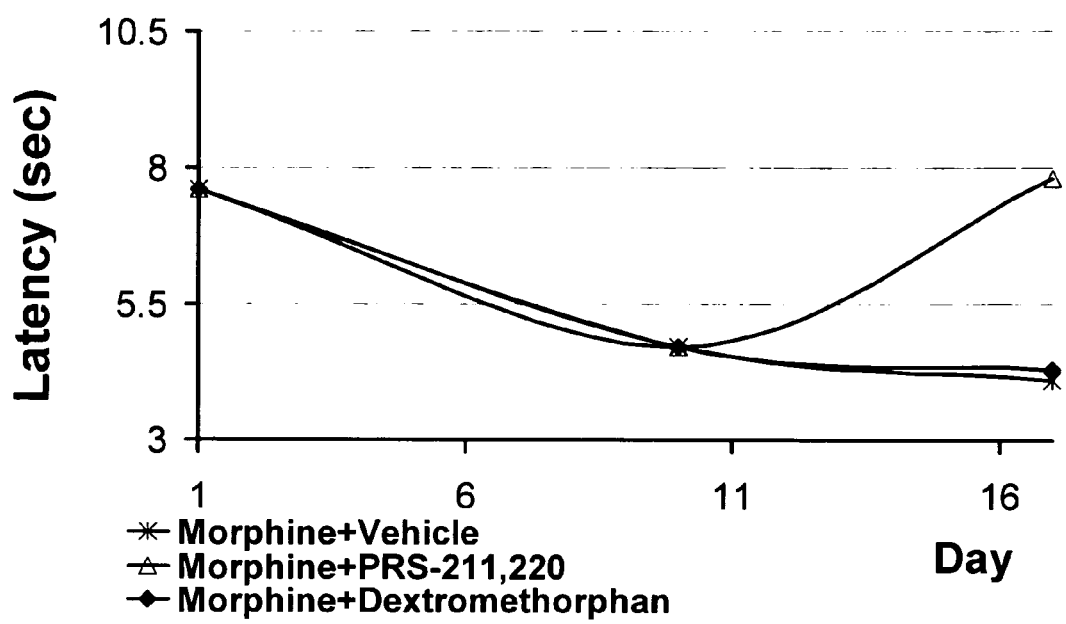
Figure 14:
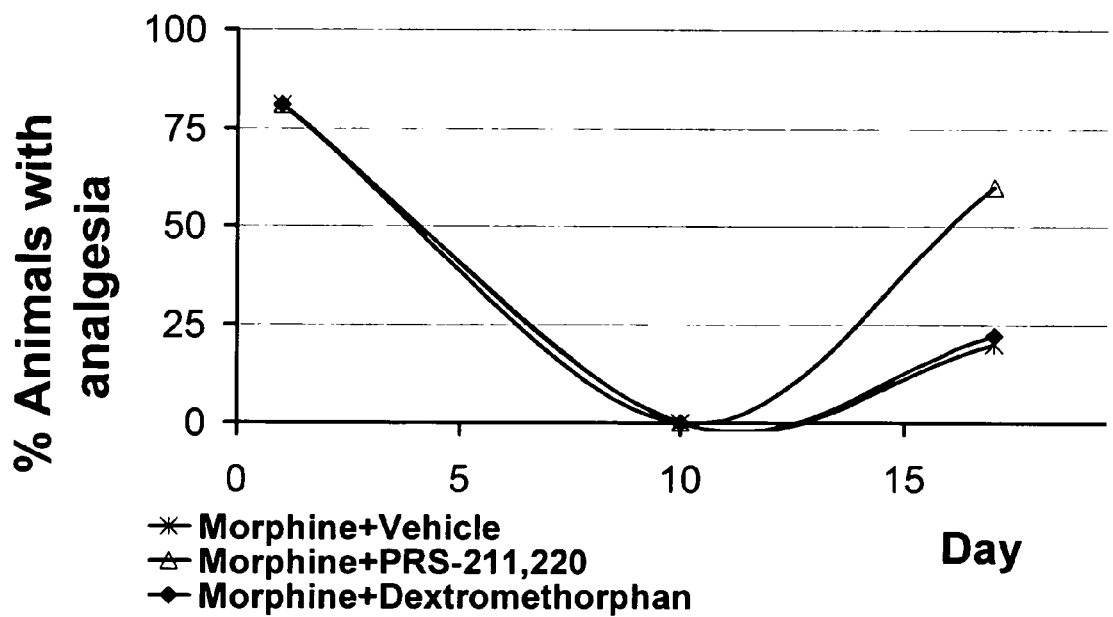

However, when PRS-211,220 was given in combination with 10 mg/kg i.p. morphine over a period of 10 days it was shown that preferred compound of the invention are effective in reducing the development of tolerance toward opioid. FIG. 14 shows the effect of PRS-211,220 on tolerance to morphine. Panels A and B show the effect of the test compound on development of tolerance, while panels C and D show the effect on reversal of established tolerance. In panel A and C the results are expressed in latency time as measured at predetermined days, in panel B and D the results are expressed as percent of animals showing analgesia, i.e. animals that display latency time at least twice higher than the latency time of vehicle treated animals. As can be seen from FIGS. 14A and 14B, animals treated only with morphine develop tolerance as indicated by the steady decrease in latency time and % of animals showing analgesia over the duration of the study. On the other hand, animals treated with morphine in combination with PRS-211,220 displayed a much more stable protection from pain, as indicated by relatively constant latency times and % of animals showing analgesia over the first 8 days of the study. Addition of PRS-211,220 to morphine is statistically significant on both parameters at day 8, while at day 10 the % of animals showing analgesia is still significantly higher in the combined treatment over the morphine treatment. The effect of PRS-211,220 on morphine potency along time is synergistic since PRS-211,220 has no effect of its own in this experimental model. Such results indicate that compounds of the invention are effective in preventing the clinically undesirable development of tolerance toward opioids such as morphine.

These encouraging results compelled the assessment of compound activity in a more challenging model, also of clinical relevance, and the effect of PRS-211,220 was tested on reversal of established tolerance. As can be seen from FIGS. 14C and 14D, on day 10 tolerance to morphine is well established as indicated by the lower latency time and the fact that none of the animals exhibited increased latency twice above baseline. Animals that continued to be treated only with morphine reached a plateau as far as latency times are concerned A slight increase in % of animals showing analgesia is observed at the end of the study on day 17, probably indicating some minor spontaneous reversal. Animals that were treated in combination with 20 mg/kg of the known NMDA antagonist dextromethorphan displayed a very similar pattern statistically undistinguishable from morphine alone. On the other hand, animals treated with morphine in combination with PRS-211,220 displayed a trend of reversal at all time points tested which became statistically significant on day 17. On day 17 the latency time displayed by animals treated with morphine in combination with PRS-211,220 was back to the original value of day 1 before the induction of tolerance providing thus maximal protection from pain. The % of animals showing analgesia at the end of the study is slightly below the original value on day 1, but this difference is not statistically significant. Such results indicate that compounds of the invention are not only effective in preventing the clinically undesirable development of tolerance toward opioids such as morphine, but are also efficient in reversing established tolerance.

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

What is claimed is:
1. A compound of the general Formula (I):

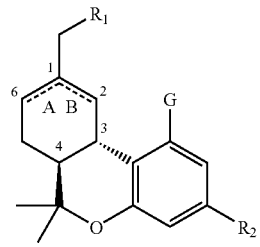

having the (3S,4S) configuration and being essentially free of the (3R,4R) enantiomer, wherein A—B indicates an optional 1(2) or 6(1) double bond, $R_1$ is
A) $R_3$ where $R_3$ is selected from the group consisting of
 a) a linear or branched, saturated or unsaturated, carbon side chain comprising 1–8 carbon atoms and 1–3 heteroatoms, at least one heteroatom being placed between two carbon atoms; or
 b) a saturated or unsaturated cyclic moiety or an aromatic or heterocyclic moiety having from 5–20 atoms comprising one or two-ringed structures, wherein each ring comprises 3–8 carbons and 0–4 heteroatoms,
 said heteroatoms each independently selected from the group consisting of N, O, and S; wherein each ring optionally is further substituted with one or more groups selected from
  i) $C_{1-6}$ alkyl,
  ii) $C_{1-6}$ alkoxy,
  iii) $C_{1-6}$ alkylthio,
  iv) halo,
  v) carboxyl,
  vi) —$CO_2$—$C_{1-4}$ alkyl,
  vii) keto,
  viii) nitro, and
  ix) a saturated or unsaturated cyclic moiety, or an aromatic or a heterocyclic moiety having from 5–20 atoms comprising one or two ringed structures, wherein each ring comprises 3–8 carbons and 0–4 heteroatoms, said heteroatoms each independently selected from the group consisting of N, O, and S;
   wherein each ring optionally is further substituted with one or more groups selected from i)-viii) as defined above;
B) an amine or an amide substituted with at least one substituent as defined in $R_3$ above;
C) a thiol, a sulfide, a sulfoxide, a sulfone, a thioester or a thioamide optionally substituted with one substituent as defined in $R_3$ above; or
D) an ether—$OR_3$ wherein $R_3$ is as defined above;
G is (a) halogen, (b) $C_1$–$C_6$ alkyl, or (c) —OR wherein R is (a') —R", wherein R" is hydrogen or $C_1$–$C_6$ alkyl optionally containing a terminal —OR'" or —OC(O)R'" moiety wherein R'" is hydrogen or $C_1$–$C_6$ alkyl, or (b') —C(O)R'" wherein R'" is as previously defined, and
$R_2$ is (a) $C_1$–$C_{12}$ alkyl, (b) —OR"", in which R"" is a straight chain or branched $C_2$–$C_9$ alkyl which may be substituted at the terminal carbon atom by a phenyl group, or (c) —(CH$_2$)$_n$OR''' wherein n is an integer of 1 to 7 and R''' is hydrogen or C$_1$–C$_6$ alkyl;

with the proviso that R$_1$ is other than a heterocyclic moiety having a labile hydrogen atom so that said moiety acts as a carboxylic acid analogue.

2. The compound according to claim 1 wherein R$_1$ is a saturated or unsaturated cyclic moiety, an aromatic moiety or a heterocyclic moiety having from 5–20 atoms comprising one or two-ringed structures, wherein each ring comprises 3–8 carbons and 0–4 heteroatoms, said heteroatoms each independently selected from the group consisting of N, O, and S; optionally further substituted with at least one substituent selected from the group consisting of lower alkyl, halogen, nitro, cyano, —SR''', —NHR''', —N(R''')$_2$, —OR''', —COR''', —C(O)OR''' or NH—CUR''' moiety wherein R''' is hydrogen or C$_1$–C$_6$ alkyl.

3. The compound according to claim 1 wherein R$_1$ is a heterocyclic moiety selected from the group consisting of an imidazolyl, an imidazolinyl, a morpholino, a piperidyl, a piperazinyl, a pyrazolyl, a pyrrolyl, a pyrrolidinyl, a triazolyl, and a tetrazolyl, optionally further substituted wherein the substituent is selected from the group consisting of C$_{1-6}$ alkyl, C$_{1-6}$ alkyloxy, C$_{1-6}$ alkylthio, keto, carboxy, or nitro, wherein C$_{1-6}$ alkyl, C$_{1-6}$ alkoxy and C$_{1-6}$ alkylthio are intended to include saturated and unsaturated linear, branched and cyclic structures.

4. The compound according to claim 1 wherein R$_1$ is imidazolyl, pyrazolyl, 2-methyl thio-2-imidazolinyl, or 4-methylpiperidinyl.

5. The compound according to claim 1 wherein A—B is a 6(1) double bond and G is —OH or lower acyloxy.

6. The compound according to claim 5 wherein R$_2$ is 1,1-dimethylheptyl or 1,2-dimethylheptyl and wherein R$_1$ is selected from the group consisting of imidazole, pyrazole, oxazole, isoxazole, tetrahydropyridine, pyrazoline, oxazoline, pyrrolidine, imidazoline, 2-thio-imidazole, 2-methylthio-imidazoline, 4-methyl-2-imidazoline, 4,4-dimethyl-2-imidazoline, methyl sulfide, methylsulfoxide, acetamido, benzamide, cyano, 1,2,4-triazole, 1,3,4-triazole, 1,2,3,4-tetrazole, 1,2,3,5-tetrazole, thiophene, phenyl, morpholine, thiomorpholine, thiazolidine, glycerol, piperazine, piperidine and terrahydropyran, optionally further substituted wherein the substituent is selected from the group consisting of C$_{1-6}$ alkyl, C$_{1-6}$ alkyloxy, C$_{1-6}$ alkylthio, keto, carboxy, or nitro, wherein C$_{1-6}$ alkyl, C$_{1-6}$ alkoxy and C$_{1-6}$ alkylthio are intended to include saturated and unsaturated linear, branched and cyclic structures.

7. The compound according to claim 6 wherein R$_1$ is imidazole, pyrazole, 2-methyl thio-2-imidazoline, or 4-methylpiperidine.

8. The compound according to claim 1 wherein A—B is absent and G is —OH or lower acyloxy.

9. The compounds according to claim 1 selected from the group consisting of: (+)-(3 S,4 S)-6,6-Dimethyl-(1,1 -dimethylheptyl)-1-hydroxy-9- (imidazolomethyl)-6a,7,10,10a-tetrahydro-6H-dibenzo [b,d]pyran; (+)-(3S,4 S)-6,6-Dimethyl -dimethylheptyl)-1-hydroxy-9-(pyrazolomethyl)-6a,7,10,10a-tetrahydro-6H-dibenzo [b,d]pyran; (+)-(3S,4 S)-6,6-Dimethyl-(1,1-dimethylheptyl)-1-hydroxy-9-(1H-imidazol -2-ylsulfanyl methyl)-6a,7,10,10a-tetrahydro-6H-dibenzo [b,d]pyran; (+)-(3S,4S)-6,6-Dimethyl-(1,1-dimethylheptyl)-1-hydroxy-9-(4-piperidinopiperidine methyl)-6a, 7,10,10a-tetrahydro-6H-dibenzo[b,d]pyran; and (+)-(3S,4S)-6,6-Dimethyl-(1,1-dimethylheptyl) -1-hydroxy-9-(4-methylpiperidine methyl)-6a,7,10,10a-tetrahydro-6H-dibenzo [b,d]pyran.

10. A pharmaceutical composition comprising as an active ingredient a compound of the general formula (I):

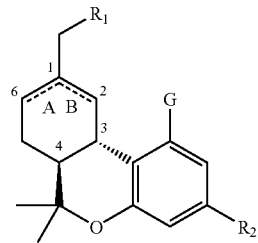

having the (3S,4S) configuration and being essentially free of the (3R,4R) enantiomer, wherein A—B indicates an optional 1(2) or 6(1) double bond, R$_1$ is A) R$_3$ where R$_3$ is selected from the group consisting of
   a) a linear or branched, saturated or unsaturated, carbon side chain comprising 1–8 carbon atoms and 1–3 heteroatoms, at least one heteroatom being placed between two carbon atoms; or
   b) a saturated or unsaturated cyclic moiety or an aromatic or heterocyclic moiety having from 5–20 atoms comprising one or two-ringed structures, wherein each ring comprises 3–8 carbons and 0–4 heteroatoms, said heteroatoms each independently selected from the group consisting of N, O, and S; wherein each ring optionally is further substituted with one or more groups selected from
      i) C$_{1-6}$ alkyl,
      ii) C$_{1-6}$ alkoxy,
      iii) C$_{1-6}$ alkylthio,
      iv) halo,
      v) carboxyl,
      vi) —CO$_2$—C$_{1-4}$ alkyl,
      vii) keto,
      viii) nitro, and
      ix) a saturated or unsaturated cyclic moiety, or an aromatic or a heterocyclic moiety comprising one or two ringed structures wherein each ring comprises 3–8 carbons and 0–4 heteroatoms, said heteroatoms each independently selected from the group consisting of N, O, and S;
         wherein each ring optionally is further substituted with one or more groups selected from i)-viii) as defined above;

B) an amine or an amide substituted with at least one substituent as defined in R$_3$ above;

C) a thiol, a sulfide, a sulfoxide, a sulfone, a thioester or a thioamide optionally substituted with one substituent as defined in R$_3$ above; or D) an ether —OR$_3$ wherein R$_3$ is as defined above;

G is (a) halogen, (b) C$_1$–C$_6$ alkyl, or (c) —OR wherein R is (a') —R'', wherein R'' is hydrogen or C$_1$–C$_6$ alkyl optionally containing a terminal —OR''' or —OC(O)R''' moiety wherein R''' is hydrogen or C$_1$–C$_6$ alkyl, or (b') —C(O)R''' wherein R''' is as previously defined, and R$_2$ is (a) C$_1$–C$_{12}$ alkyl, (b) —OR'''', in which R'''' is a straight chain or branched C$_2$–C$_9$ alkyl which may be substituted at the terminal carbon atom by a phenyl group, or (c) —(CH$_2$)$_n$OR''' wherein n is an integer of 1 to 7 and R''' is hydrogen or C$_1$–C$_6$ alkyl; with the proviso that R$_1$ is other than a heterocyclic moiety having a labile hydrogen atom so that said moiety acts as a carboxylic acid analogue; together with a pharmaceutically acceptable diluent or carrier.

11. The composition according to claim 10 wherein $R_1$ is a saturated or unsaturated cyclic moiety, an aromatic moiety or a heterocyclic moiety having from 5–20 atoms comprising one or two-ringed structures, wherein each ring comprises 3–8 carbons and 0–4 heteroatoms, said heteroatoms each independently selected from the group consisting of N, O, and S; optionally further substituted with at least one substituent selected from the group consisting of lower alkyl, halogen, nitro, cyano, —SR''', —NHR''', —N(R''')$_2$, —OR''', —COR''', —C(O)OR''' or NH—COR''' moiety wherein R''' is hydrogen or $C_1$–$C_6$ alkyl.

12. The composition according to claim 10 wherein $R_1$ is a heterocyclic moiety selected from the group consisting of an imidazolyl, an imidazolinyl, a morpholino, a piperidyl, a piperazinyl, a pyrazolyl, a pyrrolyl, a pyrrolidinyl, a triazolyl, and a tetrazolyl, optionally further substituted wherein the substituent is selected from the group consisting of $C_{1-6}$ alkyl, $C_{1-6}$ alkyloxy, $C_{1-6}$ alkylthio, keto, carboxy, or nitro, wherein $C_{1-6}$ alkyl, $C_{1-6}$ alkoxy and $C_{1-6}$ alkylthio are intended to include saturated and unsaturated linear, branched and cyclic structures.

13. The composition according to claim 10 wherein $R_1$ is imidazolyl, pyrazolyl, 2-methyl thio-2-imidazolinyl, or 4-methylpiperidinyl.

14. The composition according to claim 10, wherein A—B is a 6(1) double bond, and G is —OH or lower acyloxy.

15. The composition according to claim 14 wherein $R_2$ is 1,1-dimethylheptyl or 1,2-dimethylheptyl and wherein $R_1$ is selected from the group consisting of imidazole, pyrazole, oxazole, isoxazole, tetrahydropyridine, pyrazoline, oxazoline, pyrrolidine, imidazoline, 2-thio-imidazole, 2-methylthio-imidazoline, 4-methyl-2-imidazoline, 4,4-dimethyl-2-imidazoline, methyl sulfide, methylsulfoxide, acetamido, benzamide, cyano, 1,2,4-triazole, 1,3,4-triazole, 1,2,3,4-tetrazole, 1,2,3,5-tetrazole, thiophene, phenyl, morpholine, thiomorpholine, thiazolidine, glycerol, piperazine, piperidine and tetrahydropyran, optionally further substituted wherein the substituent is selected from the group consisting of $C_{1-6}$ alkyl, $C_{,1-6}$ alkyloxy, $C_{1-6}$ alkylthio, keto, carboxy, or nitro, wherein $C_{1-6}$ alkyl, $C_{1-6}$ alkoxy and $C_{1-6}$ alkylthio are intended to include saturated and unsaturated linear, branched and cyclic structures.

16. The composition according to claim 15 wherein $R_1$ is imidazole, pyrazole, 2-methyl thio-2-imidazoline, or 4-methylpiperidine.

17. The composition according to claim 10 wherein A—B is absent and G is OH or a lower acyloxy group.

18. The composition according to claim 10 wherein the active ingredient is selected from the group consisting of: (+)-(3S,4S)-6,6-Dimethyl-(1,1-dimethylheptyl) -1-hydroxy-9-(imidazolomethyl)-6a,7,10,10a-tetrahydro-6H-dibenzo [b,d]pyran; (+)-(3S,4S)-6,6-Dimethyl-(1,1-dimethylheptyl)-1-hydroxy-9-(pyrazolomethyl)-6a,7,10,10a-tetrahydro-6H-dibenzo [b,d]pyran; (+)-(3S,4S) -6,6-Dimethyl-(1,1-dimethylheptyl) -1-hydroxy-9-(1H-imidazol-2-ylsulfanyl methyl)-6a,7,10,10a-tetrahydro -6H-dibenzo[b,d]pyran; (+)-(3S,4S)-6,6-Dimethyl-(1,1-dimethylheptyl)-1-hydroxy -9-(4-piperidinopiperidinemethyl)-6a,7,10,10a-tetrahydro-6H-dibenzo[b,d]pyran; and (+)-(3S,4S)-6,6-Dimethyl-(1,1-dimethylheptyl)-1-hydroxy-9-(4-methylpiperidine methyl)-6a,7,10,10a-tetrahydro-6H-dibenzo[b,d]pyran.

19. The composition according to claim 10 wherein the carrier or diluent is an aqueous cosolvent solution comprising a pharmaceutically acceptable cosolvent, a micellar solution prepared wit natural or synthetic ionic or non-ionic surfactants, or a combination of such cosolvent and micellar solutions.

20. The composition according to claim 19 wherein the carrier is (a) a solution of ethanol, a surfactant, and water or (b) an emulsion comprising a triglycerides, lecithin, glycerol, an emulsifier, an antioxidant, and water.

* * * * *

UNITED STATES PATENT AND TRADEMARK OFFICE
CERTIFICATE OF CORRECTION

PATENT NO.         : 7,235,584 B2
APPLICATION NO. : 10/602745
DATED              : June 26, 2007
INVENTOR(S)        : Garzon et al.

It is certified that error appears in the above-identified patent and that said Letters Patent is hereby corrected as shown below:

Column 59:
Line 43 (claim 6, line 11), before "optionally further substituted" change "terrahydropyran," to -- tetrahydropyran, --.

Column 62:
Line 4 (claim 15, line 13), before "alkyloxy" change "$C_{,1-6}$" to -- $C_{1-6}$ --.
Line 30 (claim 19, line 4), after "solution prepared" change "wit" to -- with --.

Signed and Sealed this

Seventh Day of August, 2007

JON W. DUDAS
*Director of the United States Patent and Trademark Office*